(12) United States Patent
Brown et al.

(10) Patent No.: US 10,676,717 B2
(45) Date of Patent: *Jun. 9, 2020

(54) COSTIMULATORY CHIMERIC ANTIGEN RECEPTOR T CELLS TARGETING IL13Rα2

(71) Applicant: City of Hope, Duarte, CA (US)

(72) Inventors: Christine E. Brown, Duarte, CA (US); Stephen J. Forman, Duarte, CA (US)

(73) Assignee: City of Hope, Duarte, CA (US)

(*) Notice: Subject to any disclaimer, the term of this patent is extended or adjusted under 35 U.S.C. 154(b) by 197 days.

This patent is subject to a terminal disclaimer.

(21) Appl. No.: 15/918,901

(22) Filed: Mar. 12, 2018

(65) Prior Publication Data

US 2018/0265844 A1  Sep. 20, 2018

Related U.S. Application Data

(63) Continuation of application No. 15/167,869, filed on May 27, 2016, now Pat. No. 9,914,909, which is a continuation of application No. PCT/US2015/051089, filed on Sep. 18, 2015.

(60) Provisional application No. 62/053,068, filed on Sep. 19, 2014.

(51) Int. Cl.
C12N 5/0783 (2010.01)
C07K 14/54 (2006.01)
C07K 14/715 (2006.01)
A61K 35/17 (2015.01)
C07K 14/725 (2006.01)
C07K 14/73 (2006.01)
C07K 14/705 (2006.01)
A61K 38/00 (2006.01)

(52) U.S. Cl.
CPC ............ C12N 5/0636 (2013.01); A61K 35/17 (2013.01); C07K 14/5437 (2013.01); C07K 14/7051 (2013.01); C07K 14/70514 (2013.01); C07K 14/70578 (2013.01); C07K 14/7155 (2013.01); A61K 38/00 (2013.01); C07K 2319/03 (2013.01); C07K 2319/30 (2013.01); C07K 2319/33 (2013.01); C07K 2319/74 (2013.01); C07K 2319/75 (2013.01); C12N 2510/00 (2013.01); C12N 2740/16043 (2013.01)

(58) Field of Classification Search
None
See application file for complete search history.

(56) References Cited

U.S. PATENT DOCUMENTS

| 5,359,046 A | 10/1994 | Capon et al. |
| 5,686,281 A | 11/1997 | Roberts |
| 6,410,319 B1 | 6/2002 | Raubitschek et al. |
| 6,576,232 B1 | 6/2003 | Debinski et al. |
| 7,070,995 B2 | 7/2006 | Jensen |
| 7,446,190 B2 | 11/2008 | Sadelain et al. |
| 7,514,537 B2 | 4/2009 | Jensen et al. |
| 8,324,353 B2 | 12/2012 | Jensen |
| 8,497,118 B2 | 7/2013 | Jensen |
| 8,822,647 B2 | 9/2014 | Jensen |
| 9,217,025 B2 | 12/2015 | Jensen |
| 9,914,909 B2 * | 3/2018 | Brown ............... C07K 14/5437 |
| 2002/0164794 A1 | 11/2002 | Wernet |
| 2003/0077249 A1 | 4/2003 | Bebbington et al. |
| 2003/0171546 A1 | 9/2003 | Jensen |
| 2005/0113564 A1 | 5/2005 | Campana et al. |
| 2006/0067920 A1 | 3/2006 | Jensen |
| 2006/0269973 A1 | 11/2006 | Yee |
| 2007/0009469 A1 | 1/2007 | Kleinman et al. |
| 2007/0224189 A1 | 9/2007 | Lazar et al. |
| 2009/0257994 A1 | 10/2009 | Jensen |
| 2012/0148552 A1 | 6/2012 | Jensen |
| 2013/0287748 A1 * | 10/2013 | June ..................... A61K 35/17 424/93.21 |
| 2013/0309258 A1 | 11/2013 | June |
| 2016/0175398 A1 | 6/2016 | Jensen |

FOREIGN PATENT DOCUMENTS

| CA | 2445746 | 11/2002 |
| CN | 103492406 | 1/2014 |
| CN | 103502438 | 1/2014 |
| EP | 2532740 | 12/2012 |
| JP | 2006-528848 | 9/2004 |
| JP | 2009-515555 | 4/2009 |
| JP | 2012-501180 | 1/2012 |
| JP | 2014-510108 | 4/2014 |
| WO | WO 2000/023573 | 10/1999 |
| WO | WO 2002/088334 | 11/2002 |
| WO | WO 2007/059298 | 5/2007 |
| WO | WO 2007/071053 | 6/2007 |
| WO | WO 2008/095141 | 8/2008 |
| WO | WO 2010/025177 | 3/2010 |
| WO | WO 2010/065818 | 6/2010 |
| WO | WO 2012/024203 | 2/2012 |
| WO | WO 2012/079000 | 6/2012 |
| WO | WO 2012/129514 | 9/2012 |
| WO | WO 2014/031687 | 2/2014 |

OTHER PUBLICATIONS

DataBase GenBank: AAA52864.1, Sep. 11, 1994, [retrieved on Mar. 21, 2019] retrieved from URL <https://www.ncbi.nlm.nih.gov/protein/AAA52864.1?report=genbank&log$=protalign&blast_rank=1&RID=8FAV56XE014>, 1 page.

Armen Mardiros v. City of Hope, "Summons in a Civil Action," Case 2:19-cv-02196-CAS-MAA, Mar. 25, 2019, 83 pages.

"Protein Expression," Chapter 16 in Current Protocols in Molecular Biology (2007), published by John Wiley & Sons, pp. 16.0.1-16.25.24; 329 pages.

(Continued)

Primary Examiner — Peter J Reddig
(74) Attorney, Agent, or Firm — Fish & Richardson P.C.

(57) ABSTRACT

Chimeric transmembrane immunoreceptors (CAR) which include an extracellular domain that includes IL-13 or a variant thereof that binds interleukin-13Rα2 (IL13Rα2), a transmembrane region, a costimulatory domain and an intracellular signaling domain are described.

16 Claims, 42 Drawing Sheets

Specification includes a Sequence Listing.

(56) References Cited

OTHER PUBLICATIONS

Ahmed et al., "HER2-specific T cells target primary glioblastoma stem cells and induce regression of autologous experimental tumors," Clin. Cancer Res., 2010, 16(2): 474-85.
Altenschmidt et al., "Cytolysis of Tumor Cells Expressing in the NEU/ERBB-2, ERBB-3, and ERBB-4 Receptors by Genetically Targeted Naïve T Lymphocytes," Clinical Cancer Research, The American Association for Cancer Research, vol. 2, No. 6, Jun. 1996, 1001-1008.
Ashkenazi et al., 1995, Methods: a Companion to Methods in Enzymology, 8: 104-115.
Bailey et al., "Molecular Genetics and Control Systems," Biochemical Engineering Fundamentals, 2d Ed., 1986, 349-357.
Bonnerot et al., 1997, Immunology Letters, 47: 1-4.
Brown et al., "Recognition and killing of brain tumor stem-like initiating cells by CD8+ cytolytic T cells," Cancer Res., 2009, 69(23): 8886-93.
Brown et al., "Stem-like tumor-initiating cells isolated from IL13Ra2 expressing gliomas are targeted and killed by IL13-zetakine-redirected T Cells," Clin. Cancer Res., 2012, 18(8): 2199-209.
Brown et al., "Tumor-derived chemokine MCP-1/CCL2 is sufficient for mediating tumor tropism of adoptively transferred T cells," J. Immunol., 2007, 179(5): 3332-41.
Campbell et al., 1997, Theriology, 47(1): 63-72.
Cartellieri et al., "Chimeric antigen receptor-engineered T cells for immunotherapy of cancer," J. Biomed. Biotechnol., 2010: 956304.
Chang et al., 2006, Journal of Immunotherapy, 29(6): 628.
Chang et al., 2007, Cytotherapy, 9(8): 771-781.
Chow et al., "T cells redirected to EphA2 for the immunotherapy of glioblastoma," Mol. Ther., 2013, 21(3): 629-37.
Debinski and Thompson, "Retargeting interleukin 13 for radioimmunodetection and radioimmunotherapy of human high-grade gliomas," Clin. Cancer Res., 1999, 5(10 Suppl): 3143s-3147s.
Debinski et al., "Human glioma cells overexpress receptors for interleukin 13 and are extremely sensitive to a novel chimeric protein composed of interleukin 13 and pseudomonas exotonin," Clinical Cancer Research, 1995, 1: 1253-1258.
Debinski et al., "Novel anti-brain tumor cytotoxins specific for cancer cells," Nature Biotechnology, 1998, 16: 449-453.
Debinski et al., "Novel way to increase targeting specificity to a human glioblastoma-associated receptor for interleukin 13," Int. J. Cancer, 1998, 76: 547-551.
Debinski et al., "Receptor for interleukin 13 is a marker and therapeutic target for human high-grade gliomas," Clinical Cancer Research, 1999, 5: 985-990.
Debinski et al., "Receptor for interleukin 13 is abundantly and specifically over-expressed in patients with glioblastoma multiforme," Int. J. Oncology, 1999, 15: 481-486.
Debinski, "Expression of a restrictive receptor for interleukin 13 is associated with glial transformation," J. Neuro-Oncology, 2000, 48: 103-111.
Edelman et al., "The covalent structure of an entire GammaG immunoglobulin molecule," Proc. Natl. Acad. Sci. USA, 1969, 63(1): 78-85.
Ehtesham et al., "Recent Progress in Immunotherapy for Malignant Glioma: Treatment Strategies and Results From Clinical Trials," 2004, Cancer Control. 11(3): 192-207.
Finney, "Activation of Resting Human Primary T Cells with Chimeric Receptors: Costimulation from CD28, Inducible Costimulator, CD134, and CD137 in Series with Signals from the TCR, Chain," Journal of Immunology, 2004, 172: 104-113.
Finney, "Chimeric Receptors Providing Both Primary and Costimulatory Signaling in T Cells from a Single Gene Product," Journal of Immunology, 1998, 161: 2791-2797.
Glick et al., "Manipulation of Gene Expression in Prokaryotes," Molecular Biotechnology, 2d Ed., Ch. 6, 1998, 109-143.
Hong et al., "Successful treatment of melanoma brain metastases with adoptive cell therapy," Clin. Cancer Res., 2010, 16(19): 4892-8.
International Preliminary Report on Patentability in International Application No. PCT/US2015/051089, dated Mar. 21, 2017, 8 pages.
International Search Report and Written Opinion in International Application No. PCT/US2015/051089, dated Jan. 29, 2016, 14 pages.
Jensen et al., "CD20 is a molecular target for scFvFc:zeta receptor redirected T cells: implications for cellular immunotherapy of CD20 malignancy," Biol. Blood Marrow Transplant, 1998, 4: 75-83.
Jonnalagadda et al., "Chimeric antigen receptors (CARs) incorporating mutations in the IgG4 Fc spacer region to eliminate Fc receptor recognition results in improved CAR T cell persistence and anti-tumor efficacy," Journal for Immunotherapy of Cancer, 2013, 1(1): 18.
Joshi et al., "Interleukin-13 receptor a Chain: A novel tumor-associated transmembrane protein in primary explants of human malignant gliomas," Cancer Research, 2000, 60: 1168-1172.
Kahlon et al., "Redirecting T lymphocyte antigen specificity via engineered zetakine immonoreceptors: development of a prototype construct specific for the tumor-restricted IL-13alpha2 receptor," Molecular Therapy, May 2001, 3(5): S374.
Kahlon et al., "Specific recognition and killing of glioblastoma multiforme by interleukin 13-zetakine redirected cytolytic T cells," Cancer Res., 2004, 64(24): 9160-6.
Kahlon et al., "The IL-13 zetakine chimeric immunoreceptor: a novel approach to genetically engineer T cells for glioma immunotherapy," Neuro-Oncology, 3(4): 315-316, Oct. 2001.
Kong et al., "Suppression of Human Glioma Xenografts with Second-Generation IL13R-Specific Chimeric Antigen Receptor-Modified T cells," Clinical Cancer Research, 2012, 18(21): 5949-5960.
Lazovic et al., "Imaging Immune Response in Vivo: Cytolytic Action of Genetically Altered T Cells Directed to Glioblastoma Multiforme," 2008, Clin. Cancer Res., 14(2): 3832-3839.
Liu et al., "Interleukin-13 sensitivity and receptor phenotypes of human glial cell lines: Non-neoplastic glia and low-grade astrocytoma differ from malignant glioma," Cancer Immunol. Immunother., 2000, 49: 319-324.
Melero et al., "Amplification of tumor immunity by gene transfer of the co-stimulatory 4-1BB ligand synergy with the CD28 co-stimulatory pathway," Eur. J. Immunol., 1998, 28: 1116-1121.
Minty et al., "Interleukin-13 is a new human lymphokine regulating inflammatory and immune responses," Nature, 1993, 362: 248-250.
Mintz et al., "Cancer genetics/epigenetics and the X chromosome: Possible new links for malignant glioma pathogenesis and immune-based therapies," Crit. Rev. Oncol., 2000, 11(1): 77-95.
Moeller et al., "A functional role for CD28 costimulation in tumor recognition by single-chain receptor-modified T cells," 2004, Cancer Gene Therapy, 11: 371-379.
Murata et al., "Structure of IL-13 receptor: analysis of subunit composition in cancer and immune cells," Biochemical and Biophysical Research Communications, 1997, 238: 90-94.
Niederman et al., "Antitumor activity of cytotoxic T lympocute engineered to target vascular endothelial growth factor receptors," Proceedings of the National Academy of Sciences of USA, National Academy of Science, May 2002, 99(19): 7009-7014.
Obiri et al., "The IL-13 receptor structure differs on various cell types and may share more than one component with IL-4 receptor," J. Immunol., 1997, 158:756-764.
Sampson et al., "EGFRvIII mCAR-modified T-cell therapy cures mice with established intracerebral glioma and generates host immunity against tumor-antigen loss," Clin. Cancer Res., 2014, 20(4): 972-84.
Stastny et al., "Medulloblastomas Expressing IL13Ra2 are Targets for IL13-zetakine+ Cytolytic T Cells," J. Pediatr. Hematol. Oncol., 2007, 29: 669-677.
Thaci et al., "Significance of interleukin-13 receptor alpha 2-targeted glioblastoma therapy," Neuro-Oncology, 2014, 16(10): 1304-1312.
Thompson et al., "Mutants of interleukin 13 with altered reactivity toward interleukin 13 receptors," J. Biol. Chem., 1999, 274: 29944-29950.

(56) References Cited

OTHER PUBLICATIONS

Wang et al., "Optimizing Adoptive Polyclonal T Cell Immunotherapy of Lymphomas, Using a Chimeric T Cell Receptor Possessing CD28 and CD137 Costimulatory Domains," 2007, Human Gene Therapy, 18: 712-725.
Xu et al., "Targeting and therapy of carcinoembryonic antigen-expressing tumors in transgenic mice with an antibody-interleukin 2 fusion protein," Cancer Research, 2000, 60: 4475-4484.
Yaghoubi et al., "Noninvasive detection of therapeutic cytolytic T cells with 18F-FHBG PET in a patient with glioma," Nat. Clin. Pract. Oncol., 2009, 6(1): 53-8.
Yamasaki et al., "Specific adoptive immunotherapy of malignant glioma with long-term cytotoxic T lymphocyte line expanded in T-cell growth factor," Experimental Study and Future Prospects, Neurosurg. Rev., 1984, 7: 37-54.
Kalos et al., "T Cells with Chimeric Antigen Receptors Have Petent Antitumor Effects and Can stablish Memory in Patients with Advanced Leukemia," Science Translational Medicine Aug. 10, 2011, 3(95):95ra73, 11 pages.
European Extended Search Report in European Application No. 15842405.1, dated Mar. 7, 2018, 9 pages.
International Preliminary Report on Patentability in International Application No. PCT/US2015/051280, dated Mar. 21, 2017, 10 pages.
International Search Report and Written Opinion in International Application No. PCT/US2015/051280, dated Feb. 26, 2016, 14 pages.
Turtle et al., "A Phase I/II Clinical Trial of Immunotherapy for CD19 (+) B Cell Malignancies With Defined Composition of CD4 (+) and CD8 (+) Central Memory T Cells Lentivirally Engineered to Express a CD19-Specific Chimeric Antigen Receptor," Ther May., May 2014, 22(suppl 1):S296, 767.
Bachanova et al., "Transient regulatory T-cell (Treg) depletion with IL-2 diphtheria toxin fusion protein enhances clearance of acute myeloid leukemia by haploidentical natural killer (NK) cells," J for Immuno Canc., 2013, 1(Suppl 1):P1.
Budde et al., "Combining a CD20 Chimeric Antigen Receptor and an Inducible Caspase 9 Suicide Switch to Improve the Efficacy and Safety of T Cell Adoptive Immunotherapy for Lymphoma," PLOS ONE, Dec. 17, 2013, 8(12):1-10.
European Extended Search Report in European Application No. 19175730.1, dated Nov. 25, 2019, 11 pages.
Kim et al., "High Cleavage Efficiency of a 2A Peptide Derived from Porcine Teschovirus-1 in Human Cell Lines, Zebrafish and Mice," PLOS ONE, Apr. 29, 2011, 6(4):e18556.
Terakura et al., "Generation of CD19-chimeric antigen receptor modified CD8+ T cells derived from virus-specific central memory T cells," Blood, 2012, 119(1):72-82.

\* cited by examiner

FIGURE 1
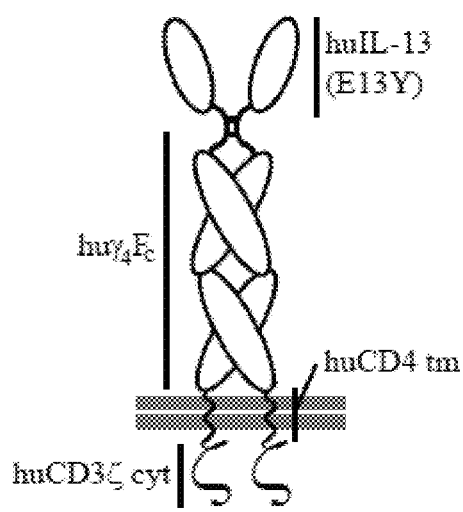
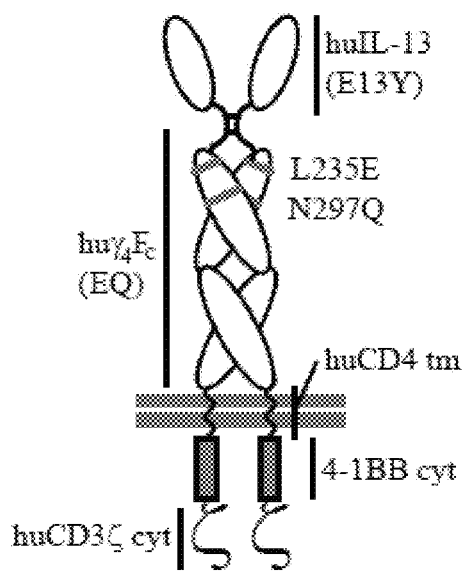

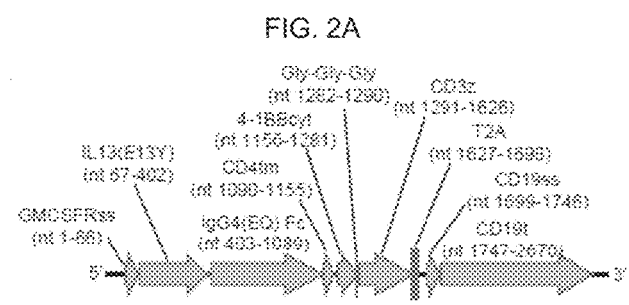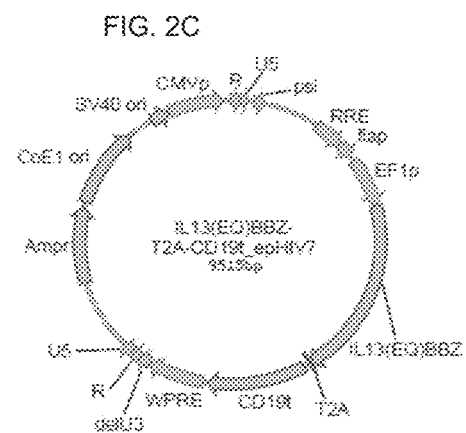

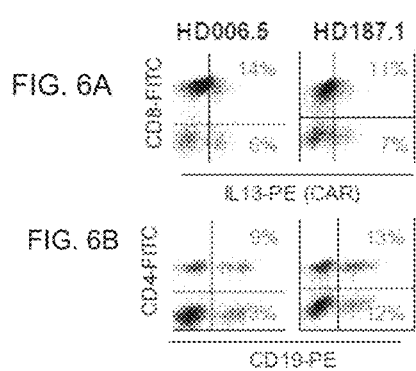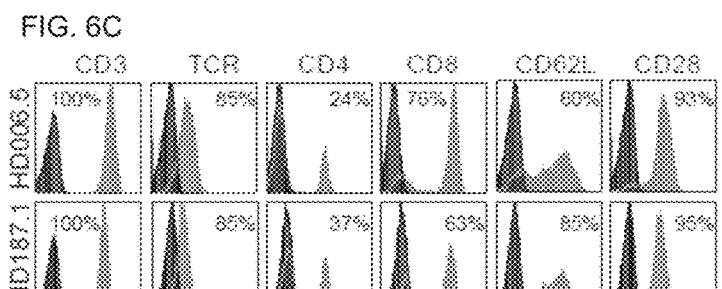

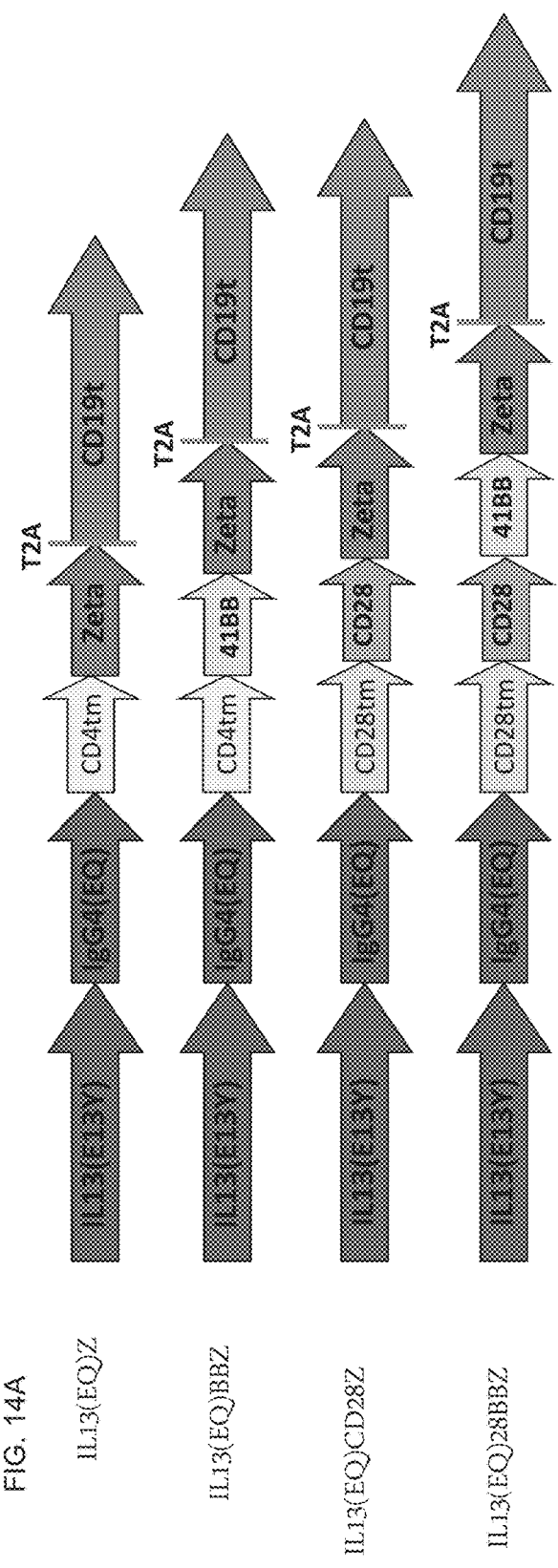
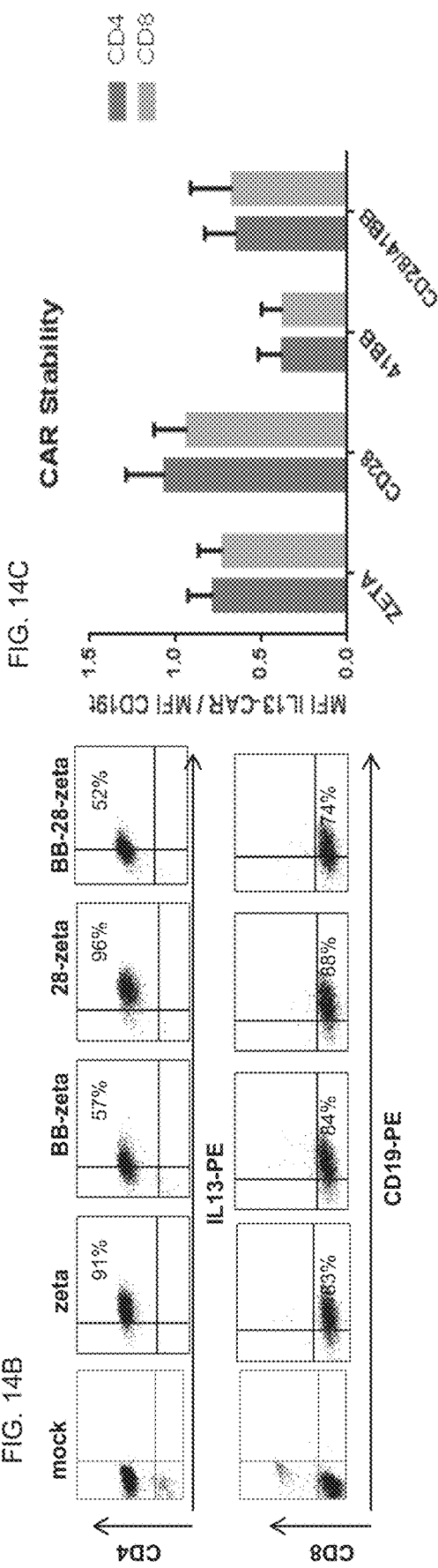
FIG. 14A
FIG. 14B
FIG. 14C

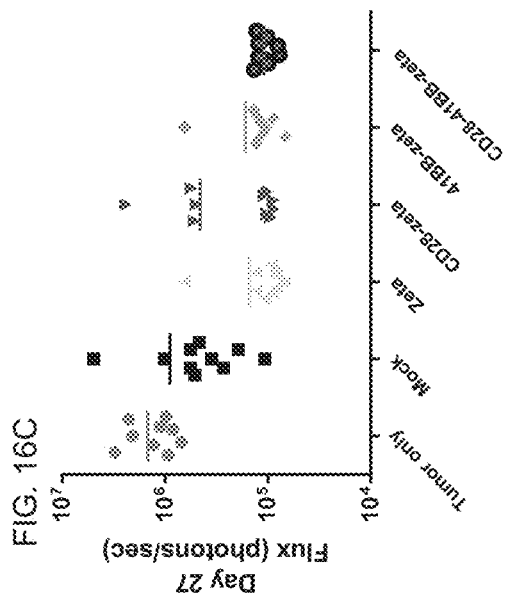
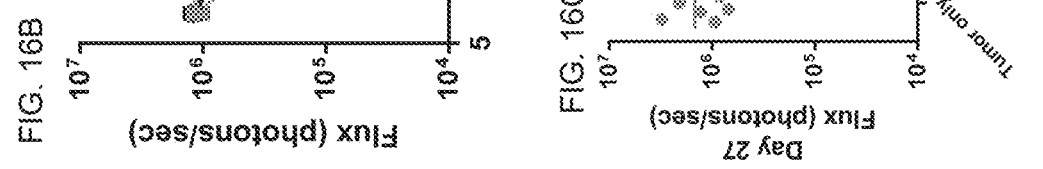
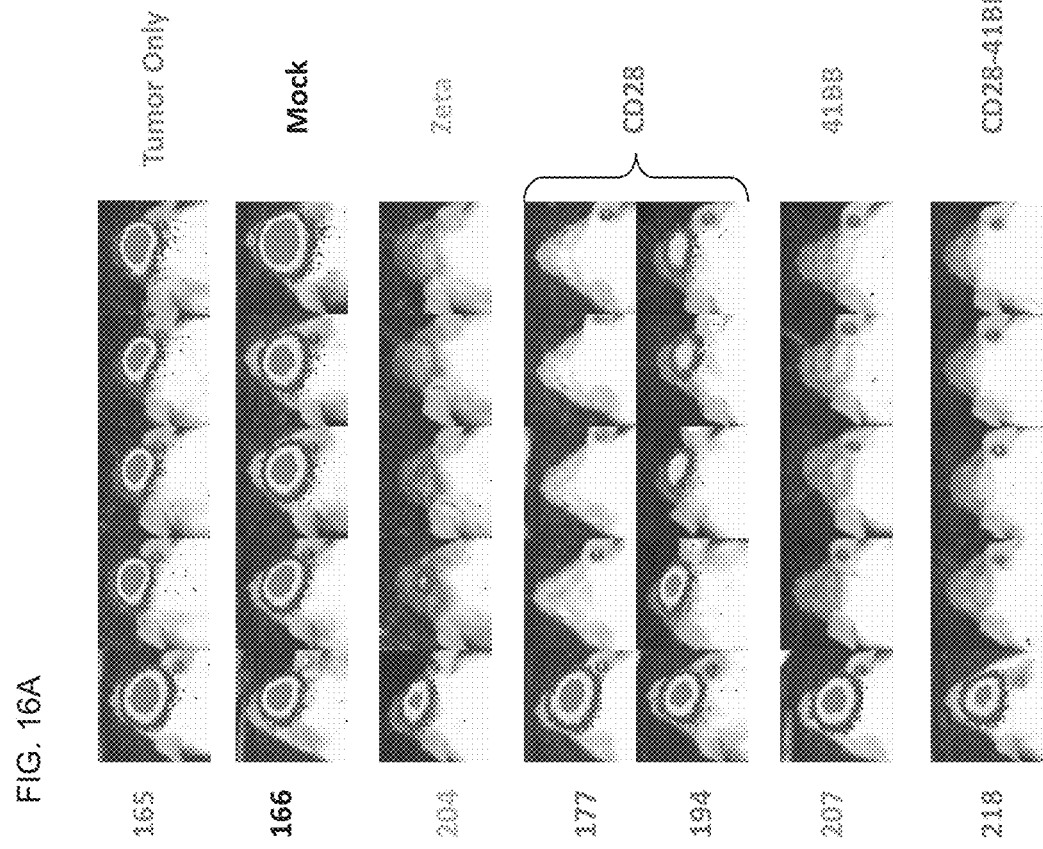

FIGURE 17 A

MLLLVTSLLLCELPHPAFLLIPGPVPPSTALRYLIEELVNITQNQKAPLCNGSMVWSINLTAGM

GMCSFRa signal peptide (22 aa)   IL13 (112 aa)

YCAALESLINVSGCSAIEKTQRMLSGFCPHKVSAGQFSSLHVRDTKIEVAQFVKDLLLHLKKLF

REGRFNESKYGPPCPPCPAPEFEGGPSVFLFPPKPKDTLMISRTPEVTCVVVDSQEDPEVQF

IgG4(L235E, N297Q in bold) (229 aa)

NWYVDGVEVHNAKTKPREEQFQSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGKMALIVLGGVAGLL

CD4tm (22 aa)

LFIGLGIFFKRGRKKLLYIFKQPFMRPVQTTQEEDGCSCRFPEEEEGGCELGGGRVKFSRSADA

41BB (42 aa)                                                                Gly3   Zeta ( 112 aa)

PAYQQGQNQLYNELNLGRREEYDVLDKRRGRDPEMGGKPRRKNPQEGLYNELQKDKMAE

AYSEIGMKGERRRGKGHDGLYQGLSTATKDTYDALHMQALPPRLEGGGEGRGSLLTCGDV

T2A (24 aa)

EENPGPRMPPPRLLFFLLFLTPMEVRPEEPLVVKVEEGDNAVLQCLKGTSDGPTQQLTWSRE

SPLKPFLKLSLGLPGLGIHMRPLAIWLFIFNVSQQMGGFYLCQPGPPSEKAWQPGWTVNVE

GSGELFRWNVSDLGGLGCGLKNRSSEGPSSPSGKLMSPKLYVWAKDRPEIWEGEPPCVPPR

DSLNQSLSQDLTMAPGSTLWLSCGVPPDSVSRGPLSWTHVHPKGPKSLLSLELKDDRPARD

MWVMETGLLLPRATAQDAGKYYCHRGNLTMSFHLEITARPVLWHWLLRTGGWKVSAVTL

AYLIFCLCSLVGILHLQRALVLRRKR

FIGURE 18 A

Yellow highlighting indicates the IL-13 optimized codon region including the
GMCSF signal sequence (IL13op).
      highlighting indicates the IgG4 optimized codon region (IgG4op[L235E,
N297Q]).
   highlighting indicates the two anticipated amino acid changes within the
IgG4 hinge region(L235E and N297Q).
       highlighting indicates the CD4 transmembrane optimized codon region.
    highlighting indicates the 41BB cytoplasmic signaling region (41BB
cyto).
     highlighting indicates the 3 glycine linkers (g3).
Gray Highlighting indicates the CD3 zeta optimized codon region (zeta op).
     highlighting indicates the T2A sequence (T2A).
    highlighting Indicates the truncated CD19 sequence (CD19t).

```
                                    1                                            50
IL13(EQ)41BBZeta       (1)   GTTAGACCAGATCTGAGCCTGGGAGCTCTCTGGCTAACTAGGGAACCCAC
CD19Rop_epHIV7         (1)   GTTAGACCAGATCTGAGCCTGGGAGCTCTCTGGCTAACTAGGGAACCCAC
      Consensus        (1)   GTTAGACCAGATCTGAGCCTGGGAGCTCTCTGGCTAACTAGGGAACCCAC
                                   51                                           100
IL13(EQ)41BBZeta      (51)   TGCTTAAGCCTCAATAAAGCTTGCCTTGAGTGCTTCAAGTAGTGTGTGCC
CD19Rop_epHIV7        (51)   TGCTTAAGCCTCAATAAAGCTTGCCTTGAGTGCTTCAAGTAGTGTGTGCC
      Consensus       (51)   TGCTTAAGCCTCAATAAAGCTTGCCTTGAGTGCTTCAAGTAGTGTGTGCC
                                  101                                           150
IL13(EQ)41BBZeta     (101)   CGTCTGTTGTGTGACTCTGGTAACTAGAGATCCCTCAGACCCTTTTAGTC
CD19Rop_epHIV7       (101)   CGTCTGTTGTGTGACTCTGGTAACTAGAGATCCCTCAGACCCTTTTAGTC
      Consensus      (101)   CGTCTGTTGTGTGACTCTGGTAACTAGAGATCCCTCAGACCCTTTTAGTC
                                  151                                           200
IL13(EQ)41BBZeta     (151)   AGTGTGGAAAATCTCTAGCAGTGGCGCCCGAACAGGGACTTGAAAGCGAA
CD19Rop_epHIV7       (151)   AGTGTGGAAAATCTCTAGCAGTGGCGCCCGAACAGGGACTTGAAAGCGAA
      Consensus      (151)   AGTGTGGAAAATCTCTAGCAGTGGCGCCCGAACAGGGACTTGAAAGCGAA
                                  201                                           250
IL13(EQ)41BBZeta     (201)   AGGGAAACCAGAGGAGCTCTCTCGACGCAGGACTCGGCTTGCTGAAGCGC
CD19Rop_epHIV7       (201)   AGGGAAACCAGAGGAGCTCTCTCGACGCAGGACTCGGCTTGCTGAAGCGC
      Consensus      (201)   AGGGAAACCAGAGGAGCTCTCTCGACGCAGGACTCGGCTTGCTGAAGCGC
                                  251                                           300
IL13(EQ)41BBZeta     (251)   GCACGGCAAGAGGCGAGGGGCGGCGACTGGTGAGTACGCCAAAAATTTTG
CD19Rop_epHIV7       (251)   GCACGGCAAGAGGCGAGGGGCGGCGACTGGTGAGTACGCCAAAAATTTTG
      Consensus      (251)   GCACGGCAAGAGGCGAGGGGCGGCGACTGGTGAGTACGCCAAAAATTTTG
                                  301                                           350
IL13(EQ)41BBZeta     (301)   ACTAGCGGAGGCTAGAAGGAGAGAGATGGGTGCGAGAGCGTCAGTATTAA
CD19Rop_epHIV7       (301)   ACTAGCGGAGGCTAGAAGGAGAGAGATGGGTGCGAGAGCGTCAGTATTAA
      Consensus      (301)   ACTAGCGGAGGCTAGAAGGAGAGAGATGGGTGCGAGAGCGTCAGTATTAA
                                  351                                           400
IL13(EQ)41BBZeta     (351)   GCGGGGGAGAATTAGATCGATGGGAAAAAATTCGGTTAAGGCCAGGGGGA
CD19Rop_epHIV7       (351)   GCGGGGGAGAATTAGATCGATGGGAAAAAATTCGGTTAAGGCCAGGGGGA
      Consensus      (351)   GCGGGGGAGAATTAGATCGATGGGAAAAAATTCGGTTAAGGCCAGGGGGA
                                  401                                           450
IL13(EQ)41BBZeta     (401)   AAGAAAAAATATAAATTAAAACATATAGTATGGGCAAGCAGGGAGCTAGA
CD19Rop_epHIV7       (401)   AAGAAAAAATATAAATTAAAACATATAGTATGGGCAAGCAGGGAGCTAGA
      Consensus      (401)   AAGAAAAAATATAAATTAAAACATATAGTATGGGCAAGCAGGGAGCTAGA
                                  451                                           500
```

FIGURE 18B

```
IL13(EQ)41BBZeta   (451) ACGATTCGCAGTTAATCCTGGCCTGTTAGAAACATCAGAAGGCTGTAGAC
CD19Rop_epHIV7     (451) ACGATTCGCAGTTAATCCTGGCCTGTTAGAAACATCAGAAGGCTGTAGAC
      Consensus    (451) ACGATTCGCAGTTAATCCTGGCCTGTTAGAAACATCAGAAGGCTGTAGAC
                         501                                              550
IL13(EQ)41BBZeta   (501) AAATACTGGGACAGCTACAACCATCCCTTCAGACAGGATCAGAAGAACTT
CD19Rop_epHIV7     (501) AAATACTGGGACAGCTACAACCATCCCTTCAGACAGGATCAGAAGAACTT
      Consensus    (501) AAATACTGGGACAGCTACAACCATCCCTTCAGACAGGATCAGAAGAACTT
                         551                                              600
IL13(EQ)41BBZeta   (551) AGATCATTATATAATACAGTAGCAACCCTCTATTGTGTGCATCAAAGGAT
CD19Rop_epHIV7     (551) AGATCATTATATAATACAGTAGCAACCCTCTATTGTGTGCATCAAAGGAT
      Consensus    (551) AGATCATTATATAATACAGTAGCAACCCTCTATTGTGTGCATCAAAGGAT
                         601                                              650
IL13(EQ)41BBZeta   (601) AGAGATAAAAGACACCAAGGAAGCTTTAGACAAGATAGAGGAAGAGCAAA
CD19Rop_epHIV7     (601) AGAGATAAAAGACACCAAGGAAGCTTTAGACAAGATAGAGGAAGAGCAAA
      Consensus    (601) AGAGATAAAAGACACCAAGGAAGCTTTAGACAAGATAGAGGAAGAGCAAA
                         651                                              700
IL13(EQ)41BBZeta   (651) ACAAAAGTAAGAAAAAGCACAGCAAGCAGCAGCTGACACAGGACACAGC
CD19Rop_epHIV7     (651) ACAAAAGTAAGAAAAAGCACAGCAAGCAGCAGCTGACACAGGACACAGC
      Consensus    (651) ACAAAAGTAAGAAAAAGCACAGCAAGCAGCAGCTGACACAGGACACAGC
                         701                                              750
IL13(EQ)41BBZeta   (701) AATCAGGTCAGCCAAAATTACCCTATAGTGCAGAACATCCAGGGGCAAAT
CD19Rop_epHIV7     (701) AATCAGGTCAGCCAAAATTACCCTATAGTGCAGAACATCCAGGGGCAAAT
      Consensus    (701) AATCAGGTCAGCCAAAATTACCCTATAGTGCAGAACATCCAGGGGCAAAT
                         751                                              800
IL13(EQ)41BBZeta   (751) GGTACATCAGGCCATATCACCTAGAACTTTAAATGCATGGGTAAAAGTAG
CD19Rop_epHIV7     (751) GGTACATCAGGCCATATCACCTAGAACTTTAAATGCATGGGTAAAAGTAG
      Consensus    (751) GGTACATCAGGCCATATCACCTAGAACTTTAAATGCATGGGTAAAAGTAG
                         801                                              850
IL13(EQ)41BBZeta   (801) TAGAAGAGAAGGCTTTCAGCCCAGAAGTGATACCCATGTTTTCAGCATTA
CD19Rop_epHIV7     (801) TAGAAGAGAAGGCTTTCAGCCCAGAAGTGATACCCATGTTTTCAGCATTA
      Consensus    (801) TAGAAGAGAAGGCTTTCAGCCCAGAAGTGATACCCATGTTTTCAGCATTA
                         851                                              900
IL13(EQ)41BBZeta   (851) TCAGAAGGAGCCACCCCACAAGATTTAAACACCATGCTAAACACAGTGGG
CD19Rop_epHIV7     (851) TCAGAAGGAGCCACCCCACAAGATTTAAACACCATGCTAAACACAGTGGG
      Consensus    (851) TCAGAAGGAGCCACCCCACAAGATTTAAACACCATGCTAAACACAGTGGG
                         901                                              950
IL13(EQ)41BBZeta   (901) GGGACATCAAGCAGCCATGCAAATGTTAAAAGAGACCATCAATGAGGAAG
CD19Rop_epHIV7     (901) GGGACATCAAGCAGCCATGCAAATGTTAAAAGAGACCATCAATGAGGAAG
      Consensus    (901) GGGACATCAAGCAGCCATGCAAATGTTAAAAGAGACCATCAATGAGGAAG
                         951                                             1000
IL13(EQ)41BBZeta   (951) CTGCAGGCAAAGAGAAGAGTGGTGCAGAGAGAAAAAAGAGCAGTGGGAAT
CD19Rop_epHIV7     (951) CTGCAGGCAAAGAGAAGAGTGGTGCAGAGAGAAAAAAGAGCAGTGGGAAT
      Consensus    (951) CTGCAGGCAAAGAGAAGAGTGGTGCAGAGAGAAAAAAGAGCAGTGGGAAT
                         1001                                            1050
IL13(EQ)41BBZeta  (1001) AGGAGCTTTGTTCCTTGGGTTCTTGGGAGCAGCAGGAAGCACTATGGGCG
CD19Rop_epHIV7    (1001) AGGAGCTTTGTTCCTTGGGTTCTTGGGAGCAGCAGGAAGCACTATGGGCG
      Consensus   (1001) AGGAGCTTTGTTCCTTGGGTTCTTGGGAGCAGCAGGAAGCACTATGGGCG
                         1051                                            1100
IL13(EQ)41BBZeta  (1051) CAGCGTCAATGACGCTGACGGTACAGGCCAGACAATTATTGTCTGGTATA
CD19Rop_epHIV7    (1051) CAGCGTCAATGACGCTGACGGTACAGGCCAGACAATTATTGTCTGGTATA
      Consensus   (1051) CAGCGTCAATGACGCTGACGGTACAGGCCAGACAATTATTGTCTGGTATA
                         1101                                            1150
IL13(EQ)41BBZeta  (1101) GTGCAGCAGCAGAACAATTTGCTGAGGGCTATTGAGGCGCAACAGCATCT
CD19Rop_epHIV7    (1101) GTGCAGCAGCAGAACAATTTGCTGAGGGCTATTGAGGCGCAACAGCATCT
      Consensus   (1101) GTGCAGCAGCAGAACAATTTGCTGAGGGCTATTGAGGCGCAACAGCATCT
```

FIGURE 18C

```
                          1151                                          1200
IL13(EQ)41BBZeta  (1151)  GTTGCAACTCACAGTCTGGGGCATCAAGCAGCTCCAGGCAAGAATCCTGG
CD19Rop_epHIV7    (1151)  GTTGCAACTCACAGTCTGGGGCATCAAGCAGCTCCAGGCAAGAATCCTGG
       Consensus  (1151)  GTTGCAACTCACAGTCTGGGGCATCAAGCAGCTCCAGGCAAGAATCCTGG
                          1201                                          1250
IL13(EQ)41BBZeta  (1201)  CTGTGGAAAGATACCTAAAGGATCAACAGCTCCTGGGGATTTGGGGTTGC
CD19Rop_epHIV7    (1201)  CTGTGGAAAGATACCTAAAGGATCAACAGCTCCTGGGGATTTGGGGTTGC
       Consensus  (1201)  CTGTGGAAAGATACCTAAAGGATCAACAGCTCCTGGGGATTTGGGGTTGC
                          1251                                          1300
IL13(EQ)41BBZeta  (1251)  TCTGGAAAACTCATTTGCACCACTGCTGTGCCTTGGATCTACAAATGGCA
CD19Rop_epHIV7    (1251)  TCTGGAAAACTCATTTGCACCACTGCTGTGCCTTGGATCTACAAATGGCA
       Consensus  (1251)  TCTGGAAAACTCATTTGCACCACTGCTGTGCCTTGGATCTACAAATGGCA
                          1301                                          1350
IL13(EQ)41BBZeta  (1301)  GTATTCATCCACAATTTTAAAAGAAAAGGGGGGATTGGGGGGTACAGTGC
CD19Rop_epHIV7    (1301)  GTATTCATCCACAATTTTAAAAGAAAAGGGGGGATTGGGGGGTACAGTGC
       Consensus  (1301)  GTATTCATCCACAATTTTAAAAGAAAAGGGGGGATTGGGGGGTACAGTGC
                          1351                                          1400
IL13(EQ)41BBZeta  (1351)  AGGGGAAAGAATAGTAGACATAATAGCAACAGACATACAAACTAAAGAAT
CD19Rop_epHIV7    (1351)  AGGGGAAAGAATAGTAGACATAATAGCAACAGACATACAAACTAAAGAAT
       Consensus  (1351)  AGGGGAAAGAATAGTAGACATAATAGCAACAGACATACAAACTAAAGAAT
                          1401                                          1450
IL13(EQ)41BBZeta  (1401)  TACAAAAACAAATTACAAAAATTCAAAATTTTCGGGTTTATTACAGGGAC
CD19Rop_epHIV7    (1401)  TACAAAAACAAATTACAAAAATTCAAAATTTTCGGGTTTATTACAGGGAC
       Consensus  (1401)  TACAAAAACAAATTACAAAAATTCAAAATTTTCGGGTTTATTACAGGGAC
                          1451                                          1500
IL13(EQ)41BBZeta  (1451)  AGCAGAGATCCAGTTTGGGGATCAATTGCATGAAGAATCTGCTTAGGGTT
CD19Rop_epHIV7    (1451)  AGCAGAGATCCAGTTTGGGGATCAATTGCATGAAGAATCTGCTTAGGGTT
       Consensus  (1451)  AGCAGAGATCCAGTTTGGGGATCAATTGCATGAAGAATCTGCTTAGGGTT
                          1501                                          1550
IL13(EQ)41BBZeta  (1501)  AGGCGTTTTGCGCTGCTTCGCGAGGATCTGCGATCGCTCCGGTGCCCGTC
CD19Rop_epHIV7    (1501)  AGGCGTTTTGCGCTGCTTCGCGAGGATCTGCGATCGCTCCGGTGCCCGTC
       Consensus  (1501)  AGGCGTTTTGCGCTGCTTCGCGAGGATCTGCGATCGCTCCGGTGCCCGTC
                          1551                                          1600
IL13(EQ)41BBZeta  (1551)  AGTGGGCAGAGCGCACATCGCCCACAGTCCCGAGAAGTTGGGGGGAGGG
CD19Rop_epHIV7    (1551)  AGTGGGCAGAGCGCACATCGCCCACAGTCCCGAGAAGTTGGGGGGAGGG
       Consensus  (1551)  AGTGGGCAGAGCGCACATCGCCCACAGTCCCGAGAAGTTGGGGGGAGGG
                          1601                                          1650
IL13(EQ)41BBZeta  (1601)  GTCGGCAATTGAACCGGTGCCTAGAGAAGGTGGCGCGGGGTAAACTGGGA
CD19Rop_epHIV7    (1601)  GTCGGCAATTGAACCGGTGCCTAGAGAAGGTGGCGCGGGGTAAACTGGGA
       Consensus  (1601)  GTCGGCAATTGAACCGGTGCCTAGAGAAGGTGGCGCGGGGTAAACTGGGA
                          1651                                          1700
IL13(EQ)41BBZeta  (1651)  AAGTGATGTCGTGTACTGGCTCCGCCTTTTCCCGAGGGTGGGGAGAAC
CD19Rop_epHIV7    (1651)  AAGTGATGTCGTGTACTGGCTCCGCCTTTTCCCGAGGGTGGGGAGAAC
       Consensus  (1651)  AAGTGATGTCGTGTACTGGCTCCGCCTTTTCCCGAGGGTGGGGAGAAC
                          1701                                          1750
IL13(EQ)41BBZeta  (1701)  CGTATATAAGTGCAGTAGTCGCCGTGAACGTTCTTTTTCGCAACGGGTTT
CD19Rop_epHIV7    (1701)  CGTATATAAGTGCAGTAGTCGCCGTGAACGTTCTTTTTCGCAACGGGTTT
       Consensus  (1701)  CGTATATAAGTGCAGTAGTCGCCGTGAACGTTCTTTTTCGCAACGGGTTT
                          1751                                          1800
IL13(EQ)41BBZeta  (1751)  GCCGCCAGAACACAGCTGAAGCTTCGAGGGGCTCGCATCTCTCCTTCACG
CD19Rop_epHIV7    (1751)  GCCGCCAGAACACAGCTGAAGCTTCGAGGGGCTCGCATCTCTCCTTCACG
       Consensus  (1751)  GCCGCCAGAACACAGCTGAAGCTTCGAGGGGCTCGCATCTCTCCTTCACG
                          1801                                          1850
IL13(EQ)41BBZeta  (1801)  CGCCCGCCGCCCTACCTGAGGCCGCCATCCACGCCGGTTGAGTCGCGTTC
CD19Rop_epHIV7    (1801)  CGCCCGCCGCCCTACCTGAGGCCGCCATCCACGCCGGTTGAGTCGCGTTC
```

FIGURE 18D

```
         Consensus  (1801) CGCCCGCCGCCCTACCTGAGGCCGCCATCCACGCCGGTTGAGTCGCGTTC
                           1851                                              1900
IL13(EQ)41BBZeta   (1851) TGCCGCCTCCCGCCTGTGGTGCCTCCTGAACTGCGTCCGCCGTCTAGGTA
    CD19Rop_epHIV7 (1851) TGCCGCCTCCCGCCTGTGGTGCCTCCTGAACTGCGTCCGCCGTCTAGGTA
         Consensus (1851) TGCCGCCTCCCGCCTGTGGTGCCTCCTGAACTGCGTCCGCCGTCTAGGTA
                           1901                                              1950
IL13(EQ)41BBZeta   (1901) AGTTTAAAGCTCAGGTCGAGACCGGGCCTTTGTCCGGCGCTCCCTTGGAG
    CD19Rop_epHIV7 (1901) AGTTTAAAGCTCAGGTCGAGACCGGGCCTTTGTCCGGCGCTCCCTTGGAG
         Consensus (1901) AGTTTAAAGCTCAGGTCGAGACCGGGCCTTTGTCCGGCGCTCCCTTGGAG
                           1951                                              2000
IL13(EQ)41BBZeta   (1951) CCTACCTAGACTCAGCCGGCTCTCCACGCTTTGCCTGACCCTGCTTGCTC
    CD19Rop_epHIV7 (1951) CCTACCTAGACTCAGCCGGCTCTCCACGCTTTGCCTGACCCTGCTTGCTC
         Consensus (1951) CCTACCTAGACTCAGCCGGCTCTCCACGCTTTGCCTGACCCTGCTTGCTC
                           2001                                              2050
IL13(EQ)41BBZeta   (2001) AACTCTACGTCTTTGTTTCGTTTTCTGTTCTGCGCCGTTACAGATCCAAG
    CD19Rop_epHIV7 (2001) AACTCTACGTCTTTGTTTCGTTTTCTGTTCTGCGCCGTTACAGATCCAAG
         Consensus (2001) AACTCTACGTCTTTGTTTCGTTTTCTGTTCTGCGCCGTTACAGATCCAAG
                           2051                                              2100
IL13(EQ)41BBZeta   (2051) CTGTGACCGGCGCCTACGGCTAGCGCCGCCACCATGCTGCTGCTGGTGAC
    CD19Rop_epHIV7 (2051) CTGTGACCGGCGCCTACGGCTAGCGCCGCCACCATGCTGCTGCTGGTGAC
         Consensus (2051) CTGTGACCGGCGCCTACGGCTAGCGCCGCCACCATGCTGCTGCTGGTGAC
                           2101                                              2150
IL13(EQ)41BBZeta   (2101) CAGCCTGCTGCTGTGCGAGCTGCCCCACCCCGCCTTTCTGCTGATCCCTG
    CD19Rop_epHIV7 (2101) CAGCCTGCTGCTGTGCGAGCTGCCCCACCCCGCCTTTCTGCTGATCCCCG
         Consensus (2101) CAGCCTGCTGCTGTGCGAGCTGCCCCACCCCGCCTTTCTGCTGATCCCC G
                           2151                                              2200
IL13(EQ)41BBZeta   (2151) GC--CCCG-TGCCCCTAGCACCGCC---CTGCGCTACCTGATCGAGGAA
    CD19Rop_epHIV7 (2151) ACATCCAGATGACCCAGACCACCTCCAGCCTGAGCGCCAGCCTGGGCGAC
         Consensus (2151)   C  CC G  TG CCC  A CACC CC    CTG GC  C      T G  GA
                           2201                                              2250
IL13(EQ)41BBZeta   (2195) CTGGTGA-------------------------ACATCACCCAGAACCAGAA
    CD19Rop_epHIV7 (2201) CGGGTGACCATCAGCTGCCGGGCCAGCCAGGACATCAGCAAGTACCTGAA
         Consensus (2201) C GGTGA                         ACATCA C AG ACC GAA
                           2251                                              2300
IL13(EQ)41BBZeta   (2221) ---------------AGCCC--------CC----------CTGTGCAAC----
    CD19Rop_epHIV7 (2251) CTGGTATCAGCAGAAGCCCGACGGCACCGTCAAGCTGCTGATCTACCACA
         Consensus (2251)                AGCCC        CC          CTG  C AC
                           2301                                              2350
IL13(EQ)41BBZeta   (2237) ------GGCAGCAT---GGTGTG--------------------
    CD19Rop_epHIV7 (2301) CCAGCCGGCTGCACAGCGGCGTGCCCAGCCGGTTTAGCGGCAGCGGCTCC
         Consensus (2301)       GGC GCA    GG GTG
                           2351                                              2400
IL13(EQ)41BBZeta   (2251) ------------------GAGCATC---AACCTG-----------------
    CD19Rop_epHIV7 (2351) GGCACCGACTACAGCCTGACCATCTCCAACCTGGAACAGGAAGATATCGC
         Consensus (2351)                    GA CATC   AACCTG
                           2401                                              2450
IL13(EQ)41BBZeta   (2264) -ACC-------GCCGGCATGT------ACTG-----------TGCCGCC-
    CD19Rop_epHIV7 (2401) CACCTACTTTTGCCAGCAGGGCAACACACTGCCCTACACCTTTGGCGGCG
         Consensus (2401)  ACC       GCC GCA G      ACTG           TG CG C
                           2451                                              2500
IL13(EQ)41BBZeta   (2288) --------CTGGAAA-------GCCTGATCAACGTGAGCGGCT---------
    CD19Rop_epHIV7 (2451) GAACAAAGCTGGAAATCACCGGCAGCACCTCCGGCAGCGGCAAGCCTGGC
         Consensus (2451)         CTGGAAA       GC   A C  CG  AGCGGC
                           2501                                              2550
IL13(EQ)41BBZeta   (2316) -----------GCAGCGCCATCG----------------AGAAAA--------
```

FIGURE 18E

```
CD19Rop_epHIV7  (2501) AGCGGCGAGGGCAGCACCAAGGGCGAGGTGAAGCTGCAGGAAAGCGGCCC
     Consensus  (2501)     GCAGC   CCA   G              AG AAA
                       2551                                                    2600
IL13(EQ)41BBZeta (2334) --------------CCCAGCG-----------------------------
CD19Rop_epHIV7  (2551) TGGCCTGGTGGCCCCAGCCAGAGCCTGAGCGTGACCTGCACCGTGAGCG
     Consensus  (2551)                CCCAGC
                       2601                                                    2650
IL13(EQ)41BBZeta (2341) ----GATGCTGTCCGGCTTCTGC-------------------CCCCACAAG
CD19Rop_epHIV7  (2601) GCGTGAGCCTGCCCGACTACGGCGTGAGCTGGATCCGGCAGCCCCCCAGG
     Consensus  (2601)     GA  CTG CCG CT C GC                    CCCC CA G
                       2651                                                    2700
IL13(EQ)41BBZeta (2369) ------------------------------GTGTCCGCCGGAC-----AGTT
CD19Rop_epHIV7  (2651) AAGGGCCTGGAATGGCTGGGCGTGATCTGGGGCAGCGAGACCACCTACTA
     Consensus  (2651)                               G G C GC     GAC      A T
                       2701                                                    2750
IL13(EQ)41BBZeta (2386) CAGCAGCCTGC--ACGTGCGGG-----------------ACACCAAGA
CD19Rop_epHIV7  (2701) CAACAGCGCCCTGAAGAGCCGGCTGACCATCATCAAGGACAACAGCAAGA
     Consensus  (2701) CA CAGC   C  A G GC GG                   ACA CAAGA
                       2751                                                    2800
IL13(EQ)41BBZeta (2415) TCGAGGTGGCCCAGTTCGTGAAGGACCTGCTG----------------C
CD19Rop_epHIV7  (2751) GCCAGGTGTTCCTGAAGATGAACAGCCTGCAGACCGACGACACCGCCATC
     Consensus  (2751)  C  AGGTG  CC G      TGAA   CCTGC G                C
                       2801                                                    2850
IL13(EQ)41BBZeta (2448) TGCACCTG-----AAGAA--------------GCTGTTCCG----GGA----
CD19Rop_epHIV7  (2801) TACTACTGCGCCAAGCACTACTACTACGGCGGCAGCTACGCCATGGACTA
     Consensus  (2801) T C  CTG     AAG A                GC G T CG    GGA
                       2851                                                    2900
IL13(EQ)41BBZeta (2473) ---GGGCCGGTTCAAC-------------------
CD19Rop_epHIV7  (2851) CTGGGGCCAGGGCACCAGCGTGACCGTGAGCAGCGAGAGCAAGTACGGCC
     Consensus  (2851)     GGGCC G  CA C                    GAGAGCAAGTACGGCC
                       2901                                                    2950
IL13(EQ)41BBZeta (2502)
CD19Rop_epHIV7  (2901) CTCCCTGCCCCCCTTGCCCTGCCCCCGAGTTCCTGGGCGGACCCAGCGTG
     Consensus  (2901) CTCCCTGCCCCCCTTGCCCTGCCCC GAGTTC   GGGCGGACCCAGCGTG
                       2951                                                    3000
IL13(EQ)41BBZeta (2552)
CD19Rop_epHIV7  (2951) TTCCTGTTCCCCCCCAAGCCCAAGGACACCCTGATGATCAGCCGGACCCC
     Consensus  (2951) TTCCTGTTCCCCCCCAAGCCCAAGGACACCCTGATGATCAGCCGGACCCC
                       3001                                                    3050
IL13(EQ)41BBZeta (2602)
CD19Rop_epHIV7  (3001) CGAGGTGACCTGCGTGGTGGTGGACGTGAGCCAGGAAGATCCCGAGGTCC
     Consensus  (3001)  GAGGTGACCTGCGTGGTGGTGGACGTGAGCCAGGAAGATCC GAGGTCC
                       3051                                                    3100
IL13(EQ)41BBZeta (2652)
CD19Rop_epHIV7  (3051) AGTTCAATTGGTACGTGGACGGCGTGGAGGTGCACAACGCCAAGACCAAG
     Consensus  (3051) AGTTCAATTGGTACGTGGACGGCGTGGAGGTGCACAACGCCAAGACCAAG
                       3101                                                    3150
IL13(EQ)41BBZeta (2702)
CD19Rop_epHIV7  (3101) CCCAGGGAAGAGCAGTTCAACAGCACCTACCGGGTGGTGTCCGTGCTGAC
     Consensus  (3101) CCCAGGGAAGAGCAGTTC A AGCACCTACCGGGTGGTGTCCGTGCTGAC
                       3151                                                    3200
IL13(EQ)41BBZeta (2752)
CD19Rop_epHIV7  (3151) CGTGCTGCACCAGGACTGGCTGAACGGCAAAGAATACAAGTGCAAGGTGT
     Consensus  (3151) CGTGCTGCACCAGGACTGGCTGAACGGCAAAGAATACAAGTGCAAGGTGT
                       3201                                                    3250
```

FIGURE 18F

```
IL13(EQ)41BBZeta  (2802)
CD19Rop_epHIV7    (3201) CCAACAAGGGCCTGCCCAGCAGCATCGAGAAAACCATCAGCAAGGCCAAG
     Consensus    (3201) CCAACAAGGGCCTGCCCAGCAGCATCGAGAAAACCATCAGCAAGGCCAAG
                         3251                                            3300
IL13(EQ)41BBZeta  (2852)
CD19Rop_epHIV7    (3251) GGCCAGCCTCGGGAGCCCCAGGTGTACACCCTGCCCCCTTCCCAGGAAGA
     Consensus    (3251) GGCCAGCCTCGGGAGCCCCAGGTGTACACCCTGCCCCCTTCCCAGGAAGA
                         3301                                            3350
IL13(EQ)41BBZeta  (2902)
CD19Rop_epHIV7    (3301) GATGACCAAGAATCAGGTGTCCCTGACCTGCCTGGTGAAGGGCTTCTACC
     Consensus    (3301) GATGACCAAGAATCAGGTGTCCCTGACCTGCCTGGTGAAGGGCTTCTACC
                         3351                                            3400
IL13(EQ)41BBZeta  (2952)
CD19Rop_epHIV7    (3351) CCAGCGACATCGCCGTGGAGTGGGAGAGCAACGGCCAGCCCGAGAACAAC
     Consensus    (3351) CCAGCGACATCGCCGTGGAGTGGGAGAGCAACGGCCAGCCCGAGAACAAC
                         3401                                            3450
IL13(EQ)41BBZeta  (3002) TACAAGACCACCCCCCCTGTGCTGGACAGCGACGGCAGCTTCTTCCTGTA
CD19Rop_epHIV7    (3401) TACAAGACCACCCCCCCTGTGCTGGACAGCGACGGCAGCTTCTTCCTGTA
     Consensus    (3401) TACAAGACCACCCCCCCTGTGCTGGACAGCGACGGCAGCTTCTTCCTGTA
                         3451                                            3500
IL13(EQ)41BBZeta  (3052) CAGCAGGCTGACCGTGGACAAGAGCCGGTGGCAGGAAGGCAACGTCTTTA
CD19Rop_epHIV7    (3451) CAGCAGGCTGACCGTGGACAAGAGCCGGTGGCAGGAAGGCAACGTCTTTA
     Consensus    (3451) CAGCAGGCTGACCGTGGACAAGAGCCGGTGGCAGGAAGGCAACGTCTTTA
                         3501                                            3550
IL13(EQ)41BBZeta  (3102) GCTGCAGCGTGATGCACGAGGCCCTGCACAACCACTACACCCAGAAGAGC
CD19Rop_epHIV7    (3501) GCTGCAGCGTGATGCACGAGGCCCTGCACAACCACTACACCCAGAAGAGC
     Consensus    (3501) GCTGCAGCGTGATGCACGAGGCCCTGCACAACCACTACACCCAGAAGAGC
                         3551                                            3600
IL13(EQ)41BBZeta  (3152) CTGTCCCTGAGCCTGGGCAAG
CD19Rop_epHIV7    (3551) CTGTCCCTGAGCCTGGGCAAGATGGCCCTGATCGTGCTGGGCGGCGTGGC
     Consensus    (3551) CTGTCCCTGAGCCTGGGCAAGATGGCCCTGATCGTGCTGGGCGGCGTGGC
                         3601                                            3650
IL13(EQ)41BBZeta  (3202)
CD19Rop_epHIV7    (3601) CGGGCTGCTGCTGTTCATCGGCCTGGGCATCTTTTTC--------------
     Consensus    (3601) CGGGCTGCTGCTGTTCATCGGCCTGGGCATCTTTTTC
                         3651                                            3700
IL13(EQ)41BBZeta  (3252)
CD19Rop_epHIV7    (3638) ------------------------------C-------------------
     Consensus    (3651)                               C
                         3701                                            3750
IL13(EQ)41BBZeta  (3302)
CD19Rop_epHIV7    (3639) --------------------------------------------------
     Consensus    (3701)
                         3751                                            3800
IL13(EQ)41BBZeta  (3352)                            CGGGTGAAGTTCAGCCGGTCCGCCGACG
CD19Rop_epHIV7    (3639) -----------------------GGGTGAAGTTCAGCCGGTCCGCCGACG
     Consensus    (3751)                         GGGTGAAGTTCAGCCGGTCCGCCGACG
                         3801                                            3850
IL13(EQ)41BBZeta  (3402) CCCCTGCCTACCAGCAGGGCCAGAACCAGCTGTACAACGAGCTGAACCTG
CD19Rop_epHIV7    (3666) CCCCTGCCTACCAGCAGGGCCAGAACCAGCTGTACAACGAGCTGAACCTG
     Consensus    (3801) CCCCTGCCTACCAGCAGGGCCAGAACCAGCTGTACAACGAGCTGAACCTG
                         3851                                            3900
IL13(EQ)41BBZeta  (3452) GGCAGGCGGGAGGAATACGACGTGCTGGACAAGCGGAGAGGCCGGGACCC
CD19Rop_epHIV7    (3716) GGCAGGCGGGAGGAATACGACGTGCTGGACAAGCGGAGAGGCCGGGACCC
     Consensus    (3851) GGCAGGCGGGAGGAATACGACGTGCTGGACAAGCGGAGAGGCCGGGACCC
```

FIGURE 18G

```
                              3901                                         3950
IL13(EQ)41BBZeta  (3502)  TGAGATGGGCGGCAAGCCTCGGCGGAAGAACCCCCAGGAAGGCCTGTATA
CD19Rop_epHIV7    (3766)  TGAGATGGGCGGCAAGCCCAGGCGGAAGAACCCTCAGGAAGGCCTGTATA
      Consensus   (3901)  TGAGATGGGCGGCAAGCC  GGCGGAAGAACCC CAGGAAGGCCTGTATA
                              3951                                         4000
IL13(EQ)41BBZeta  (3552)  ACGAACTGCAGAAAGACAAGATGGCCGAGGCCTACAGCGAGATCGGCATG
CD19Rop_epHIV7    (3816)  ACGAACTGCAGAAAGACAAGATGGCCGAGGCCTACAGCGAGATCGGCATG
      Consensus   (3951)  ACGAACTGCAGAAAGACAAGATGGCCGAGGCCTACAGCGAGATCGGCATG
                              4001                                         4050
IL13(EQ)41BBZeta  (3602)  AAGGGCGAGCGGAGGCGGGGCAAGGGCCACGACGGCCTGTATCAGGGCCT
CD19Rop_epHIV7    (3866)  AAGGGCGAGCGGCGGAGGGGCAAGGGCCACGACGGCCTGTACCAGGGCCT
      Consensus   (4001)  AAGGGCGAGCGG GG GGGGCAAGGGCCACGACGGCCTGTA CAGGGCCT
                              4051                                         4100
IL13(EQ)41BBZeta  (3652)  GTCCACCGCCACCAAGGATACCTACGACGCCCTGCACATGCAGGCCCTGC
CD19Rop_epHIV7    (3916)  GAGCACCGCCACCAAGGATACCTACGACGCCCTGCACATGCAGGCCCTGC
      Consensus   (4051)  G  CACCGCCACCAAGGATACCTACGACGCCCTGCACATGCAGGCCCTGC
                              4101                                         4150
IL13(EQ)41BBZeta  (3702)  CCCCAAGG
CD19Rop_epHIV7    (3966)  CCCC---------------------------------------------
      Consensus   (4101)  CCCC
                              4151                                         4200
IL13(EQ)41BBZeta  (3752)
CD19Rop_epHIV7    (3970)  --------------------------------------------------
      Consensus   (4151)
                              4201                                         4250
IL13(EQ)41BBZeta  (3802)
CD19Rop_epHIV7    (3970)  --------------------------------------------------
      Consensus   (4201)
                              4251                                         4300
IL13(EQ)41BBZeta  (3852)
CD19Rop_epHIV7    (3970)  --------------------------------------------------
      Consensus   (4251)
                              4301                                         4350
IL13(EQ)41BBZeta  (3902)
CD19Rop_epHIV7    (3970)  --------------------------------------------------
      Consensus   (4301)
                              4351                                         4400
IL13(EQ)41BBZeta  (3952)
CD19Rop_epHIV7    (3970)  --------------------------------------------------
      Consensus   (4351)
                              4401                                         4450
IL13(EQ)41BBZeta  (4002)
CD19Rop_epHIV7    (3970)  --------------------------------------------------
      Consensus   (4401)
                              4451                                         4500
IL13(EQ)41BBZeta  (4052)
CD19Rop_epHIV7    (3970)  --------------------------------------------------
      Consensus   (4451)
                              4501                                         4550
IL13(EQ)41BBZeta  (4102)
CD19Rop_epHIV7    (3970)  --------------------------------------------------
      Consensus   (4501)
                              4551                                         4600
IL13(EQ)41BBZeta  (4152)
CD19Rop_epHIV7    (3970)  --------------------------------------------------
```

FIGURE 18H

```
        Consensus  (4551)
                          4601                                               4650
IL13(EQ)41BBZeta  (4202)
    CD19Rop_epHIV7  (3970) --------------------------------------------------
        Consensus  (4601)
                          4651                                               4700
IL13(EQ)41BBZeta  (4252)
    CD19Rop_epHIV7  (3970) --------------------------------------------------
        Consensus  (4651)
                          4701                                               4750
IL13(EQ)41BBZeta  (4302)
    CD19Rop_epHIV7  (3970) -------------------------------C------AGG---------
        Consensus  (4701)                                 C      AGG
                          4751                                               4800
IL13(EQ)41BBZeta  (4352)
    CD19Rop_epHIV7  (3974) ------------------------------------T-------------
        Consensus  (4751)
                          4801                                               4850
IL13(EQ)41BBZeta  (4402)
    CD19Rop_epHIV7  (3975) --------------------------------------------------
        Consensus  (4801)
                          4851                                               4900
IL13(EQ)41BBZeta  (4452)
    CD19Rop_epHIV7  (3975) --------------------------------------------------
        Consensus  (4851)
                          4901                                               4950
IL13(EQ)41BBZeta  (4502)
    CD19Rop_epHIV7  (3975) --------------------------------------------------
        Consensus  (4901)
                          4951                                               5000
IL13(EQ)41BBZeta  (4552)
    CD19Rop_epHIV7  (3975) --------------------------------------------------
        Consensus  (4951)
                          5001                                               5050
IL13(EQ)41BBZeta  (4602)
    CD19Rop_epHIV7  (3975) --------------------------------------------------
        Consensus  (5001)
                          5051                                               5100
IL13(EQ)41BBZeta  (4652)
    CD19Rop_epHIV7  (3975) --------------------------------------------------
        Consensus  (5051)
                          5101                                               5150
IL13(EQ)41BBZeta  (4702)
    CD19Rop_epHIV7  (3975) --------------------------------------------------
        Consensus  (5101)
                          5151                                               5200
IL13(EQ)41BBZeta  (4752)    TCTAGACCCGGGCTGCAGGAATTCGATATCAAGCTTATCGATAATCAA
    CD19Rop_epHIV7  (3975) ------GACCCGGGCTGCAGGAATTCGATATCAAGCTTATCGATAATCAA
        Consensus  (5151)        GACCCGGGCTGCAGGAATTCGATATCAAGCTTATCGATAATCAA
                          5201                                               5250
IL13(EQ)41BBZeta  (4802) CCTCTGGATTACAAAATTTGTGAAAGATTGACTGGTATTCTTAACTATGT
    CD19Rop_epHIV7  (4019) CCTCTGGATTACAAAATTTGTGAAAGATTGACTGGTATTCTTAACTATGT
        Consensus  (5201) CCTCTGGATTACAAAATTTGTGAAAGATTGACTGGTATTCTTAACTATGT
                          5251                                               5300
IL13(EQ)41BBZeta  (4852) TGCTCCTTTTACGCTATGTGGATACGCTGCTTTAATGCCTTTGTATCATG
```

FIGURE 18I

| | | |
|---|---|---|
| CD19Rop_epHIV7 | (4069) | TGCTCCTTTTACGCTATGTGGATACGCTGCTTTAATGCCTTTGTATCATG |
| Consensus | (5251) | TGCTCCTTTTACGCTATGTGGATACGCTGCTTTAATGCCTTTGTATCATG |
| | | 5301                                            5350 |
| IL13(EQ)41BBZeta | (4902) | CTATTGCTTCCCGTATGGCTTTCATTTTCTCCTCCTTGTATAAATCCTGG |
| CD19Rop_epHIV7 | (4119) | CTATTGCTTCCCGTATGGCTTTCATTTTCTCCTCCTTGTATAAATCCTGG |
| Consensus | (5301) | CTATTGCTTCCCGTATGGCTTTCATTTTCTCCTCCTTGTATAAATCCTGG |
| | | 5351                                            5400 |
| IL13(EQ)41BBZeta | (4952) | TTGCTGTCTCTTTATGAGGAGTTGTGGCCCGTTGTCAGGCAACGTGGCGT |
| CD19Rop_epHIV7 | (4169) | TTGCTGTCTCTTTATGAGGAGTTGTGGCCCGTTGTCAGGCAACGTGGCGT |
| Consensus | (5351) | TTGCTGTCTCTTTATGAGGAGTTGTGGCCCGTTGTCAGGCAACGTGGCGT |
| | | 5401                                            5450 |
| IL13(EQ)41BBZeta | (5002) | GGTGTGCACTGTGTTTGCTGACGCAACCCCCACTGGTTGGGGCATTGCCA |
| CD19Rop_epHIV7 | (4219) | GGTGTGCACTGTGTTTGCTGACGCAACCCCCACTGGTTGGGGCATTGCCA |
| Consensus | (5401) | GGTGTGCACTGTGTTTGCTGACGCAACCCCCACTGGTTGGGGCATTGCCA |
| | | 5451                                            5500 |
| IL13(EQ)41BBZeta | (5052) | CCACCTGTCAGCTCCTTTCCGGGACTTTCGCTTTCCCCCTCCCTATTGCC |
| CD19Rop_epHIV7 | (4269) | CCACCTGTCAGCTCCTTTCCGGGACTTTCGCTTTCCCCCTCCCTATTGCC |
| Consensus | (5451) | CCACCTGTCAGCTCCTTTCCGGGACTTTCGCTTTCCCCCTCCCTATTGCC |
| | | 5501                                            5550 |
| IL13(EQ)41BBZeta | (5102) | ACGGCGGAACTCATCGCCGCCTGCCTTGCCCGCTGCTGGACAGGGGCTCG |
| CD19Rop_epHIV7 | (4319) | ACGGCGGAACTCATCGCCGCCTGCCTTGCCCGCTGCTGGACAGGGGCTCG |
| Consensus | (5501) | ACGGCGGAACTCATCGCCGCCTGCCTTGCCCGCTGCTGGACAGGGGCTCG |
| | | 5551                                            5600 |
| IL13(EQ)41BBZeta | (5152) | GCTGTTGGGCACTGACAATTCCGTGGTGTTGTCGGGGAAATCATCGTCCT |
| CD19Rop_epHIV7 | (4369) | GCTGTTGGGCACTGACAATTCCGTGGTGTTGTCGGGGAAATCATCGTCCT |
| Consensus | (5551) | GCTGTTGGGCACTGACAATTCCGTGGTGTTGTCGGGGAAATCATCGTCCT |
| | | 5601                                            5650 |
| IL13(EQ)41BBZeta | (5202) | TTCCTTGGCTGCTCGCCTGTGTTGCCACCTGGATTCTGCGCGGGACGTCC |
| CD19Rop_epHIV7 | (4419) | TTCCTTGGCTGCTCGCCTGTGTTGCCACCTGGATTCTGCGCGGGACGTCC |
| Consensus | (5601) | TTCCTTGGCTGCTCGCCTGTGTTGCCACCTGGATTCTGCGCGGGACGTCC |
| | | 5651                                            5700 |
| IL13(EQ)41BBZeta | (5252) | TTCTGCTACGTCCCTTCGGCCCTCAATCCAGCGGACCTTCCTTCCCGCGG |
| CD19Rop_epHIV7 | (4469) | TTCTGCTACGTCCCTTCGGCCCTCAATCCAGCGGACCTTCCTTCCCGCGG |
| Consensus | (5651) | TTCTGCTACGTCCCTTCGGCCCTCAATCCAGCGGACCTTCCTTCCCGCGG |
| | | 5701                                            5750 |
| IL13(EQ)41BBZeta | (5302) | CCTGCTGCCGGCTCTGCGGCCTCTTCCGCGTCTTCGCCTTCGCCCTCAGA |
| CD19Rop_epHIV7 | (4519) | CCTGCTGCCGGCTCTGCGGCCTCTTCCGCGTCTTCGCCTTCGCCCTCAGA |
| Consensus | (5701) | CCTGCTGCCGGCTCTGCGGCCTCTTCCGCGTCTTCGCCTTCGCCCTCAGA |
| | | 5751                                            5800 |
| IL13(EQ)41BBZeta | (5352) | CGAGTCGGATCTCCCTTTGGGCCGCCTCCCCGCATCGATACCGTCGACTA |
| CD19Rop_epHIV7 | (4569) | CGAGTCGGATCTCCCTTTGGGCCGCCTCCCCGCATCGATACCGTCGACTA |
| Consensus | (5751) | CGAGTCGGATCTCCCTTTGGGCCGCCTCCCCGCATCGATACCGTCGACTA |
| | | 5801                                            5850 |
| IL13(EQ)41BBZeta | (5402) | GCCGTACCTTTAAGACCAATGACTTACAAGGCAGCTGTAGATCTTAGCCA |
| CD19Rop_epHIV7 | (4619) | GCCGTACCTTTAAGACCAATGACTTACAAGGCAGCTGTAGATCTTAGCCA |
| Consensus | (5801) | GCCGTACCTTTAAGACCAATGACTTACAAGGCAGCTGTAGATCTTAGCCA |
| | | 5851                                            5900 |
| IL13(EQ)41BBZeta | (5452) | CTTTTTAAAAGAAAAGGGGGGACTGGAAGGGCTAATTCACTCCCAAAGAA |
| CD19Rop_epHIV7 | (4669) | CTTTTTAAAAGAAAAGGGGGGACTGGAAGGGCTAATTCACTCCCAAAGAA |
| Consensus | (5851) | CTTTTTAAAAGAAAAGGGGGGACTGGAAGGGCTAATTCACTCCCAAAGAA |
| | | 5901                                            5950 |
| IL13(EQ)41BBZeta | (5502) | GACAAGATCTGCTTTTTGCCTGTACTGGGTCTCTCTGGTTAGACCAGATC |
| CD19Rop_epHIV7 | (4719) | GACAAGATCTGCTTTTTGCCTGTACTGGGTCTCTCTGGTTAGACCAGATC |
| Consensus | (5901) | GACAAGATCTGCTTTTTGCCTGTACTGGGTCTCTCTGGTTAGACCAGATC |
| | | 5951                                            6000 |

FIGURE 18J

```
IL13(EQ)41BBZeta   (5552)  TGAGCCTGGGAGCTCTCTGGCTAACTAGGGAACCCACTGCTTAAGCCTCA
CD19Rop_epHIV7     (4769)  TGAGCCTGGGAGCTCTCTGGCTAACTAGGGAACCCACTGCTTAAGCCTCA
       Consensus   (5951)  TGAGCCTGGGAGCTCTCTGGCTAACTAGGGAACCCACTGCTTAAGCCTCA
                           6001                                            6050
IL13(EQ)41BBZeta   (5602)  ATAAAGCTTGCCTTGAGTGCTTCAAGTAGTGTGTGCCCGTCTGTTGTGTG
CD19Rop_epHIV7     (4819)  ATAAAGCTTGCCTTGAGTGCTTCAAGTAGTGTGTGCCCGTCTGTTGTGTG
       Consensus   (6001)  ATAAAGCTTGCCTTGAGTGCTTCAAGTAGTGTGTGCCCGTCTGTTGTGTG
                           6051                                            6100
IL13(EQ)41BBZeta   (5652)  ACTCTGGTAACTAGAGATCCCTCAGACCCTTTTAGTCAGTGTGGAAAATC
CD19Rop_epHIV7     (4869)  ACTCTGGTAACTAGAGATCCCTCAGACCCTTTTAGTCAGTGTGGAAAATC
       Consensus   (6051)  ACTCTGGTAACTAGAGATCCCTCAGACCCTTTTAGTCAGTGTGGAAAATC
                           6101                                            6150
IL13(EQ)41BBZeta   (5702)  TCTAGCAGAATTCGATATCAAGCTTATCGATACCGTCGACCTCGAGGGGG
CD19Rop_epHIV7     (4919)  TCTAGCAGAATTCGATATCAAGCTTATCGATACCGTCGACCTCGAGGGGG
       Consensus   (6101)  TCTAGCAGAATTCGATATCAAGCTTATCGATACCGTCGACCTCGAGGGGG
                           6151                                            6200
IL13(EQ)41BBZeta   (5752)  GGCCCGGTACCCAATTCGCCCTATAGTGAGTCGTATTACAATTCACTGGC
CD19Rop_epHIV7     (4969)  GGCCCGGTACCCAATTCGCCCTATAGTGAGTCGTATTACAATTCACTGGC
       Consensus   (6151)  GGCCCGGTACCCAATTCGCCCTATAGTGAGTCGTATTACAATTCACTGGC
                           6201                                            6250
IL13(EQ)41BBZeta   (5802)  CGTCGTTTTACAACGTCGTGACTGGGAAAACCCTGGCGTTACCCAACTTA
CD19Rop_epHIV7     (5019)  CGTCGTTTTACAACGTCGTGACTGGGAAAACCCTGGCGTTACCCAACTTA
       Consensus   (6201)  CGTCGTTTTACAACGTCGTGACTGGGAAAACCCTGGCGTTACCCAACTTA
                           6251                                            6300
IL13(EQ)41BBZeta   (5852)  ATCGCCTTGCAGCACATCCCCCTTTCGCCAGCTGGCGTAATAGCGAAGAG
CD19Rop_epHIV7     (5069)  ATCGCCTTGCAGCACATCCCCCTTTCGCCAGCTGGCGTAATAGCGAAGAG
       Consensus   (6251)  ATCGCCTTGCAGCACATCCCCCTTTCGCCAGCTGGCGTAATAGCGAAGAG
                           6301                                            6350
IL13(EQ)41BBZeta   (5902)  GCCCGCACCGATCGCCCTTCCCAACAGTTGCGCAGCCTGAATGGCGAATG
CD19Rop_epHIV7     (5119)  GCCCGCACCGATCGCCCTTCCCAACAGTTGCGCAGCCTGAATGGCGAATG
       Consensus   (6301)  GCCCGCACCGATCGCCCTTCCCAACAGTTGCGCAGCCTGAATGGCGAATG
                           6351                                            6400
IL13(EQ)41BBZeta   (5952)  GAAATTGTAAGCGTTAATATTTTGTTAAAATTCGCGTTAAATTTTTGTTA
CD19Rop_epHIV7     (5169)  GAAATTGTAAGCGTTAATATTTTGTTAAAATTCGCGTTAAATTTTTGTTA
       Consensus   (6351)  GAAATTGTAAGCGTTAATATTTTGTTAAAATTCGCGTTAAATTTTTGTTA
                           6401                                            6450
IL13(EQ)41BBZeta   (6002)  AATCAGCTCATTTTTTAACCAATAGGCCGAAATCGGCAAAATCCCTTATA
CD19Rop_epHIV7     (5219)  AATCAGCTCATTTTTTAACCAATAGGCCGAAATCGGCAAAATCCCTTATA
       Consensus   (6401)  AATCAGCTCATTTTTTAACCAATAGGCCGAAATCGGCAAAATCCCTTATA
                           6451                                            6500
IL13(EQ)41BBZeta   (6052)  AATCAAAAGAATAGACCGAGATAGGGTTGAGTGTTGTTCCAGTTTGGAAC
CD19Rop_epHIV7     (5269)  AATCAAAAGAATAGACCGAGATAGGGTTGAGTGTTGTTCCAGTTTGGAAC
       Consensus   (6451)  AATCAAAAGAATAGACCGAGATAGGGTTGAGTGTTGTTCCAGTTTGGAAC
                           6501                                            6550
IL13(EQ)41BBZeta   (6102)  AAGAGTCCACTATTAAAGAACGTGGACTCCAACGTCAAAGGGCGAAAAAC
CD19Rop_epHIV7     (5319)  AAGAGTCCACTATTAAAGAACGTGGACTCCAACGTCAAAGGGCGAAAAAC
       Consensus   (6501)  AAGAGTCCACTATTAAAGAACGTGGACTCCAACGTCAAAGGGCGAAAAAC
                           6551                                            6600
IL13(EQ)41BBZeta   (6152)  CGTCTATCAGGGCGATGGCCCACTACGTGAACCATCACCCTAATCAAGTT
CD19Rop_epHIV7     (5369)  CGTCTATCAGGGCGATGGCCCACTACGTGAACCATCACCCTAATCAAGTT
       Consensus   (6551)  CGTCTATCAGGGCGATGGCCCACTACGTGAACCATCACCCTAATCAAGTT
                           6601                                            6650
IL13(EQ)41BBZeta   (6202)  TTTTGGGGTCGAGGTGCCGTAAAGCACTAAATCGGAACCCTAAAGGGAGC
CD19Rop_epHIV7     (5419)  TTTTGGGGTCGAGGTGCCGTAAAGCACTAAATCGGAACCCTAAAGGGAGC
       Consensus   (6601)  TTTTGGGGTCGAGGTGCCGTAAAGCACTAAATCGGAACCCTAAAGGGAGC
```

FIGURE 18K

```
                              6651                                          6700
IL13(EQ)41BBZeta    (6252) CCCCGATTTAGAGCTTGACGGGGAAAGCCGGCGAACGTGGCGAGAAAGGA
CD19Rop_epHIV7      (5469) CCCCGATTTAGAGCTTGACGGGGAAAGCCGGCGAACGTGGCGAGAAAGGA
      Consensus     (6651) CCCCGATTTAGAGCTTGACGGGGAAAGCCGGCGAACGTGGCGAGAAAGGA
                              6701                                          6750
IL13(EQ)41BBZeta    (6302) AGGGAAGAAAGCGAAAGGAGCGGGCGCTAGGGCGCTGGCAAGTGTAGCGG
CD19Rop_epHIV7      (5519) AGGGAAGAAAGCGAAAGGAGCGGGCGCTAGGGCGCTGGCAAGTGTAGCGG
      Consensus     (6701) AGGGAAGAAAGCGAAAGGAGCGGGCGCTAGGGCGCTGGCAAGTGTAGCGG
                              6751                                          6800
IL13(EQ)41BBZeta    (6352) TCACGCTGCGCGTAACCACCACACCCGCCGCGCTTAATGCGCCGCTACAG
CD19Rop_epHIV7      (5569) TCACGCTGCGCGTAACCACCACACCCGCCGCGCTTAATGCGCCGCTACAG
      Consensus     (6751) TCACGCTGCGCGTAACCACCACACCCGCCGCGCTTAATGCGCCGCTACAG
                              6801                                          6850
IL13(EQ)41BBZeta    (6402) GGCGCGTCAGGTGGCACTTTTCGGGGAAATGTGCGCGGAACCCCTATTTG
CD19Rop_epHIV7      (5619) GGCGCGTCAGGTGGCACTTTTCGGGGAAATGTGCGCGGAACCCCTATTTG
      Consensus     (6801) GGCGCGTCAGGTGGCACTTTTCGGGGAAATGTGCGCGGAACCCCTATTTG
                              6851                                          6900
IL13(EQ)41BBZeta    (6452) TTTATTTTTCTAAATACATTCAAATATGTATCCGCTCATGAGACAATAAC
CD19Rop_epHIV7      (5669) TTTATTTTTCTAAATACATTCAAATATGTATCCGCTCATGAGACAATAAC
      Consensus     (6851) TTTATTTTTCTAAATACATTCAAATATGTATCCGCTCATGAGACAATAAC
                              6901                                          6950
IL13(EQ)41BBZeta    (6502) CCTGATAAATGCTTCAATAATATTGAAAAAGGAAGAGTATGAGTATTCAA
CD19Rop_epHIV7      (5719) CCTGATAAATGCTTCAATAATATTGAAAAAGGAAGAGTATGAGTATTCAA
      Consensus     (6901) CCTGATAAATGCTTCAATAATATTGAAAAAGGAAGAGTATGAGTATTCAA
                              6951                                          7000
IL13(EQ)41BBZeta    (6552) CATTTCCGTGTCGCCCTTATTCCCTTTTTTGCGGCATTTTGCCTTCCTGT
CD19Rop_epHIV7      (5769) CATTTCCGTGTCGCCCTTATTCCCTTTTTTGCGGCATTTTGCCTTCCTGT
      Consensus     (6951) CATTTCCGTGTCGCCCTTATTCCCTTTTTTGCGGCATTTTGCCTTCCTGT
                              7001                                          7050
IL13(EQ)41BBZeta    (6602) TTTTGCTCACCCAGAAACGCTGGTGAAAGTAAAAGATGCTGAAGATCAGT
CD19Rop_epHIV7      (5819) TTTTGCTCACCCAGAAACGCTGGTGAAAGTAAAAGATGCTGAAGATCAGT
      Consensus     (7001) TTTTGCTCACCCAGAAACGCTGGTGAAAGTAAAAGATGCTGAAGATCAGT
                              7051                                          7100
IL13(EQ)41BBZeta    (6652) TGGGTGCACGAGTGGGTTACATCGAACTGGATCTCAACAGCGGTAAGATC
CD19Rop_epHIV7      (5869) TGGGTGCACGAGTGGGTTACATCGAACTGGATCTCAACAGCGGTAAGATC
      Consensus     (7051) TGGGTGCACGAGTGGGTTACATCGAACTGGATCTCAACAGCGGTAAGATC
                              7101                                          7150
IL13(EQ)41BBZeta    (6702) CTTGAGAGTTTTCGCCCCGAAGAACGTTTTCCAATGATGAGCACTTTTAA
CD19Rop_epHIV7      (5919) CTTGAGAGTTTTCGCCCCGAAGAACGTTTTCCAATGATGAGCACTTTTAA
      Consensus     (7101) CTTGAGAGTTTTCGCCCCGAAGAACGTTTTCCAATGATGAGCACTTTTAA
                              7151                                          7200
IL13(EQ)41BBZeta    (6752) AGTTCTGCTATGTGGCGCGGTATTATCCCGTATTGACGCCGGGCAAGAGC
CD19Rop_epHIV7      (5969) AGTTCTGCTATGTGGCGCGGTATTATCCCGTATTGACGCCGGGCAAGAGC
      Consensus     (7151) AGTTCTGCTATGTGGCGCGGTATTATCCCGTATTGACGCCGGGCAAGAGC
                              7201                                          7250
IL13(EQ)41BBZeta    (6802) AACTCGGTCGCCGCATACACTATTCTCAGAATGACTTGGTTGAGTACTCA
CD19Rop_epHIV7      (6019) AACTCGGTCGCCGCATACACTATTCTCAGAATGACTTGGTTGAGTACTCA
      Consensus     (7201) AACTCGGTCGCCGCATACACTATTCTCAGAATGACTTGGTTGAGTACTCA
                              7251                                          7300
IL13(EQ)41BBZeta    (6852) CCAGTCACAGAAAAGCATCTTACGGATGGCATGACAGTAAGAGAATTATG
CD19Rop_epHIV7      (6069) CCAGTCACAGAAAAGCATCTTACGGATGGCATGACAGTAAGAGAATTATG
      Consensus     (7251) CCAGTCACAGAAAAGCATCTTACGGATGGCATGACAGTAAGAGAATTATG
                              7301                                          7350
IL13(EQ)41BBZeta    (6902) CAGTGCTGCCATAACCATGAGTGATAACACTGCGGCCAACTTACTTCTGA
CD19Rop_epHIV7      (6119) CAGTGCTGCCATAACCATGAGTGATAACACTGCGGCCAACTTACTTCTGA
```

FIGURE 18L

```
       Consensus  (7301)  CAGTGCTGCCATAACCATGAGTGATAACACTGCGGCCAACTTACTTCTGA
                          7351                                              7400
IL13(EQ)41BBZeta  (6952)  CAACGATCGGAGGACCGAAGGAGCTAACCGCTTTTTGCACAACATGGGG
   CD19Rop_epHIV7 (6169)  CAACGATCGGAGGACCGAAGGAGCTAACCGCTTTTTGCACAACATGGGG
       Consensus  (7351)  CAACGATCGGAGGACCGAAGGAGCTAACCGCTTTTTGCACAACATGGGG
                          7401                                              7450
IL13(EQ)41BBZeta  (7002)  GATCATGTAACTCGCCTTGATCGTTGGGAACCGGAGCTGAATGAAGCCAT
   CD19Rop_epHIV7 (6219)  GATCATGTAACTCGCCTTGATCGTTGGGAACCGGAGCTGAATGAAGCCAT
       Consensus  (7401)  GATCATGTAACTCGCCTTGATCGTTGGGAACCGGAGCTGAATGAAGCCAT
                          7451                                              7500
IL13(EQ)41BBZeta  (7052)  ACCAAACGACGAGCGTGACACCACGATGCCTGTAGCAATGGCAACAACGT
   CD19Rop_epHIV7 (6269)  ACCAAACGACGAGCGTGACACCACGATGCCTGTAGCAATGGCAACAACGT
       Consensus  (7451)  ACCAAACGACGAGCGTGACACCACGATGCCTGTAGCAATGGCAACAACGT
                          7501                                              7550
IL13(EQ)41BBZeta  (7102)  TGCGCAAACTATTAACTGGCGAACTACTTACTCTAGCTTCCCGGCAACAA
   CD19Rop_epHIV7 (6319)  TGCGCAAACTATTAACTGGCGAACTACTTACTCTAGCTTCCCGGCAACAA
       Consensus  (7501)  TGCGCAAACTATTAACTGGCGAACTACTTACTCTAGCTTCCCGGCAACAA
                          7551                                              7600
IL13(EQ)41BBZeta  (7152)  TTAATAGACTGGATGGAGGCGGATAAAGTTGCAGGACCACTTCTGCGCTC
   CD19Rop_epHIV7 (6369)  TTAATAGACTGGATGGAGGCGGATAAAGTTGCAGGACCACTTCTGCGCTC
       Consensus  (7551)  TTAATAGACTGGATGGAGGCGGATAAAGTTGCAGGACCACTTCTGCGCTC
                          7601                                              7650
IL13(EQ)41BBZeta  (7202)  GGCCCTTCCGGCTGGCTGGTTTATTGCTGATAAATCTGGAGCCGGTGAGC
   CD19Rop_epHIV7 (6419)  GGCCCTTCCGGCTGGCTGGTTTATTGCTGATAAATCTGGAGCCGGTGAGC
       Consensus  (7601)  GGCCCTTCCGGCTGGCTGGTTTATTGCTGATAAATCTGGAGCCGGTGAGC
                          7651                                              7700
IL13(EQ)41BBZeta  (7252)  GTGGGTCTCGCGGTATCATTGCAGCACTGGGGCCAGATGGTAAGCCCTCC
   CD19Rop_epHIV7 (6469)  GTGGGTCTCGCGGTATCATTGCAGCACTGGGGCCAGATGGTAAGCCCTCC
       Consensus  (7651)  GTGGGTCTCGCGGTATCATTGCAGCACTGGGGCCAGATGGTAAGCCCTCC
                          7701                                              7750
IL13(EQ)41BBZeta  (7302)  CGTATCGTAGTTATCTACACGACGGGGAGTCAGGCAACTATGGATGAACG
   CD19Rop_epHIV7 (6519)  CGTATCGTAGTTATCTACACGACGGGGAGTCAGGCAACTATGGATGAACG
       Consensus  (7701)  CGTATCGTAGTTATCTACACGACGGGGAGTCAGGCAACTATGGATGAACG
                          7751                                              7800
IL13(EQ)41BBZeta  (7352)  AAATAGACAGATCGCTGAGATAGGTGCCTCACTGATTAAGCATTGGTAAC
   CD19Rop_epHIV7 (6569)  AAATAGACAGATCGCTGAGATAGGTGCCTCACTGATTAAGCATTGGTAAC
       Consensus  (7751)  AAATAGACAGATCGCTGAGATAGGTGCCTCACTGATTAAGCATTGGTAAC
                          7801                                              7850
IL13(EQ)41BBZeta  (7402)  TGTCAGACCAAGTTTACTCATATATACTTTAGATTGATTTAAAACTTCAT
   CD19Rop_epHIV7 (6619)  TGTCAGACCAAGTTTACTCATATATACTTTAGATTGATTTAAAACTTCAT
       Consensus  (7801)  TGTCAGACCAAGTTTACTCATATATACTTTAGATTGATTTAAAACTTCAT
                          7851                                              7900
IL13(EQ)41BBZeta  (7452)  TTTTAATTTAAAAGGATCTAGGTGAAGATCCTTTTTGATAATCTCATGAC
   CD19Rop_epHIV7 (6669)  TTTTAATTTAAAAGGATCTAGGTGAAGATCCTTTTTGATAATCTCATGAC
       Consensus  (7851)  TTTTAATTTAAAAGGATCTAGGTGAAGATCCTTTTTGATAATCTCATGAC
                          7901                                              7950
IL13(EQ)41BBZeta  (7502)  CAAAATCCCTTAACGTGAGTTTTCGTTCCACTGAGCGTCAGACCCCGTAG
   CD19Rop_epHIV7 (6719)  CAAAATCCCTTAACGTGAGTTTTCGTTCCACTGAGCGTCAGACCCCGTAG
       Consensus  (7901)  CAAAATCCCTTAACGTGAGTTTTCGTTCCACTGAGCGTCAGACCCCGTAG
                          7951                                              8000
IL13(EQ)41BBZeta  (7552)  AAAGATCAAAGGATCTTCTTGAGATCCTTTTTTTCTGCGCGTAATCTGC
   CD19Rop_epHIV7 (6769)  AAAGATCAAAGGATCTTCTTGAGATCCTTTTTTTCTGCGCGTAATCTGC
       Consensus  (7951)  AAAGATCAAAGGATCTTCTTGAGATCCTTTTTTTCTGCGCGTAATCTGC
                          8001                                              8050
IL13(EQ)41BBZeta  (7602)  TGCTTGCAAACAAAAAAACCACCGCTACCAGCGGTGGTTTGTTTGCCGGA
```

FIGURE 18M

```
CD19Rop_epHIV7    (6819) TGCTTGCAAACAAAAAAACCACCGCTACCAGCGGTGGTTTGTTTGCCGGA
       Consensus  (8001) TGCTTGCAAACAAAAAAACCACCGCTACCAGCGGTGGTTTGTTTGCCGGA
                         8051                                            8100
IL13(EQ)41BBZeta  (7652) TCAAGAGCTACCAACTCTTTTTCCGAAGGTAACTGGCTTCAGCAGAGCGC
CD19Rop_epHIV7    (6869) TCAAGAGCTACCAACTCTTTTTCCGAAGGTAACTGGCTTCAGCAGAGCGC
       Consensus  (8051) TCAAGAGCTACCAACTCTTTTTCCGAAGGTAACTGGCTTCAGCAGAGCGC
                         8101                                            8150
IL13(EQ)41BBZeta  (7702) AGATACCAAATACTGTTCTTCTAGTGTAGCCGTAGTTAGGCCACCACTTC
CD19Rop_epHIV7    (6919) AGATACCAAATACTGTTCTTCTAGTGTAGCCGTAGTTAGGCCACCACTTC
       Consensus  (8101) AGATACCAAATACTGTTCTTCTAGTGTAGCCGTAGTTAGGCCACCACTTC
                         8151                                            8200
IL13(EQ)41BBZeta  (7752) AAGAACTCTGTAGCACCGCCTACATACCTCGCTCTGCTAATCCTGTTACC
CD19Rop_epHIV7    (6969) AAGAACTCTGTAGCACCGCCTACATACCTCGCTCTGCTAATCCTGTTACC
       Consensus  (8151) AAGAACTCTGTAGCACCGCCTACATACCTCGCTCTGCTAATCCTGTTACC
                         8201                                            8250
IL13(EQ)41BBZeta  (7802) AGTGGCTGCTGCCAGTGGCGATAAGTCGTGTCTTACCGGGTTGGACTCAA
CD19Rop_epHIV7    (7019) AGTGGCTGCTGCCAGTGGCGATAAGTCGTGTCTTACCGGGTTGGACTCAA
       Consensus  (8201) AGTGGCTGCTGCCAGTGGCGATAAGTCGTGTCTTACCGGGTTGGACTCAA
                         8251                                            8300
IL13(EQ)41BBZeta  (7852) GACGATAGTTACCGGATAAGGCGCAGCGGTCGGGCTGAACGGGGGGTTCG
CD19Rop_epHIV7    (7069) GACGATAGTTACCGGATAAGGCGCAGCGGTCGGGCTGAACGGGGGGTTCG
       Consensus  (8251) GACGATAGTTACCGGATAAGGCGCAGCGGTCGGGCTGAACGGGGGGTTCG
                         8301                                            8350
IL13(EQ)41BBZeta  (7902) TGCACACAGCCCAGCTTGGAGCGAACGACCTACACCGAACTGAGATACCT
CD19Rop_epHIV7    (7119) TGCACACAGCCCAGCTTGGAGCGAACGACCTACACCGAACTGAGATACCT
       Consensus  (8301) TGCACACAGCCCAGCTTGGAGCGAACGACCTACACCGAACTGAGATACCT
                         8351                                            8400
IL13(EQ)41BBZeta  (7952) ACAGCGTGAGCTATGAGAAAGCGCCACGCTTCCCGAAGGGAGAAAGGCGG
CD19Rop_epHIV7    (7169) ACAGCGTGAGCTATGAGAAAGCGCCACGCTTCCCGAAGGGAGAAAGGCGG
       Consensus  (8351) ACAGCGTGAGCTATGAGAAAGCGCCACGCTTCCCGAAGGGAGAAAGGCGG
                         8401                                            8450
IL13(EQ)41BBZeta  (8002) ACAGGTATCCGGTAAGCGGCAGGGTCGGAACAGGAGAGCGCACGAGGGAG
CD19Rop_epHIV7    (7219) ACAGGTATCCGGTAAGCGGCAGGGTCGGAACAGGAGAGCGCACGAGGGAG
       Consensus  (8401) ACAGGTATCCGGTAAGCGGCAGGGTCGGAACAGGAGAGCGCACGAGGGAG
                         8451                                            8500
IL13(EQ)41BBZeta  (8052) CTTCCAGGGGGAAACGCCTGGTATCTTTATAGTCCTGTCGGGTTTCGCCA
CD19Rop_epHIV7    (7269) CTTCCAGGGGGAAACGCCTGGTATCTTTATAGTCCTGTCGGGTTTCGCCA
       Consensus  (8451) CTTCCAGGGGGAAACGCCTGGTATCTTTATAGTCCTGTCGGGTTTCGCCA
                         8501                                            8550
IL13(EQ)41BBZeta  (8102) CCTCTGACTTGAGCGTCGATTTTTGTGATGCTCGTCAGGGGGGCGGAGCC
CD19Rop_epHIV7    (7319) CCTCTGACTTGAGCGTCGATTTTTGTGATGCTCGTCAGGGGGGCGGAGCC
       Consensus  (8501) CCTCTGACTTGAGCGTCGATTTTTGTGATGCTCGTCAGGGGGGCGGAGCC
                         8551                                            8600
IL13(EQ)41BBZeta  (8152) TATGGAAAAACGCCAGCAACGCGGCCTTTTTACGGTTCCTGGCCTTTTGC
CD19Rop_epHIV7    (7369) TATGGAAAAACGCCAGCAACGCGGCCTTTTTACGGTTCCTGGCCTTTTGC
       Consensus  (8551) TATGGAAAAACGCCAGCAACGCGGCCTTTTTACGGTTCCTGGCCTTTTGC
                         8601                                            8650
IL13(EQ)41BBZeta  (8202) TGGCCTTTTGCTCACATGTTCTTTCCTGCGTTATCCCCTGATTCTGTGGA
CD19Rop_epHIV7    (7419) TGGCCTTTTGCTCACATGTTCTTTCCTGCGTTATCCCCTGATTCTGTGGA
       Consensus  (8601) TGGCCTTTTGCTCACATGTTCTTTCCTGCGTTATCCCCTGATTCTGTGGA
                         8651                                            8700
IL13(EQ)41BBZeta  (8252) TAACCGTATTACCGCCTTTGAGTGAGCTGATACCGCTCGCCGCAGCCGAA
CD19Rop_epHIV7    (7469) TAACCGTATTACCGCCTTTGAGTGAGCTGATACCGCTCGCCGCAGCCGAA
       Consensus  (8651) TAACCGTATTACCGCCTTTGAGTGAGCTGATACCGCTCGCCGCAGCCGAA
                         8701                                            8750
```

FIGURE 18N

```
IL13(EQ)41BBZeta  (8302)  CGACCGAGCGCAGCGAGTCAGTGAGCGAGGAAGCGGAAGAGCGCCCAATA
CD19Rop_epHIV7    (7519)  CGACCGAGCGCAGCGAGTCAGTGAGCGAGGAAGCGGAAGAGCGCCCAATA
    Consensus     (8701)  CGACCGAGCGCAGCGAGTCAGTGAGCGAGGAAGCGGAAGAGCGCCCAATA
                          8751                                              8800
IL13(EQ)41BBZeta  (8352)  CGCAAACCGCCTCTCCCCGCGCGTTGGCCGATTCATTAATGCAGCTGGCA
CD19Rop_epHIV7    (7569)  CGCAAACCGCCTCTCCCCGCGCGTTGGCCGATTCATTAATGCAGCTGGCA
    Consensus     (8751)  CGCAAACCGCCTCTCCCCGCGCGTTGGCCGATTCATTAATGCAGCTGGCA
                          8801                                              8850
IL13(EQ)41BBZeta  (8402)  CGACAGGTTTCCCGACTGGAAAGCGGGCAGTGAGCGCAACGCAATTAATG
CD19Rop_epHIV7    (7619)  CGACAGGTTTCCCGACTGGAAAGCGGGCAGTGAGCGCAACGCAATTAATG
    Consensus     (8801)  CGACAGGTTTCCCGACTGGAAAGCGGGCAGTGAGCGCAACGCAATTAATG
                          8851                                              8900
IL13(EQ)41BBZeta  (8452)  TGAGTTAGCTCACTCATTAGGCACCCCAGGCTTTACACTTTATGCTTCCG
CD19Rop_epHIV7    (7669)  TGAGTTAGCTCACTCATTAGGCACCCCAGGCTTTACACTTTATGCTTCCG
    Consensus     (8851)  TGAGTTAGCTCACTCATTAGGCACCCCAGGCTTTACACTTTATGCTTCCG
                          8901                                              8950
IL13(EQ)41BBZeta  (8502)  GCTCGTATGTTGTGTGGAATTGTGAGCGGATAACAATTTCACACAGGAAA
CD19Rop_epHIV7    (7719)  GCTCGTATGTTGTGTGGAATTGTGAGCGGATAACAATTTCACACAGGAAA
    Consensus     (8901)  GCTCGTATGTTGTGTGGAATTGTGAGCGGATAACAATTTCACACAGGAAA
                          8951                                              9000
IL13(EQ)41BBZeta  (8552)  CAGCTATGACCATGATTACGCCAAGCTCGAAATTAACCCTCACTAAAGGG
CD19Rop_epHIV7    (7769)  CAGCTATGACCATGATTACGCCAAGCTCGAAATTAACCCTCACTAAAGGG
    Consensus     (8951)  CAGCTATGACCATGATTACGCCAAGCTCGAAATTAACCCTCACTAAAGGG
                          9001                                              9050
IL13(EQ)41BBZeta  (8602)  AACAAAAGCTGGAGCTCCACCGCGGTGGCGGCCTCGAGGTCGAGATCCGG
CD19Rop_epHIV7    (7819)  AACAAAAGCTGGAGCTCCACCGCGGTGGCGGCCTCGAGGTCGAGATCCGG
    Consensus     (9001)  AACAAAAGCTGGAGCTCCACCGCGGTGGCGGCCTCGAGGTCGAGATCCGG
                          9051                                              9100
IL13(EQ)41BBZeta  (8652)  TCGACCAGCAACCATAGTCCCGCCCCTAACTCCGCCCATCCCGCCCCTAA
CD19Rop_epHIV7    (7869)  TCGACCAGCAACCATAGTCCCGCCCCTAACTCCGCCCATCCCGCCCCTAA
    Consensus     (9051)  TCGACCAGCAACCATAGTCCCGCCCCTAACTCCGCCCATCCCGCCCCTAA
                          9101                                              9150
IL13(EQ)41BBZeta  (8702)  CTCCGCCCAGTTCCGCCCATTCTCCGCCCCATGGCTGACTAATTTTTTTT
CD19Rop_epHIV7    (7919)  CTCCGCCCAGTTCCGCCCATTCTCCGCCCCATGGCTGACTAATTTTTTTT
    Consensus     (9101)  CTCCGCCCAGTTCCGCCCATTCTCCGCCCCATGGCTGACTAATTTTTTTT
                          9151                                              9200
IL13(EQ)41BBZeta  (8752)  ATTTATGCAGAGGCCGAGGCCGCCTCGGCCTCTGAGCTATTCCAGAAGTA
CD19Rop_epHIV7    (7969)  ATTTATGCAGAGGCCGAGGCCGCCTCGGCCTCTGAGCTATTCCAGAAGTA
    Consensus     (9151)  ATTTATGCAGAGGCCGAGGCCGCCTCGGCCTCTGAGCTATTCCAGAAGTA
                          9201                                              9250
IL13(EQ)41BBZeta  (8802)  GTGAGGAGGCTTTTTTGGAGGCCTAGGCTTTTGCAAAAAGCTTCGACGGT
CD19Rop_epHIV7    (8019)  GTGAGGAGGCTTTTTTGGAGGCCTAGGCTTTTGCAAAAAGCTTCGACGGT
    Consensus     (9201)  GTGAGGAGGCTTTTTTGGAGGCCTAGGCTTTTGCAAAAAGCTTCGACGGT
                          9251                                              9300
IL13(EQ)41BBZeta  (8852)  ATCGATTGGCTCATGTCCAACATTACCGCCATGTTGACATTGATTATTGA
CD19Rop_epHIV7    (8069)  ATCGATTGGCTCATGTCCAACATTACCGCCATGTTGACATTGATTATTGA
    Consensus     (9251)  ATCGATTGGCTCATGTCCAACATTACCGCCATGTTGACATTGATTATTGA
                          9301                                              9350
IL13(EQ)41BBZeta  (8902)  CTAGTTATTAATAGTAATCAATTACGGGGTCATTAGTTCATAGCCCATAT
CD19Rop_epHIV7    (8119)  CTAGTTATTAATAGTAATCAATTACGGGGTCATTAGTTCATAGCCCATAT
    Consensus     (9301)  CTAGTTATTAATAGTAATCAATTACGGGGTCATTAGTTCATAGCCCATAT
                          9351                                              9400
IL13(EQ)41BBZeta  (8952)  ATGGAGTTCCGCGTTACATAACTTACGGTAAATGGCCCGCCTGGCTGACC
CD19Rop_epHIV7    (8169)  ATGGAGTTCCGCGTTACATAACTTACGGTAAATGGCCCGCCTGGCTGACC
    Consensus     (9351)  ATGGAGTTCCGCGTTACATAACTTACGGTAAATGGCCCGCCTGGCTGACC
```

FIGURE 180

```
                          9401                                              9450
IL13(EQ)41BBZeta   (9002) GCCCAACGACCCCCGCCCATTGACGTCAATAATGACGTATGTTCCCATAG
CD19Rop_epHIV7     (8219) GCCCAACGACCCCCGCCCATTGACGTCAATAATGACGTATGTTCCCATAG
      Consensus    (9401) GCCCAACGACCCCCGCCCATTGACGTCAATAATGACGTATGTTCCCATAG
                          9451                                              9500
IL13(EQ)41BBZeta   (9052) TAACGCCAATAGGGACTTTCCATTGACGTCAATGGGTGGAGTATTTACGG
CD19Rop_epHIV7     (8269) TAACGCCAATAGGGACTTTCCATTGACGTCAATGGGTGGAGTATTTACGG
      Consensus    (9451) TAACGCCAATAGGGACTTTCCATTGACGTCAATGGGTGGAGTATTTACGG
                          9501                                              9550
IL13(EQ)41BBZeta   (9102) TAAACTGCCCACTTGGCAGTACATCAAGTGTATCATATGCCAAGTACGCC
CD19Rop_epHIV7     (8319) TAAACTGCCCACTTGGCAGTACATCAAGTGTATCATATGCCAAGTACGCC
      Consensus    (9501) TAAACTGCCCACTTGGCAGTACATCAAGTGTATCATATGCCAAGTACGCC
                          9551                                              9600
IL13(EQ)41BBZeta   (9152) CCCTATTGACGTCAATGACGGTAAATGGCCCGCCTGGCATTATGCCCAGT
CD19Rop_epHIV7     (8369) CCCTATTGACGTCAATGACGGTAAATGGCCCGCCTGGCATTATGCCCAGT
      Consensus    (9551) CCCTATTGACGTCAATGACGGTAAATGGCCCGCCTGGCATTATGCCCAGT
                          9601                                              9650
IL13(EQ)41BBZeta   (9202) ACATGACCTTATGGGACTTTCCTACTTGGCAGTACATCTACGTATTAGTC
CD19Rop_epHIV7     (8419) ACATGACCTTATGGGACTTTCCTACTTGGCAGTACATCTACGTATTAGTC
      Consensus    (9601) ACATGACCTTATGGGACTTTCCTACTTGGCAGTACATCTACGTATTAGTC
                          9651                                              9700
IL13(EQ)41BBZeta   (9252) ATCGCTATTACCATGGTGATGCGGTTTTGGCAGTACATCAATGGGCGTGG
CD19Rop_epHIV7     (8469) ATCGCTATTACCATGGTGATGCGGTTTTGGCAGTACATCAATGGGCGTGG
      Consensus    (9651) ATCGCTATTACCATGGTGATGCGGTTTTGGCAGTACATCAATGGGCGTGG
                          9701                                              9750
IL13(EQ)41BBZeta   (9302) ATAGCGGTTTGACTCACGGGGATTTCCAAGTCTCCACCCCATTGACGTCA
CD19Rop_epHIV7     (8519) ATAGCGGTTTGACTCACGGGGATTTCCAAGTCTCCACCCCATTGACGTCA
      Consensus    (9701) ATAGCGGTTTGACTCACGGGGATTTCCAAGTCTCCACCCCATTGACGTCA
                          9751                                              9800
IL13(EQ)41BBZeta   (9352) ATGGGAGTTTGTTTTGGCACCAAAATCAACGGGACTTTCCAAAATGTCGT
CD19Rop_epHIV7     (8569) ATGGGAGTTTGTTTTGGCACCAAAATCAACGGGACTTTCCAAAATGTCGT
      Consensus    (9751) ATGGGAGTTTGTTTTGGCACCAAAATCAACGGGACTTTCCAAAATGTCGT
                          9801                                              9850
IL13(EQ)41BBZeta   (9402) AACAACTCCGCCCCATTGACGCAAATGGGCGGTAGGCGTGTACGGAATTC
CD19Rop_epHIV7     (8619) AACAACTCCGCCCCATTGACGCAAATGGGCGGTAGGCGTGTACGGAATTC
      Consensus    (9801) AACAACTCCGCCCCATTGACGCAAATGGGCGGTAGGCGTGTACGGAATTC
                          9851                                              9900
IL13(EQ)41BBZeta   (9452) GGAGTGGCGAGCCCTCAGATCCTGCATATAAGCAGCTGCTTTTTGCCTGT
CD19Rop_epHIV7     (8669) GGAGTGGCGAGCCCTCAGATCCTGCATATAAGCAGCTGCTTTTTGCCTGT
      Consensus    (9851) GGAGTGGCGAGCCCTCAGATCCTGCATATAAGCAGCTGCTTTTTGCCTGT
                          9901      9914
IL13(EQ)41BBZeta   (9502) ACTGGGTCTCTCTG
CD19Rop_epHIV7     (8719) ACTGGGTCTCTCTG
      Consensus    (9901) ACTGGGTCTCTCTG
```

FIGURE 19

IL13(EmY)-CD8h3-CD8tm2-41BB-Zeta

<u>MLLLVTSLLLCELPHPAFLLIP</u>GPVPPSTALRLIEELVNITQNQKAPLCNGSMVWSINLTAGM GMCSFRa signal peptide      IL13(EmY)

YCAALESLINVSGCSAIEKTQRMLSGFCPHKVSAGQFSSLHVRDTKIEVAQFVKDLLLHLKKLF

REGRFN<u>AKPTTTPAPRPPTPAPTIASQPLSLRPEACRPAAGGAVHTRGLDFACDIYIWAPLAG</u>

CD8hinge (48 aa)                                        CD8tm(2)

<u>TCGVLLLSLVITLY</u><u>KRGRKKLLYIFKQPFMRPVQTTQEEDGCSCRFPEEEEGGCEL</u>GGG<u>RVKFS</u>

4-1BB cyto                                  CD3ζ

<u>RSADAPAYQQGQNQLYNELNLGRREEYDVLDKRRGRDPEMGGKPRRKNPQEGLYNELQK</u>

<u>DKMAEAYSEIGMKGERRRGKGHDGLYQGLSTATKDTYDALHMQALPPR</u>

GMCSFRa signal peptide
IL13(EmY)
CD8hinge
CD8 transmembrane (2)
4-1BB cyto
(Gly)3
Zeta

FIGURE 20

IL13(EmY)-CD8h3-CD28tm-CD28gg-41BB-Zeta

<u>MLLLVTSLLLCELPHPAFLLIP</u>GPVPPSTALRLIEELVNITQNQKAPLCNGSMVWSINLTAGM GMCSFRa signal peptide       IL13(EmY)

YCAALESLINVSGCSAIEKTQRMLSGFCPHKVSAGQFSSLHVRDTKIEVAQFVKDLLLHLKKLF

REGRFN<u>AKPTTTPAPRPPTPAPTIASQPLSLRPEACRPAAGGAVHTRGLDFACDFWVLVVVG</u>

CD8 hinge (48 aa)                                CD28tm

GVLACYSLLVTVAFIIFWV<u>RSKRSRGGHSDYMNMTPRRPGPTRKHYQPYAPPRDFAAYRSG</u>

CD28gg

GGK<u>RGRKKLLYIFKQPFMRPVQTTQEEDGCSCRFPEEEEGGCEL</u>GGG<u>RVKFSRSADAPAYQ</u>

4-1BB cyto                                        CD3ζ

<u>QGQNQLYNELNLGRREEYDVLDKRRGRDPEMGGKPRRKNPQEGLYNELQKDKMAEAYSEI</u>

<u>GMKGERRRGKGHDGLYQGLSTATKDTYDALHMQALPPR</u>

GMCSFRa signal peptide
IL13(EmY)
CD8hinge
CD28 transmembrane
CD28gg
4-1BB cyto
(Gly)3
Zeta

FIGURE 21

IL13(EmY)-IgG4(HL-CH3)-CD4tm-41BB-Zeta

<u>MLLLVTSLLLCELPHPAFLLIP</u><u>GPVPPSTALR</u><u>LIEELVNITQNQKAPLCNGSMVWSINLTAGM</u>
　GMCSFRa signal peptide　　　　　IL13(EmY)

<u>YCAALESLINVSGCSAIEKTQRMLSGFCPHKVSAGQFSSLHVRDTKIEVAQFVKDLLLHLKKLF</u>

<u>REGRFN</u><u>ESKYGPPCPPCP</u><u>GGGSSGGGS</u><u>GGQPREPQVYTLPPSQEEMTKNQVSLTCLVKGFY</u>
　　　　　　IgG4Hinge　　　　　Linker　　　　　IgG4-CH3

<u>PSDIAVEWESNGQPENNYKTTPPVLDSDGSFFLYSRLTVDKSRWQEGNVFSCSVMHEALHN</u>

<u>HYTQKSLSLSLGK</u><u>MALIVLGGVAGLLLFIGLGIFF</u><u>KRGRKKLLYIFKQPFMRPVQTTQEEDGCS</u>
　　　　　　　　　　CD4 tm　　　　　　　　　　　　4-1BB cyto <u>CRFPEEEEGGCEL</u>GGG<u>RVKFSRSADAPAYQQGQNQLYNELNLGRREEYDVLDKRRGRDPE</u>
　　　　　　　　　　　　CD3ζ

<u>MGGKPRRKNPQEGLYNELQKDKMAEAYSEIGMKGERRRGKGHDGLYQGLSTATKDTYDA</u>

<u>LHMQALPPR</u>

GMCSFRa signal peptide
IL13(EmY)
IgG4Hinge
Linker
IgG4-Fc-CH3
CD4 transmembrane
4-1BB cyto
(Gly)3
Zeta

FIGURE 22

IL13(EmY)-IgG4(L235E,N297Q)-CD8tm-41BB-Zeta

<u>MLLLVTSLLLCELPHPAFLLI</u><u>PGPVPPSTALR</u>░<u>LIEELVNITQNQKAPLCNGSMVWSINLTAGM</u>
GMCSFRa signal peptide   IL13(EmY)

<u>YCAALESLINVSGCSAIEKTQRMLSGFCPHKVSAGQFSSLHVRDTKIEVAQFVKDLLLHLKKLF</u>

<u>REGRFNESKYGPPCP</u>░<u>CPAPEFEGGPSVFLFPPKPKDTLMISRTPEVTCVVVDVSQEDPEVQF</u>
            IGgG4-Fc(SmP)

<u>NWYVDGVEVHNAKTKPREEQFQSTYRVVSVLTVLHQDWLNGKEYKCKVSNKGLPSSIEKTIS</u>

<u>KAKGQPREPQVYTLPPSQEEMTKNQVSLTCLVKGFYPSDIAVEWESNGQPENNYKTTPPVL</u>

<u>DSDGSFFLYSRLTVDKSRWQEGNVFSCSVMHEALHNHYTQKSLSLSLGK</u><u>IYIWAPLAGTCGV</u>
                                                           CD8 tm

<u>LLLSLVIT</u><u>KRGRKKLLYIFKQPFMRPVQTTQEEDGCSCRFPEEEEGGCEL</u>GGG<u>RVKFSRSADAP</u>
         4-1BB cyto                                           CD3ζ

<u>AYQQGQNQLYNELNLGRREEYDVLDKRRGRDPEMGGKPRRKNPQEGLYNELQKDKMAEA</u>

<u>YSEIGMKGERRRGKGHDGLYQGLSTATKDTYDALHMQALPPR</u>

GMCSFRa signal peptide
IL13(EmY)
IgG4-Fc(SmP)
CD8 transmembrane
4-1BB cyto
(Gly)3
Zeta

FIGURE 23

IL13(EmY)-Linker-CD28tm-CD28gg-41BB-Zeta

<u>MLLLVTSLLLCELPHPAFLLIPGPVPPSTALR</u>▓<u>LIEELVNITQNQKAPLCNGSMVWSINLTAGM</u>
GMCSFRa signal peptide        IL13(EmY)

<u>YCAALESLINVSGCSAIEKTQRMLSGFCPHKVSAGQFSSLHVRDTKIEVAQFVKDLLLHLKKLF</u>

<u>REGRFN</u><u>GGGSSGGGSG</u><u>MFWVLVVVGGVLACYSLLVTVAFIIFWV</u><u>RSKRSRGGHSDYMNM</u>
     Linker         CD28(M) tm                    CD28gg <u>TPRRPGPTRKHYQPYAPPRDFAAYRS</u>GGG<u>KRGRKKLLYIFKQPFMRPVQTTQEEDGCSCRFP</u>
                                       4-1BB cyto <u>EEEEGGCEL</u>GGG<u>RVKFSRSADAPAYQQGQNQLYNELNLGRREEYDVLDKRRGRDPEMGGK</u>
         CD3ζ

<u>PRRKNPQEGLYNELQKDKMAEAYSEIGMKGERRRGKGHDGLYQGLSTATKDTYDALHMQ</u>

<u>ALPPR</u>

GMCSFRa signal peptide
IL13(EmY)
Linker
CD28(M) transmembrane
CD28gg
4-1BB cyto
(Gly)3
Zeta

FIGURE 24

IL13(EmY)-HL-CD28m-CD28gg-41BB-Zeta

<u>MLLLVTSLLLCELPHPAFLLIPGPVPPSTALR</u>LIEELVNITQNQKAPLCNGSMVWSINLTAGM
  GMCSFRa signal peptide         IL13(EmY)

YCAALESLINVSGCSAIEKTQRMLSGFCPHKVSAGQFSSLHVRDTKIEVAQFVKDLLLHLKKLF

REGRFN<u>ESKYGPPCP</u>CPGGGSSGGGSGMFWVLVVVGGVLACYSLLVTVAFIIFWVRSKRS
      IgG4Hinge        Linker            CD28(M) tm
CD28gg RGGHSDYMNMTPRRPGPTRKHYQPYAPPRDFAAYRS<u>GGG</u>KRGRKKLLYIFKQPFMRPVQT
                                              4-1BB cyto TQEEDGCSCRFPEEEEGGCEL<u>GGG</u>RVKFSRSADAPAYQQGQNQLYNELNLGRREEYDVLDK
                         CD3ζ

RRGRDPEMGGKPRRKNPQEGLYNELQKDKMAEAYSEIGMKGERRRGKGHDGLYQGLSTA

TKDTYDALHMQALPPR

GMCSFRa signal peptide
IL13(EmY)
IgG4Hinge
Linker
CD28(M) transmembrane
CD28gg
4-1BB cyto
(Gly)3
Zeta

Figure 25

IL13(EmY)-IgG4(HL-CH3)-CD28tm-CD28gg-41BB-Zeta

<u>MLLLVTSLLLCELPHPAFLLIPGPVPPSTALR</u><u>LIEELVNITQNQKAPLCNGSMVWSINLTAGM</u>
<u>GMCSFRa signal peptide</u>      <u>IL13(EmY)</u>

<u>YCAALESLINVSGCSAIEKTQRMLSGFCPHKVSAGQFSSLHVRDTKIEVAQFVKDLLLHLKKLF</u>

<u>REGRFNESKYGPPCP</u><u>CPGGGSSGGGSGG</u><u>QPREPQVYTLPPSQEEMTKNQVSLTCLVKGFY</u>
   <u>IgG4Hinge</u>        Linker          <u>IgG4 CH3</u>

<u>PSDIAVEWESNGQPENNYKTTPPVLDSDGSFFLYSRLTVDKSRWQEGNVFSCSVMHEALHN</u>

<u>HYTQKSLSLSLGKMFWVLVVVGGVLACYSLLVTVAFIIFWV</u><u>RSKRSGGHSDYMNMTPRRP</u>
            CD28(M) tm                            CD28gg

<u>GPTRKHYQPYAPPRDFAAYRSGGG</u><u>KRGRKKLLYIFKQPFMRPVQTTQEEDGCSCRFPEEEEG</u>
                              4-1BB cyto <u>GCELGGG</u><u>RVKFSRSADAPAYQQGQNQLYNELNLGRREEYDVLDKRRGRDPEMGGKPRRK</u>
         CD3ζ

<u>NPQEGLYNELQKDKMAEAYSEIGMKGERRRGKGHDGLYQGLSTATKDTYDALHMQALPP</u>

<u>R</u>

GMCSFRa signal peptide
IL13(EmY)
IgG4Hinge
Linker
IgG4 CH3
CD28 transmembrane
CD28gg
4-1BB cyto
(Gly)3
Zeta

FIGURE 26

IL13(EmY)-IgG4(L235E,N297Q)-CD28tm-CD28gg-41BB-Zeta

<u>MLLLVTSLLLCELPHPAFLLIPGPVPPSTALR</u><u>LIEELVNITQNQKAPLCNGSMVWSINLTAGM</u>
GMCSFRa signal peptide     IL13(EmY)

<u>YCAALESLINVSGCSAIEKTQRMLSGFCPHKVSAGQFSSLHVRDTKIEVAQFVKDLLLHLKKLF</u>

<u>REGRFNESKYGPPCP</u><u>CPAPEFEGGPSVFLFPPKPKDTLMISRTPEVTCVVVDVSQEDPEVQF</u>
        IgG4-Fc(L235E,N297Q)

<u>NWYVDGVEVHNAKTKPREEQFQSTYRVVSVLTVLHQDWLNGKEYKCKVSNKGLPSSIEKTIS</u>

<u>KAKGQPREPQVYTLPPSQEEMTKNQVSLTCLVKGFYPSDIAVEWESNGQPENNYKTTPPVL</u>

<u>DSDGSFFLYSRLTVDKSRWQEGNVFSCSVMHEALHNHYTQKSLSLSLGKM</u>FWVLVVVGGV
                                                                       CD28(M) tm
LACYSLLVTVAFIIFWV<u>RSKRSRGGHSDYMNMTPRRPGPTRKHYQPYAPPRDFAAYRS</u>GGG
                 CD28gg

<u>KRGRKKLLYIFKQPFMRPVQTTQEEDGCSCRFPEEEEGGCEL</u>GGG<u>RVKFSRSADAPAYQQG</u>
4-1BB cyto                                                                 CD3ζ

<u>QNQLYNELNLGRREEYDVLDKRRGRDPEMGGKPRRKNPQEGLYNELQKDKMAEAYSEIG</u>

<u>MKGERRRGKGHDGLYQGLSTATKDTYDALHMQALPPR</u>

GMCSFRa signal peptide
IL13(EmY)
IgG4-Fc(L235E,N297Q)
CD28 (M) transmembrane
CD28gg
(Gly)3
4-1BB cyto
(Gly)3
Zeta

FIGURE 27

IL13(EmY)-CD8h3-CD8tm-41BB-Zeta

<u>MLLLVTSLLLCELPHPAFLLI</u>PGPVPPSTALRLIEELVNITQNQKAPLCNGSMVWSINLTAGM GMCSFRa signal peptide       IL13(EmY)

YCAALESLINVSGCSAIEKTQRMLSGFCPHKVSAGQFSSLHVRDTKIEVAQFVKDLLLHLKKLF

REGRFN<u>AKPTTTPAPRPPTPAPTIASQPLSLRPEACRPAAGGAVHTRGLDFACD</u>IYIWAPLAG

CD8hinge (48 aa)                                      CD8tm

TCGVLLLSLVIT<u>GGG</u>KRGRKKLLYIFKQPFMRPVQTTQEEDGCSCRFPEEEEGGCEL<u>GGG</u>RVK 4-1BB cyto                                        CD3ζ

FSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

GMCSFRa signal peptide
IL13(EmY)
CD8hinge
CD8 transmembrane
(Gly)3
4-1BB cyto
(Gly)3
Zeta

SEQUENCE LISTING

```
<160> NUMBER OF SEQ ID NOS: 54

<210> SEQ ID NO 1
<211> LENGTH: 889
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
    130                 135                 140

Cys Pro Ala Pro Glu Phe Glu Gly Gly Pro Ser Val Phe Leu Phe Pro
145                 150                 155                 160
```

```
Pro Lys Pro Lys Asp Thr Leu Met Ile Ser Arg Thr Pro Glu Val Thr
                165                 170                 175
Cys Val Val Val Asp Val Ser Gln Glu Asp Pro Glu Val Gln Phe Asn
            180                 185                 190
Trp Tyr Val Asp Gly Val Glu Val His Asn Ala Lys Thr Lys Pro Arg
        195                 200                 205
Glu Glu Gln Phe Gln Ser Thr Tyr Arg Val Val Ser Val Leu Thr Val
    210                 215                 220
Leu His Gln Asp Trp Leu Asn Gly Lys Glu Tyr Lys Cys Lys Val Ser
225                 230                 235                 240
Asn Lys Gly Leu Pro Ser Ser Ile Glu Lys Thr Ile Ser Lys Ala Lys
                245                 250                 255
Gly Gln Pro Arg Glu Pro Gln Val Tyr Thr Leu Pro Pro Ser Gln Glu
            260                 265                 270
Glu Met Thr Lys Asn Gln Val Ser Leu Thr Cys Leu Val Lys Gly Phe
        275                 280                 285
Tyr Pro Ser Asp Ile Ala Val Glu Trp Glu Ser Asn Gly Gln Pro Glu
    290                 295                 300
Asn Asn Tyr Lys Thr Thr Pro Pro Val Leu Asp Ser Asp Gly Ser Phe
305                 310                 315                 320
Phe Leu Tyr Ser Arg Leu Thr Val Asp Lys Ser Arg Trp Gln Glu Gly
                325                 330                 335
Asn Val Phe Ser Cys Ser Val Met His Glu Ala Leu His Asn His Tyr
            340                 345                 350
Thr Gln Lys Ser Leu Ser Leu Ser Leu Gly Lys Met Ala Leu Ile Val
        355                 360                 365
Leu Gly Gly Val Ala Gly Leu Leu Leu Phe Ile Gly Leu Gly Ile Phe
    370                 375                 380
Phe Lys Arg Gly Arg Lys Lys Leu Leu Tyr Ile Phe Lys Gln Pro Phe
385                 390                 395                 400
Met Arg Pro Val Gln Thr Thr Gln Glu Glu Asp Gly Cys Ser Cys Arg
                405                 410                 415
Phe Pro Glu Glu Glu Glu Gly Gly Cys Glu Leu Gly Gly Gly Arg Val
            420                 425                 430
Lys Phe Ser Arg Ser Ala Asp Ala Pro Ala Tyr Gln Gln Gly Gln Asn
        435                 440                 445
Gln Leu Tyr Asn Glu Leu Asn Leu Gly Arg Arg Glu Glu Tyr Asp Val
    450                 455                 460
Leu Asp Lys Arg Arg Gly Arg Asp Pro Glu Met Gly Gly Lys Pro Arg
465                 470                 475                 480
Arg Lys Asn Pro Gln Glu Gly Leu Tyr Asn Glu Leu Gln Lys Asp Lys
                485                 490                 495
Met Ala Glu Ala Tyr Ser Glu Ile Gly Met Lys Gly Glu Arg Arg Arg
            500                 505                 510
Gly Lys Gly His Asp Gly Leu Tyr Gln Gly Leu Ser Thr Ala Thr Lys
        515                 520                 525
Asp Thr Tyr Asp Ala Leu His Met Gln Ala Leu Pro Pro Arg Leu Glu
    530                 535                 540
Gly Gly Gly Glu Gly Arg Gly Ser Leu Leu Thr Cys Gly Asp Val Glu
545                 550                 555                 560
Glu Asn Pro Gly Pro Arg Met Pro Pro Arg Leu Leu Phe Phe Leu
                565                 570                 575
```

-continued

```
Leu Phe Leu Thr Pro Met Glu Val Arg Pro Glu Pro Leu Val Val
            580                 585                 590

Lys Val Glu Glu Gly Asp Asn Ala Val Leu Gln Cys Leu Lys Gly Thr
    595                 600                 605

Ser Asp Gly Pro Thr Gln Gln Leu Thr Trp Ser Arg Glu Ser Pro Leu
    610                 615                 620

Lys Pro Phe Leu Lys Leu Ser Leu Gly Leu Pro Gly Leu Gly Ile His
625                 630                 635                 640

Met Arg Pro Leu Ala Ile Trp Leu Phe Ile Phe Asn Val Ser Gln Gln
                645                 650                 655

Met Gly Gly Phe Tyr Leu Cys Gln Pro Gly Pro Pro Ser Glu Lys Ala
            660                 665                 670

Trp Gln Pro Gly Trp Thr Val Asn Val Glu Gly Ser Gly Glu Leu Phe
    675                 680                 685

Arg Trp Asn Val Ser Asp Leu Gly Gly Leu Gly Cys Gly Leu Lys Asn
    690                 695                 700

Arg Ser Ser Glu Gly Pro Ser Ser Pro Ser Gly Lys Leu Met Ser Pro
705                 710                 715                 720

Lys Leu Tyr Val Trp Ala Lys Asp Arg Pro Glu Ile Trp Glu Gly Glu
                725                 730                 735

Pro Pro Cys Val Pro Pro Arg Asp Ser Leu Asn Gln Ser Leu Ser Gln
            740                 745                 750

Asp Leu Thr Met Ala Pro Gly Ser Thr Leu Trp Leu Ser Cys Gly Val
    755                 760                 765

Pro Pro Asp Ser Val Ser Arg Gly Pro Leu Ser Trp Thr His Val His
    770                 775                 780

Pro Lys Gly Pro Lys Ser Leu Leu Ser Leu Glu Leu Lys Asp Asp Arg
785                 790                 795                 800

Pro Ala Arg Asp Met Trp Val Met Glu Thr Gly Leu Leu Leu Pro Arg
                805                 810                 815

Ala Thr Ala Gln Asp Ala Gly Lys Tyr Tyr Cys His Arg Gly Asn Leu
            820                 825                 830

Thr Met Ser Phe His Leu Glu Ile Thr Ala Arg Pro Val Leu Trp His
    835                 840                 845

Trp Leu Leu Arg Thr Gly Gly Trp Lys Val Ser Ala Val Thr Leu Ala
    850                 855                 860

Tyr Leu Ile Phe Cys Leu Cys Ser Leu Val Gly Ile Leu His Leu Gln
865                 870                 875                 880

Arg Ala Leu Val Leu Arg Arg Lys Arg
                885

<210> SEQ ID NO 2
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Met Leu Leu Leu Val Thr Ser Leu Leu Leu Cys Glu Leu Pro His Pro
1               5                   10                  15

Ala Phe Leu Leu Ile Pro
            20
```

```
<210> SEQ ID NO 3
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

<210> SEQ ID NO 4
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 22
<212> TYPE: PRT
<213> ORGANISM: Homo sapiens

<400> SEQUENCE: 5

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 6
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 7
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 8
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 9
<211> LENGTH: 323
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

```
Glu Ile Thr Ala Arg Pro Val Leu Trp His Trp Leu Arg Thr Gly
        275                 280                 285

Gly Trp Lys Val Ser Ala Val Thr Leu Ala Tyr Leu Ile Phe Cys Leu
290                 295                 300

Cys Ser Leu Val Gly Ile Leu His Leu Gln Arg Ala Leu Val Leu Arg
305                 310                 315                 320

Arg Lys Arg

<210> SEQ ID NO 10
<211> LENGTH: 520
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Ala Pro Glu Phe
        115                 120                 125

Glu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Gly Leu Pro Ser
    210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Arg Leu
```

```
                290                 295                 300
Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Leu Gly Lys Met Ala Leu Ile Val Leu Gly Val Ala Gly
                340                 345                 350

Leu Leu Leu Phe Ile Gly Leu Gly Ile Phe Phe Lys Arg Gly Arg Lys
                355                 360                 365

Lys Leu Leu Tyr Ile Phe Lys Gln Pro Phe Met Arg Pro Val Gln Thr
                370                 375                 380

Thr Gln Glu Glu Asp Gly Cys Ser Cys Arg Phe Pro Glu Glu Glu
385                 390                 395                 400

Gly Gly Cys Glu Leu Gly Gly Gly Arg Val Lys Phe Ser Arg Ser Ala
                405                 410                 415

Asp Ala Pro Ala Tyr Gln Gln Gly Gln Asn Gln Leu Tyr Asn Glu Leu
                420                 425                 430

Asn Leu Gly Arg Arg Glu Glu Tyr Asp Val Leu Asp Lys Arg Arg Gly
                435                 440                 445

Arg Asp Pro Glu Met Gly Gly Lys Pro Arg Arg Lys Asn Pro Gln Glu
                450                 455                 460

Gly Leu Tyr Asn Glu Leu Gln Lys Asp Lys Met Ala Glu Ala Tyr Ser
465                 470                 475                 480

Glu Ile Gly Met Lys Gly Glu Arg Arg Arg Gly Lys Gly His Asp Gly
                485                 490                 495

Leu Tyr Gln Gly Leu Ser Thr Ala Thr Lys Asp Thr Tyr Asp Ala Leu
                500                 505                 510

His Met Gln Ala Leu Pro Pro Arg
                515                 520

<210> SEQ ID NO 11
<211> LENGTH: 405
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
                35                  40                  45

Ser Leu Ile Asn Val Ser Gly Cys Ser Ala Ile Glu Lys Thr Gln Arg
                50                  55                  60

Met Leu Ser Gly Phe Cys Pro His Lys Val Ser Ala Gly Gln Phe Ser
65              70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
                100                 105                 110

Glu Ser Lys Tyr Gly Pro Pro Cys Pro Pro Cys Pro Ala Pro Glu Phe
                115                 120                 125
```

Glu Gly Gly Pro Ser Val Phe Leu Phe Pro Pro Lys Pro Lys Asp Thr
            130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Gly Leu Pro Ser
    210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Arg Leu
    290                 295                 300

Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Leu Gly Lys Met Ala Leu Ile Val Leu Gly Gly Val Ala Gly
            340                 345                 350

Leu Leu Leu Phe Ile Gly Leu Gly Ile Phe Phe Lys Arg Gly Arg Lys
        355                 360                 365

Lys Leu Leu Tyr Ile Phe Lys Gln Pro Phe Met Arg Pro Val Gln Thr
    370                 375                 380

Thr Gln Glu Glu Asp Gly Cys Ser Cys Arg Phe Pro Glu Glu Glu Glu
385                 390                 395                 400

Gly Gly Cys Glu Leu
            405

<210> SEQ ID NO 12
<211> LENGTH: 7754
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa aggaaaccag aggagctctc tcgacgcag gactcggctt     240 gctgaagcgc gcacggcaag aggcgagggg cggcgactgg tgagtacgcc aaaaattttg     300
actagcggag gctagaagga gagagatggg tgcgagagcg tcagtattaa gcgggggaga     360

```
attagatcga tgggaaaaaa ttcggttaag gccagggggga aagaaaaaat ataaattaaa      420
acatatagta tgggcaagca gggagctaga acgattcgca gttaatcctg gcctgttaga      480
aacatcagaa ggctgtagac aaatactggg acagctacaa ccatcccttc agacaggatc      540
agaagaactt agatcattat ataatacagt agcaaccctc tattgtgtgc atcaaaggat      600
agagataaaa gacaccaagg aagctttaga caagatagag gaagagcaaa acaaaagtaa      660
gaaaaaagca cagcaagcag cagctgacac aggacacagc aatcaggtca gccaaaatta      720
ccctatagtg cagaacatcc aggggcaaat ggtacatcag gccatatcac ctagaacttt      780
aaatgcatgg gtaaaagtag tagaagagaa ggctttcagc ccagaagtga tacccatgtt      840
ttcagcatta tcagaaggag ccaccccaca agatttaaac accatgctaa acacagtggg      900
gggacatcaa gcagccatgc aaatgttaaa agagaccatc aatgaggaag ctgcaggcaa      960
agagaagagt ggtgcagaga gaaaaaagag cagtgggaat aggagctttg ttccttgggt     1020
tcttgggagc agcaggaagc actatgggcg cagcgtcaat gacgctgacg gtacaggcca     1080
gacaattatt gtctggtata gtgcagcagc agaacaattt gctgagggct attgaggcgc     1140
aacagcatct gttgcaactc acagtctggg gcatcaagca gctccaggca agaatcctgg     1200
ctgtggaaag atacctaaag gatcaacagc tcctggggat ttggggttgc tctggaaaac     1260
tcatttgcac cactgctgtg ccttggatct acaaatggca gtattcatcc acaattttaa     1320
aagaaaaggg gggattgggg ggtacagtgc aggggaaaga atagtagaca taatagcaac     1380
agacatacaa actaaagaat tacaaaaaca aattacaaaa attcaaaatt ttcgggttta     1440
ttacagggac agcagagatc cagtttgggg atcaattgca tgaagaatct gcttagggtt     1500
aggcgttttg cgctgcttcg cgaggatctg cgatcgctcc ggtgcccgtc agtgggcaga     1560
gcgcacatcg cccacagtcc ccgagaagtt ggggggaggg gtcggcaatt gaaccggtgc     1620
ctagagaagg tggcgcgggg taaactggga aagtgatgtc gtgtactggc tccgcctttt     1680
tcccgagggt gggggagaac cgtatataag tgcagtagtc gccgtgaacg ttctttttcg     1740
caacgggttt gccgccagaa cacagctgaa gcttcgaggg gctcgcatct ctccttcacg     1800
cgcccgccgc cctacctgag gccgccatcc acgccggttg agtcgcgttc tgccgcctcc     1860
cgcctgtggt gcctcctgaa ctgcgtccgc cgtctaggta agtttaaagc tcaggtcgag     1920
accgggcctt tgtccggcgc tcccttggag cctacctaga ctcagccggc tctccacgct     1980
ttgcctgacc ctgcttgctc aactctacgt ctttgtttcg ttttctgttc tgcgccgtta     2040
cagatccaag ctgtgaccgg cgcctacggg tagcgccgcc accatgctgc tgctggtgac     2100
cagcctgctg ctgtgcgagc tgccccaccc cgcctttctg ctgatccctg gccccgtgcc     2160
ccctagcacc gccctgcgct acctgatcga ggaactggtg aacatcaccc agaaccagaa     2220
agcccccctg tgcaacggca gcatggtgtg gagcatcaac ctgaccgccg gcatgtactg     2280
tgccgccctg gaaagcctga tcaacgtgag cggctgcagc gccatcgaga aacccagcg     2340
gatgctgtcc ggcttctgcc cccacaaggt gtccgccgga cagttcagca gcctgcacgt     2400
gcgggacacc aagatcgagg tgcccagtt cgtgaaggac ctgctgctgc acctgaagaa     2460
gctgttccgg gagggccggt tcaactacaa gaccaccccc cctgtgctgg acagcgacgg     2520
cagcttcttc ctgtacagca ggctgaccgt ggacaagagc cggtggcagg aaggcaacgt     2580
cttttagctgc agcgtgatgc acgaggccct gcacaaccac tacacccaga gagcctgtc     2640
cctgagcctg gcaagcgggt gaagttcagc cggtccgcc gacgccctg cctaccagca     2700
gggccagaac cagctgtaca acgagctgaa cctgggcagg cgggaggaat acgacgtgct     2760
```

```
ggacaagcgg agaggccggg accctgagat gggcggcaag cctcggcgga agaaccccca    2820
ggaaggcctg tataacgaac tgcagaaaga caagatggcc gaggcctaca gcagatcgg     2880 catgaagggc gagcggaggc ggggcaaggg ccacgacggc ctgtatcagg gcctgtccac    2940
cgccaccaag gatacctacg acgccctgca catgcaggcc ctgcccccaa ggtctagacc    3000
cgggctgcag gaattcgata tcaagcttat cgataatcaa cctctggatt acaaaatttg    3060
tgaaagattg actggtattc ttaactatgt tgctcctttt acgctatgtg gatacgctgc    3120
tttaatgcct ttgtatcatg ctattgcttc ccgtatggct ttcattttct cctccttgta    3180
taaatcctgg ttgctgtctc tttatgagga gttgtggccc gttgtcaggc aacgtggcgt    3240
ggtgtgcact gtgtttgctg acgcaacccc cactggttgg ggcattgcca ccacctgtca    3300
gctcctttcc gggactttcg ctttcccccct ccctattgcc acggcggaac tcatcgccgc    3360
ctgccttgcc cgctgctgga cagggctcg gctgttgggc actgacaatt ccgtggtgtt    3420
gtcggggaaa tcatcgtcct ttccttggct gctcgcctgt gttgccacct ggattctgcg    3480
cgggacgtcc ttctgctacg tcccttcggc cctcaatcca gcggaccttc cttcccgcgg    3540
cctgctgccg gctctgcggc ctcttccgcg tcttcgcctt cgccctcaga cgagtcggat    3600 ctcccttttgg gccgcctccc cgcatcgata ccgtcgacta gccgtacctt taagaccaat    3660
gacttacaag gcagctgtag atcttagcca cttttttaaaa gaaaaggggg gactggaagg    3720
gctaattcac tcccaaagaa gacaagatct gcttttttgcc tgtactgggt ctctctggtt    3780
agaccagatc tgagcctggg agctctctgg ctaactaggg aacccactgc ttaagcctca    3840
ataaagcttg ccttgagtgc ttcaagtagt gtgtgcccgt ctgttgtgtg actctggtaa    3900
ctagagatcc ctcagaccct tttagtcagt gtggaaaatc tctagcagaa ttcgatatca    3960
agcttatcga taccgtcgac ctcgaggggg ggcccggtac ccaattcgcc ctatagtgag    4020
tcgtattaca attcactggc cgtcgtttta caacgtcgtg actgggaaaa ccctggcgtt    4080
acccaactta atcgccttgc agcacatccc cctttcgcca gctggcgtaa tagcgaagag    4140
gcccgcaccg atcgcccttc ccaacagttg cgcagcctga atggcgaatg gaaattgtaa    4200
gcgttaatat tttgttaaaa ttcgcgttaa attttttgtta aatcagctca ttttttaacc    4260
aataggccga atcggcaaa atcccttata aatcaaaaga atagaccgag atagggttga    4320
gtgttgttcc agtttggaac aagagtccac tattaaagaa cgtggactcc aacgtcaaag    4380
ggcgaaaaac cgtctatcag ggcgatggcc cactacgtga accatcaccc taatcaagtt    4440
ttttggggtc gaggtgccgt aaagcactaa atcggaaccc taaagggagc ccccgattta    4500
gagcttgacg gggaaagccg gcgaacgtgg cgagaaagga agggaagaaa gcgaaaggag    4560
cgggcgctag ggcgctggca agtgtagcgg tcacgctgcg cgtaaccacc acccgccg     4620 cgcttaatgc gccgctacag gcgcgtcag gtggcacttt tcggggaaat gtgcgcggaa    4680
cccctatttg tttatttttc taaatacatt caaatatgta tccgctcatg agacaataac    4740
cctgataaat gcttcaataa tattgaaaaa ggaagagtat gagtattcaa catttccgtg    4800
tcgcccttat tcccttttt gcggcatttt gccttcctgt ttttgctcac ccagaaacgc    4860
tggtgaaagt aaaagatgct gaagatcagt tgggtgcacg agtgggttac atcgaactgg    4920
atctcaacag cggtaagatc cttgagagtt ttcgccccga agaacgtttt ccaatgatga    4980
gcacttttaa agttctgcta tgtggcgcgg tattatcccg tattgacgcc gggcaagagc    5040
aactcggtcg ccgcatacac tattctcaga atgacttggt tgagtactca ccagtcacag    5100
```

```
aaaagcatct tacggatggc atgacagtaa gagaattatg cagtgctgcc ataaccatga   5160
gtgataacac tgcggccaac ttacttctga caacgatcgg aggaccgaag gagctaaccg   5220
cttttttgca caacatgggg gatcatgtaa ctcgccttga tcgttgggaa ccggagctga   5280
atgaagccat accaaacgac gagcgtgaca ccacgatgcc tgtagcaatg caacaacgt    5340 tgcgcaaact attaactggc gaactactta ctctagcttc ccggcaacaa ttaatagact   5400
ggatggaggc ggataaagtt gcaggaccac ttctgcgctc ggcccttccg gctggctggt   5460
ttattgctga taaatctgga gccggtgagc gtgggtctcg cggtatcatt gcagcactgg   5520
ggccagatgg taagccctcc cgtatcgtag ttatctacac gacggggagt caggcaacta   5580
tggatgaacg aaatagacag atcgctgaga taggtgcctc actgattaag cattggtaac   5640
tgtcagacca agtttactca tatatacttt agattgattt aaaacttcat ttttaattta   5700
aaaggatcta ggtgaagatc cttttttgata atctcatgac caaaatccct taacgtgagt   5760
tttcgttcca ctgagcgtca gaccccgtag aaaagatcaa aggatcttct tgagatcctt   5820
tttttctgcg cgtaatctgc tgcttgcaaa caaaaaaacc accgctacca gcggtggttt   5880
gtttgccgga tcaagagcta ccaactcttt ttccgaaggt aactggcttc agcagagcgc   5940
agataccaaa tactgttctt ctagtgtagc cgtagttagg ccaccacttc aagaactctg   6000
tagcaccgcc tacataccte gctctgctaa tcctgttacc agtggctgct gccagtggcg   6060
ataagtcgtg tcttaccggg ttggactcaa gacgatagtt accggataag cgcagcggt    6120 cgggctgaac ggggggttcg tgcacacagc ccagcttgga gcgaacgacc tacaccgaac   6180
tgagatacct acagcgtgag ctatgagaaa gcgccacgct tcccgaaggg agaaaggcgg   6240
acaggtatcc ggtaagcggc agggtcggaa caggagagcg cacgagggag cttccagggg   6300
gaaacgcctg gtatctttat agtcctgtcg ggtttcgcca cctctgactt gagcgtcgat   6360
ttttgtgatg ctcgtcaggg gggcggagcc tatggaaaaa cgccagcaac gcggcctttt   6420
tacggttcct ggccttttgc tggccttttg ctcacatgtt ctttcctgcg ttatcccctg   6480
attctgtgga taaccgtatt accgcctttg agtgagctga taccgctcgc cgcagccgaa   6540
cgaccgagcg cagcgagtca gtgagcgagg aagcggaaga gcgcccaata cgcaaaccgc   6600
ctctccccgc gcgttggccg attcattaat gcagctggca cgacaggttt cccgactgga   6660
aagcgggcag tgagcgcaac gcaattaatg tgagttagct cactcattag gcaccccagg   6720
ctttacactt tatgcttccg gctcgtatgt tgtgtggaat tgtgagcgga taacaatttc   6780
acacaggaaa cagctatgac catgattacg ccaagctcga aattaaccct cactaaaggg   6840
aacaaaagct ggagctccac cgcggtggcg gcctcgaggt cgagatccgg tcgaccagca   6900
accatagtcc cgcccctaac tccgcccatc ccgcccctaa ctccgcccag ttccgcccat   6960
tctccgcccc atggctgact aattttttt atttatgcag aggccgaggc cgcctcggcc   7020
tctgagctat tccagaagta gtgaggaggc ttttttggag gcctaggctt ttgcaaaaag   7080
cttcgacggt atcgattggc tcatgtccaa cattaccgcc atgttgacat tgattattga   7140
ctagttatta atagtaatca attacggggt cattagttca tagcccatat atggagttcc   7200
gcgttacata acttacggta aatggcccgc ctggctgacc gcccaacgac ccccgcccat   7260
tgacgtcaat aatgacgtat gttcccatag taacgccaat agggactttc cattgacgtc   7320
aatgggtgga gtatttacgg taaactgccc acttggcagt acatcaagtg tatcatatgc   7380
caagtacgcc ccctattgac gtcaatgacg gtaaatggcc cgcctggcat tatgcccagt   7440
acatgacctt atgggacttt cctacttggc agtacatcta cgtattagtc atcgctatta   7500
```

```
ccatggtgat gcggttttgg cagtacatca atgggcgtgg atagcggttt gactcacggg    7560
gatttccaag tctccacccc attgacgtca atgggagttt gttttggcac caaaatcaac    7620
gggactttcc aaaatgtcgt aacaactccg ccccattgac gcaaatgggc ggtaggcgtg    7680
tacggaattc ggagtggcga gccctcagat cctgcatata agcagctgct ttttgcctgt    7740
actgggtctc tctg                                                      7754
```

<210> SEQ ID NO 13
<211> LENGTH: 8732
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13

```
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcggggagaa     360
attagatcga tgggaaaaaa ttcggttaag gccagggggga agaaaaaat ataaattaaa     420 acatatagta tgggcaagca gggagctaga acgattcgca gttaatcctg gcctgttaga     480
aacatcagaa ggctgtagac aaatactggg acagctacaa ccatcccttc agacaggatc     540
agaagaactt agatcattat ataatacagt agcaaccctc tattgtgtgc atcaaaggat     600
agagataaaa gacaccaagg aagctttaga caagatagag gaagagcaaa acaaaagtaa     660
gaaaaaagca cagcaagcag cagctgacac aggacacagc aatcaggtca gccaaaatta     720
ccctatagtg cagaacatcc aggggcaaat ggtacatcag gccatatcac ctagaacttt     780
aaatgcatgg gtaaaagtag tagaagagaa ggctttcagc ccagaagtga tacccatgtt     840
ttcagcatta tcagaaggag ccaccccaca agatttaaac accatgctaa acacagtggg     900
gggacatcaa gcagccatgc aaatgttaaa agagaccatc aatgaggaag ctgcaggcaa     960
agagaagagt ggtgcagaga gaaaaaagag cagtgggaat aggagctttg ttccttgggt    1020
tcttgggagc agcaggaagc actatgggcg cagcgtcaat gacgctgacg gtacaggcca    1080
gacaattatt gtctggtata gtgcagcagc agaacaattt gctgagggct attgaggcgc    1140
aacagcatct gttgcaactc acagtctggg gcatcaagca gctccaggca agaatcctgg    1200
ctgtggaaag atacctaaag gatcaacagc tcctggggat ttggggttgc tctggaaaac    1260
tcatttgcac cactgctgtg ccttggatct acaaatggca gtattcatcc acaatttaa     1320 aagaaaaggg gggattgggg ggtacagtgc aggggaaaga atagtagaca taatagcaac    1380
agacatacaa actaaagaat tacaaaaaca aattacaaaa attcaaaatt ttcgggttta    1440
ttacagggac agcagagatc cagtttgggg atcaattgca tgaagaatct gcttagggtt    1500
aggcgttttg cgctgcttcg cgaggatctg cgatcgctcc ggtgcccgtc agtgggcaga    1560
gcgcacatcg cccacagtcc ccgagaagtt gggggggaggg gtcggcaatt gaaccggtgc    1620
ctagagaagg tggcgcgggg taaactggga aagtgatgtc gtgtactggc tccgcctttt    1680
```

-continued

```
tcccgagggt gggggagaac cgtatataag tgcagtagtc gccgtgaacg ttctttttcg    1740
caacgggttt gccgccagaa cacagctgaa gcttcgaggg gctcgcatct ctccttcacg    1800
cgcccgccgc cctacctgag gccgccatcc acgccggttg agtcgcgttc tgccgcctcc    1860
cgcctgtggt gcctcctgaa ctgcgtccgc cgtctaggta agtttaaagc tcaggtcgag    1920
accgggcctt tgtccggcgc tcccttggag cctacctaga ctcagccggc tctccacgct    1980
ttgcctgacc ctgcttgctc aactctacgt ctttgtttcg ttttctgttc tgcgccgtta    2040
cagatccaag ctgtgaccgg cgcctacggc tagcgccgcc accatgctgc tgctggtgac    2100
cagcctgctg ctgtgcgagc tgccccaccc cgcctttctg ctgatccccg acatccagat    2160
gacccagacc acctccagcc tgagcgccag cctgggcgac cgggtgacca tcagctgccg    2220
ggccagccag gacatcagca agtacctgaa ctggtatcag cagaagcccg acggcaccgt    2280
caagctgctg atctaccaca ccagccggct gcacagcggc gtgcccagcc ggtttagcgg    2340
cagcggctcc ggcaccgact acagcctgac catctccaac ctggaacagg aagatatcgc    2400
cacctacttt tgccagcagg gcaacacact gccctacacc tttggcggcg gaacaaagct    2460
ggaaatcacc ggcagcacct ccggcagcgg caagcctggc agcggcgagg gcagcaccaa    2520
gggcgaggtg aagctgcagg aaagcggccc tggcctggtg ccccagccc agagcctgag    2580
cgtgacctgc accgtgagcg gcgtgagcct gcccgactac ggcgtgagct ggatccggca    2640
gcccccagg aagggcctgg aatggctggg cgtgatctgg ggcagcgaga ccacctacta    2700
caacagcgcc ctgaagagcc ggctgaccat catcaaggac aacagcaaga gccaggtgtt    2760
cctgaagatg aacagcctgc agaccgacga caccgccatc tactactgcg ccaagcacta    2820
ctactacggc ggcagctacg ccatggacta ctggggccag ggcaccagcg tgaccgtgag    2880
cagcgagagc aagtacggcc ctccctgccc cccttgccct gccccgagt tcctgggcgg    2940
acccagcgtg ttcctgttcc cccccaagcc caaggacacc ctgatgatca gccggacccc    3000
cgaggtgacc tgcgtggtgg tggacgtgag ccaggaagat cccgaggtcc agttcaattg    3060
gtacgtggac ggcgtggagg tgcacaacgc caagaccaag cccagggaag agcagttcaa    3120
cagcacctac cgggtggtgt ccgtgctgac cgtgctgcac caggactggc tgaacggcaa    3180
agaatacaag tgcaaggtgt ccaacaaggg cctgcccagc agcatcgaga aaaccatcag    3240
caaggccaag ggccagcctc gggagcccca ggtgtacacc ctgccccctt cccaggaaga    3300
gatgaccaag aatcaggtgt ccctgacctg cctggtgaag ggcttctacc ccagcgacat    3360
cgccgtggag tgggagagca acggccagcc cgagaacaac tacaagacca ccccccctgt    3420
gctggacagc gacggcagct tcttcctgta cagcaggctg accgtggaca gagccggtg    3480
gcaggaaggc aacgtcttta gctgcagcgt gatgcacgag gccctgcaca accactacac    3540
ccagaagagc ctgtccctga cctgggcaa gatggccctg atcgtgctgg cggcgtggc    3600
cgggctgctg ctgttcatcg gcctgggcat cttttccgg gtgaagttca gccggtccgc    3660
cgacgcccct gcctaccagc agggccagaa ccagctgtac aacgagctga acctgggcag    3720
gcgggaggaa tacgacgtgc tggacaagcg gagaggccgg accctgaga tgggcggcaa    3780
gcccaggcgg aagaaccctc aggaaggcct gtataacgaa ctgcagaaag acaagatggc    3840
cgaggcctac agcgagatcg gcatgaaggg cgagcggcgg aggggcaagg gccacgacgg    3900
cctgtaccag ggcctgagca ccgccaccaa ggatacctac gacgccctgc acatgcaggc    3960
cctgcccccc aggtgacccg ggctgcagga attcgatatc aagcttatcg ataatcaacc    4020
tctggattac aaaatttgtg aaagattgac tggtattctt aactatgttg ctccttttac    4080
```

```
gctatgtgga tacgctgctt taatgccttt gtatcatgct attgcttccc gtatggcttt    4140 catttctcc tccttgtata aatcctggtt gctgtctctt tatgaggagt tgtggcccgt      4200
tgtcaggcaa cgtggcgtgg tgtgcactgt gtttgctgac gcaaccccca ctggttgggg    4260
cattgccacc acctgtcagc tcctttccgg gactttcgct ttcccctcc ctattgccac     4320 ggcggaactc atcgccgcct gccttgcccg ctgctggaca ggggctcggc tgttgggcac    4380
tgacaattcc gtggtgttgt cggggaaatc atcgtccttt ccttggctgc tcgcctgtgt    4440
tgccacctgg attctgcgcg ggacgtcctt ctgctacgtc ccttcggccc tcaatccagc    4500
ggaccttcct tcccgcggcc tgctgccggc tctgcggcct cttccgcgtc ttcgccttcg    4560
ccctcagacg agtcggatct cccttgggc cgcctccccg catcgatacc gtcgactagc     4620 cgtacctta agaccaatga cttacaaggc agctgtagat cttagccact ttttaaaaga     4680
aaagggggga ctggaagggc taattcactc ccaaagaaga caagatctgc ttttgcctg     4740 tactgggtct ctctggttag accagatctg agcctgggag ctctctggct aactagggaa    4800
cccactgctt aagcctcaat aaagcttgcc ttgagtgctt caagtagtgt gtgcccgtct    4860
gttgtgtgac tctggtaact agagatccct cagacccttt tagtcagtgt ggaaaatctc    4920
tagcagaatt cgatatcaag cttatcgata ccgtcgacct cgagggggg cccggtaccc     4980 aattcgccct atagtgagtc gtattacaat tcactggccg tcgttttaca acgtcgtgac    5040
tgggaaaacc ctggcgttac ccaacttaat cgccttgcag cacatccccc tttcgccagc    5100
tggcgtaata gcgaagaggc ccgcaccgat cgcccttccc aacagttgcg cagcctgaat    5160
ggcgaatgga aattgtaagc gttaatattt tgttaaaatt cgcgttaaat ttttgttaaa    5220
tcagctcatt ttttaaccaa taggccgaaa tcggcaaaat cccttataaa tcaaagaat    5280 agaccgagat agggttgagt gttgttccag tttggaacaa gagtccacta ttaaagaacg    5340
tggactccaa cgtcaagggg cgaaaaaccg tctatcaggg cgatggccca ctacgtgaac    5400
catcacccta atcaagtttt tggggtcga ggtgccgtaa agcactaaat cggaaccta     5460 aagggagccc ccgatttaga gcttgacggg gaaagccggc gaacgtggcg agaaaggaag    5520
ggaagaaagc gaaaggagcg gcgctaggg cgctggcaag tgtagcggtc acgctgcgcg    5580
taaccaccac acccgccgcg cttaatgcgc cgctacaggg cgcgtcaggt ggcacttttc    5640
ggggaaatgt gcgcggaacc cctatttgtt tatttttcta aatacattca aatatgtatc    5700
cgctcatgag acaataaccc tgataaatgc ttcaataata ttgaaaaagg aagagtatga    5760
gtattcaaca tttccgtgtc gcccttattc cctttttgc ggcattttgc cttcctgttt     5820
ttgctcaccc agaaacgctg gtgaaagtaa aagatgctga agatcagttg ggtgcacgag    5880
tgggttacat cgaactggat ctcaacagcg gtaagatcct tgagagtttt cgccccgaag    5940
aacgttttcc aatgatgagc acttttaaag ttctgctatg tggcgcggta ttatcccgta    6000
ttgacgccgg gcaagagcaa ctcggtcgcc gcatacacta ttctcagaat gacttggttg    6060
agtactcacc agtcacagaa aagcatctta cggatggcat gacagtaaga gaattatgca    6120
gtgctgccat aaccatgagt gataacactg cggccaactt acttctgaca acgatcggag    6180
gaccgaagga gctaaccgct ttttgcaca acatggggga tcatgtaact cgccttgatc      6240
gttgggaacc ggagctgaat gaagccatac caaacgacga gcgtgacacc acgatgcctg    6300
tagcaatggc aacaacgttg cgcaaactat taactggcga actacttact ctagcttccc    6360
ggcaacaatt aatagactgg atggaggcgg ataaagttgc aggaccactt ctgcgctcgg    6420
```

```
cccttccggc tggctggttt attgctgata atctggagcc cggtgagcgt gggtctcgcg    6480
gtatcattgc agcactgggg ccagatggta agccctcccg tatcgtagtt atctacacga    6540
cggggagtca ggcaactatg gatgaacgaa atagacagat cgctgagata ggtgcctcac    6600
tgattaagca ttggtaactg tcagaccaag tttactcata tactttag attgatttaa     6660
aacttcattt ttaatttaaa aggatctagg tgaagatcct ttttgataat ctcatgacca    6720
aaatccctta acgtgagttt tcgttccact gagcgtcaga ccccgtagaa aagatcaaag    6780
gatcttcttg agatcctttt tttctgcgcg taatctgctg cttgcaaaca aaaaaaccac    6840
cgctaccagc ggtggtttgt ttgccggatc aagagctacc aactcttttt ccgaaggtaa    6900
ctggcttcag cagagcgcag ataccaaata ctgttcttct agtgtagccg tagttaggcc    6960
accacttcaa gaactctgta gcaccgccta catacctcgc tctgctaatc ctgttaccag    7020
tggctgctgc cagtggcgat aagtcgtgtc ttaccgggtt ggactcaaga cgatagttac    7080
cggataaggc gcagcggtcg ggctgaacgg ggggttcgtg cacacagccc agcttggagc    7140
gaacgaccta caccgaactg agatacctac agcgtgagct atgagaaagc gccacgcttc    7200
ccgaagggag aaaggcggac aggtatccgg taagcggcag ggtcggaaca ggagagcgca    7260
cgagggagct tccaggggga aacgcctggt atctttatag tcctgtcggg tttcgccacc    7320
tctgacttga gcgtcgattt ttgtgatgct cgtcaggggg gcggagccta tggaaaaacg    7380
ccagcaacgc ggcctttta cggttcctgg ccttttgctg gccttttgct cacatgttct    7440
ttcctgcgtt atcccctgat tctgtggata accgtattac cgcctttgag tgagctgata    7500
ccgctcgccg cagccgaacg accgagcgca gcgagtcagt gagcgaggaa gcggaagagc    7560
gcccaatacg caaaccgcct ctccccgcgc gttggccgat tcattaatgc agctggcacg    7620
acaggtttcc cgactggaaa gcgggcagtg agcgcaacgc aattaatgtg agttagctca    7680
ctcattaggc accccaggct ttacacttta tgcttccggc tcgtatgttg tgtggaattg    7740
tgagcggata acaatttcac acaggaaaca gctatgacca tgattacgcc aagctcgaaa    7800
ttaaccctca ctaaagggaa caaaagctgg agctccaccg cggtggcggc ctcgaggtcg    7860
agatccggtc gaccagcaac catagtcccg cccctaactc cgcccatccc gcccctaact    7920
ccgcccagtt ccgcccattc tccgccccat ggctgactaa ttttttttat ttatgcagag    7980
gccgaggccg cctcggcctc tgagctattc cagaagtagt gaggaggctt ttttggaggc    8040
ctaggctttt gcaaaaagct cgacggtat cgattggctc atgtccaaca ttaccgccat     8100
gttgacattg attattgact agttattaat agtaatcaat tacggggtca ttagttcata    8160
gcccatatat ggagttccgc gttacataac ttacggtaaa tggcccgcct ggctgaccgc    8220
ccaacgaccc ccgcccattg acgtcaataa tgacgtatgt tcccatagta acgccaatag    8280
ggactttcca ttgacgtcaa tgggtggagt atttacggta aactgcccac ttggcagtac    8340
atcaagtgta tcatatgcca agtacgcccc ctattgacgt caatgacggt aaatggcccg    8400
cctggcatta tgcccagtac atgaccttat gggactttcc tacttggcag tacatctacg    8460
tattagtcat cgctattacc atggtgatgc ggttttggca gtacatcaat gggcgtggat    8520
agcggtttga ctcacgggga tttccaagtc tccaccccat tgacgtcaat gggagtttgt    8580
tttggcacca aaatcaacgg gactttccaa aatgtcgtaa caactccgcc ccattgacgc    8640
aaatgggcgg taggcgtgta cggaattcgg agtggcgagc cctcagatcc tgcatataag    8700
cagctgcttt ttgcctgtac tgggtctctc tg                                  8732
```

```
<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly Gly Ser Ser Gly Gly Gly Ser Gly
1               5                   10

<210> SEQ ID NO 15
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Glu Ser Lys Tyr Gly Pro Pro Cys Pro Pro Cys Pro
1               5                   10

<210> SEQ ID NO 16
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Ser Lys Tyr Gly Pro Pro Cys Pro Pro Cys Pro Gly Gly Gly Ser
1               5                   10                  15

Ser Gly Gly Gly Ser Gly
            20

<210> SEQ ID NO 17
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 18
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18
```

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45
```

<210> SEQ ID NO 19
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45
```

<210> SEQ ID NO 20
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

```
Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
            35                  40                  45

Cys Leu Val Lys Gly Phe Tyr Pro Ser Asp Ile Ala Val Glu Trp Glu
        50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys
```

<210> SEQ ID NO 21
<211> LENGTH: 21
<212> TYPE: PRT
<213> ORGANISM: Homo sapiens

<400> SEQUENCE: 21

```
Leu Cys Tyr Leu Leu Asp Gly Ile Leu Phe Ile Tyr Gly Val Ile Leu
1               5                   10                  15
```

Thr Ala Leu Phe Leu
            20

<210> SEQ ID NO 22
<211> LENGTH: 27
<212> TYPE: PRT
<213> ORGANISM: Homo sapiens

<400> SEQUENCE: 22

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 23
<211> LENGTH: 21
<212> TYPE: PRT
<213> ORGANISM: Homo sapiens

<400> SEQUENCE: 23

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 24
<211> LENGTH: 23
<212> TYPE: PRT
<213> ORGANISM: Homo sapiens

<400> SEQUENCE: 24

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 25
<211> LENGTH: 24
<212> TYPE: PRT
<213> ORGANISM: Homo sapiens

<400> SEQUENCE: 25

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 26
<211> LENGTH: 27
<212> TYPE: PRT
<213> ORGANISM: Homo sapiens

<400> SEQUENCE: 26

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 27
<211> LENGTH: 41
<212> TYPE: PRT
<213> ORGANISM: Homo sapiens

<400> SEQUENCE: 27

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 28
<211> LENGTH: 41
<212> TYPE: PRT
<213> ORGANISM: Homo sapiens

<400> SEQUENCE: 28

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 29
<211> LENGTH: 42
<212> TYPE: PRT
<213> ORGANISM: Homo sapiens

<400> SEQUENCE: 29

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 30
<211> LENGTH: 42
<212> TYPE: PRT
<213> ORGANISM: Homo sapiens

<400> SEQUENCE: 30

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 31
<211> LENGTH: 362
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg

```
            20                  25                  30
Tyr Leu Ile Glu Glu Leu Val Asn Ile Thr Gln Asn Gln Lys Ala Pro
        35                  40                  45
Leu Cys Asn Gly Ser Met Val Trp Ser Ile Asn Leu Thr Ala Gly Met
    50                  55                  60
Tyr Cys Ala Ala Leu Glu Ser Leu Ile Asn Val Ser Gly Cys Ser Ala
65                  70                  75                  80
Ile Glu Lys Thr Gln Arg Met Leu Ser Gly Phe Cys Pro His Lys Val
                85                  90                  95
Ser Ala Gly Gln Phe Ser Ser Leu His Val Arg Asp Thr Lys Ile Glu
            100                 105                 110
Val Ala Gln Phe Val Lys Asp Leu Leu Leu His Leu Lys Lys Leu Phe
            115                 120                 125
Arg Glu Gly Arg Phe Asn Ala Lys Pro Thr Thr Thr Pro Ala Pro Arg
        130                 135                 140
Pro Pro Thr Pro Ala Pro Thr Ile Ala Ser Gln Pro Leu Ser Leu Arg
145                 150                 155                 160
Pro Glu Ala Cys Arg Pro Ala Ala Gly Gly Ala Val His Thr Arg Gly
                165                 170                 175
Leu Asp Phe Ala Cys Asp Ile Tyr Ile Trp Ala Pro Leu Ala Gly Thr
            180                 185                 190
Cys Gly Val Leu Leu Leu Ser Leu Val Ile Thr Leu Tyr Lys Arg Gly
            195                 200                 205
Arg Lys Lys Leu Leu Tyr Ile Phe Lys Gln Pro Phe Met Arg Pro Val
        210                 215                 220
Gln Thr Thr Gln Glu Glu Asp Gly Cys Ser Cys Arg Phe Pro Glu Glu
225                 230                 235                 240
Glu Glu Gly Gly Cys Glu Leu Gly Gly Arg Val Lys Phe Ser Arg
                245                 250                 255
Ser Ala Asp Ala Pro Ala Tyr Gln Gln Gly Gln Asn Gln Leu Tyr Asn
            260                 265                 270
Glu Leu Asn Leu Gly Arg Arg Glu Glu Tyr Asp Val Leu Asp Lys Arg
        275                 280                 285
Arg Gly Arg Asp Pro Glu Met Gly Gly Lys Pro Arg Arg Lys Asn Pro
    290                 295                 300
Gln Glu Gly Leu Tyr Asn Glu Leu Gln Lys Asp Lys Met Ala Glu Ala
305                 310                 315                 320
Tyr Ser Glu Ile Gly Met Lys Gly Glu Arg Arg Arg Gly Lys Gly His
                325                 330                 335
Asp Gly Leu Tyr Gln Gly Leu Ser Thr Ala Thr Lys Asp Thr Tyr Asp
            340                 345                 350
Ala Leu His Met Gln Ala Leu Pro Pro Arg
            355                 360

<210> SEQ ID NO 32
<211> LENGTH: 410
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Leu Leu Leu Val Thr Ser Leu Leu Leu Cys Glu Leu Pro His Pro
1               5                   10                  15
```

```
Ala Phe Leu Leu Ile Pro Gly Pro Val Pro Pro Ser Thr Ala Leu Arg
             20                  25                  30

Tyr Leu Ile Glu Glu Leu Val Asn Ile Thr Gln Asn Gln Lys Ala Pro
         35                  40                  45

Leu Cys Asn Gly Ser Met Val Trp Ser Ile Asn Leu Thr Ala Gly Met
     50                  55                  60

Tyr Cys Ala Ala Leu Glu Ser Leu Ile Asn Val Ser Gly Cys Ser Ala
 65                  70                  75                  80

Ile Glu Lys Thr Gln Arg Met Leu Ser Gly Phe Cys Pro His Lys Val
                 85                  90                  95

Ser Ala Gly Gln Phe Ser Ser Leu His Val Arg Asp Thr Lys Ile Glu
             100                 105                 110

Val Ala Gln Phe Val Lys Asp Leu Leu Leu His Leu Lys Lys Leu Phe
         115                 120                 125

Arg Glu Gly Arg Phe Asn Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                 165                 170                 175

Leu Asp Phe Ala Cys Asp Phe Trp Val Leu Val Val Val Gly Gly Val
             180                 185                 190

Leu Ala Cys Tyr Ser Leu Leu Val Thr Val Ala Phe Ile Ile Phe Trp
         195                 200                 205

Val Arg Ser Lys Arg Ser Arg Gly Gly His Ser Asp Tyr Met Asn Met
     210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser Gly Gly Gly Lys Arg Gly
                 245                 250                 255

Arg Lys Lys Leu Leu Tyr Ile Phe Lys Gln Pro Phe Met Arg Pro Val
             260                 265                 270

Gln Thr Thr Gln Glu Glu Asp Gly Cys Ser Cys Arg Phe Pro Glu Glu
         275                 280                 285

Glu Glu Gly Gly Cys Glu Leu Gly Gly Gly Arg Val Lys Phe Ser Arg
     290                 295                 300

Ser Ala Asp Ala Pro Ala Tyr Gln Gln Gly Gln Asn Gln Leu Tyr Asn
305                 310                 315                 320

Glu Leu Asn Leu Gly Arg Arg Glu Glu Tyr Asp Val Leu Asp Lys Arg
                 325                 330                 335

Arg Gly Arg Asp Pro Glu Met Gly Gly Lys Pro Arg Arg Lys Asn Pro
             340                 345                 350

Gln Glu Gly Leu Tyr Asn Glu Leu Gln Lys Asp Lys Met Ala Glu Ala
         355                 360                 365

Tyr Ser Glu Ile Gly Met Lys Gly Glu Arg Arg Arg Gly Lys Gly His
     370                 375                 380

Asp Gly Leu Tyr Gln Gly Leu Ser Thr Ala Thr Lys Asp Thr Tyr Asp
385                 390                 395                 400

Ala Leu His Met Gln Ala Leu Pro Pro Arg
                 405                 410

<210> SEQ ID NO 33
<211> LENGTH: 442
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Leu Leu Leu Val Thr Ser Leu Leu Cys Glu Leu Pro His Pro
1               5                   10                  15

Ala Phe Leu Leu Ile Pro Gly Pro Val Pro Pro Ser Thr Ala Leu Arg
                20                  25                  30

Tyr Leu Ile Glu Glu Leu Val Asn Ile Thr Gln Asn Gln Lys Ala Pro
                35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
                100                 105                 110

Val Ala Gln Phe Val Lys Asp Leu Leu Leu His Leu Lys Lys Leu Phe
                115                 120                 125

Arg Glu Gly Arg Phe Asn Glu Ser Lys Tyr Gly Pro Pro Cys Pro Pro
                130                 135                 140

Cys Pro Gly Gly Ser Ser Gly Gly Ser Gly Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
                180                 185                 190

Ile Ala Val Glu Trp Glu Ser Asn Gly Gln Pro Glu Asn Asn Tyr Lys
                195                 200                 205

Thr Thr Pro Pro Val Leu Asp Ser Asp Gly Ser Phe Phe Leu Tyr Ser
                210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Leu Gly Lys Met Ala Leu Ile Val Leu Gly Gly Val
                260                 265                 270

Ala Gly Leu Leu Leu Phe Ile Gly Leu Gly Ile Phe Phe Lys Arg Gly
                275                 280                 285

Arg Lys Lys Leu Leu Tyr Ile Phe Lys Gln Pro Phe Met Arg Pro Val
                290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Gly Gly Gly Arg Val Lys Phe Ser Arg
                325                 330                 335

Ser Ala Asp Ala Pro Ala Tyr Gln Gln Gly Gln Asn Gln Leu Tyr Asn
                340                 345                 350

Glu Leu Asn Leu Gly Arg Arg Glu Glu Tyr Asp Val Leu Asp Lys Arg
                355                 360                 365

Arg Gly Arg Asp Pro Glu Met Gly Gly Lys Pro Arg Arg Lys Asn Pro
```

```
                    370                 375                 380
Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
        435                 440

<210> SEQ ID NO 34
<211> LENGTH: 541
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
130                 135                 140

Cys Pro Ala Pro Glu Phe Glu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Gln Ser Thr Tyr Arg Val Val Ser Val Leu Thr Val
210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285
```

Tyr Pro Ser Asp Ile Ala Val Glu Trp Glu Ser Asn Gly Gln Pro Glu
290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
            325                 330                 335

Asn Val Phe Ser Cys Ser Val Met His Glu Ala Leu His Asn His Tyr
                340                 345                 350

Thr Gln Lys Ser Leu Ser Leu Ser Leu Gly Lys Ile Tyr Ile Trp Ala
            355                 360                 365

Pro Leu Ala Gly Thr Cys Gly Val Leu Leu Leu Ser Leu Val Ile Thr
        370                 375                 380

Lys Arg Gly Arg Lys Lys Leu Leu Tyr Ile Phe Lys Gln Pro Phe Met
385                 390                 395                 400

Arg Pro Val Gln Thr Thr Gln Glu Glu Asp Gly Cys Ser Cys Arg Phe
                405                 410                 415

Pro Glu Glu Glu Glu Gly Gly Cys Glu Leu Gly Gly Gly Arg Val Lys
                    420                 425                 430

Phe Ser Arg Ser Ala Asp Ala Pro Ala Tyr Gln Gln Gly Gln Asn Gln
            435                 440                 445

Leu Tyr Asn Glu Leu Asn Leu Gly Arg Arg Glu Glu Tyr Asp Val Leu
    450                 455                 460

Asp Lys Arg Arg Gly Arg Asp Pro Glu Met Gly Gly Lys Pro Arg Arg
465                 470                 475                 480

Lys Asn Pro Gln Glu Gly Leu Tyr Asn Glu Leu Gln Lys Asp Lys Met
                485                 490                 495

Ala Glu Ala Tyr Ser Glu Ile Gly Met Lys Gly Glu Arg Arg Arg Gly
                500                 505                 510

Lys Gly His Asp Gly Leu Tyr Gln Gly Leu Ser Thr Ala Thr Lys Asp
        515                 520                 525

Thr Tyr Asp Ala Leu His Met Gln Ala Leu Pro Pro Arg
    530                 535                 540

<210> SEQ ID NO 35
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 35

Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Gly Gly Ser Ser Gly Gly Gly Ser Gly
    130                 135                 140

Met Phe Trp Val Leu Val Val Gly Gly Val Leu Ala Cys Tyr Ser
145                 150                 155                 160

Leu Leu Val Thr Val Ala Phe Ile Ile Phe Trp Val Arg Ser Lys Arg
                165                 170                 175

Ser Arg Gly Gly His Ser Asp Tyr Met Asn Met Thr Pro Arg Arg Pro
            180                 185                 190

Gly Pro Thr Arg Lys His Tyr Gln Pro Tyr Ala Pro Pro Arg Asp Phe
        195                 200                 205

Ala Ala Tyr Arg Ser Gly Gly Gly Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Gly Gly Gly Arg Val Lys Phe Ser Arg Ser Ala Asp Ala Pro
            260                 265                 270

Ala Tyr Gln Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370

<210> SEQ ID NO 36
<211> LENGTH: 385
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Leu Leu Leu Val Thr Ser Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala

```
            65                  70                  75                  80
        Ile Glu Lys Thr Gln Arg Met Leu Ser Gly Phe Cys Pro His Lys Val
                        85                  90                  95

Ser Ala Gly Gln Phe Ser Ser Leu His Val Arg Asp Thr Lys Ile Glu
                    100                 105                 110

Val Ala Gln Phe Val Lys Asp Leu Leu Leu His Leu Lys Lys Leu Phe
                    115                 120                 125

Arg Glu Gly Arg Phe Asn Glu Ser Lys Tyr Gly Pro Pro Cys Pro Pro
                    130                 135                 140

Cys Pro Gly Gly Gly Ser Ser Gly Gly Ser Gly Met Phe Trp Val
        145                 150                 155                 160

Leu Val Val Val Gly Val Leu Ala Cys Tyr Ser Leu Leu Val Thr
                        165                 170                 175

Val Ala Phe Ile Ile Phe Trp Val Arg Ser Lys Arg Ser Arg Gly Gly
                    180                 185                 190

His Ser Asp Tyr Met Asn Met Thr Pro Arg Arg Pro Gly Pro Thr Arg
                    195                 200                 205

Lys His Tyr Gln Pro Tyr Ala Pro Pro Arg Asp Phe Ala Ala Tyr Arg
                    210                 215                 220

Ser Gly Gly Gly Lys Arg Gly Arg Lys Lys Leu Leu Tyr Ile Phe Lys
        225                 230                 235                 240

Gln Pro Phe Met Arg Pro Val Gln Thr Thr Gln Glu Glu Asp Gly Cys
                        245                 250                 255

Ser Cys Arg Phe Pro Glu Glu Glu Glu Gly Gly Cys Glu Leu Gly Gly
                    260                 265                 270

Gly Arg Val Lys Phe Ser Arg Ser Ala Asp Ala Pro Ala Tyr Gln Gln
                    275                 280                 285

Gly Gln Asn Gln Leu Tyr Asn Glu Leu Asn Leu Gly Arg Arg Glu Glu
                    290                 295                 300

Tyr Asp Val Leu Asp Lys Arg Arg Gly Arg Asp Pro Glu Met Gly Gly
        305                 310                 315                 320

Lys Pro Arg Arg Lys Asn Pro Gln Glu Gly Leu Tyr Asn Glu Leu Gln
                        325                 330                 335

Lys Asp Lys Met Ala Glu Ala Tyr Ser Glu Ile Gly Met Lys Gly Glu
                    340                 345                 350

Arg Arg Arg Gly Lys Gly His Asp Gly Leu Tyr Gln Gly Leu Ser Thr
                    355                 360                 365

Ala Thr Lys Asp Thr Tyr Asp Ala Leu His Met Gln Ala Leu Pro Pro
                    370                 375                 380

Arg
        385

<210> SEQ ID NO 37
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
            20                  25                  30
```

-continued

```
Tyr Leu Ile Glu Glu Leu Val Asn Ile Thr Gln Asn Gln Lys Ala Pro
             35                  40                  45

Leu Cys Asn Gly Ser Met Val Trp Ser Ile Asn Leu Thr Ala Gly Met
 50                  55                  60

Tyr Cys Ala Ala Leu Glu Ser Leu Ile Asn Val Ser Gly Cys Ser Ala
 65                  70                  75                  80

Ile Glu Lys Thr Gln Arg Met Leu Ser Gly Phe Cys Pro His Lys Val
                 85                  90                  95

Ser Ala Gly Gln Phe Ser Ser Leu His Val Arg Asp Thr Lys Ile Glu
                100                 105                 110

Val Ala Gln Phe Val Lys Asp Leu Leu Leu His Leu Lys Lys Leu Phe
            115                 120                 125

Arg Glu Gly Arg Phe Asn Glu Ser Lys Tyr Gly Pro Pro Cys Pro Pro
        130                 135                 140

Cys Pro Gly Gly Gly Ser Ser Gly Gly Ser Gly Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Val Leu Asp Ser Asp Gly Ser Phe Phe Leu Tyr Ser
210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Leu Gly Lys Met Phe Trp Val Leu Val Val Val Gly
            260                 265                 270

Gly Val Leu Ala Cys Tyr Ser Leu Leu Val Thr Val Ala Phe Ile Ile
        275                 280                 285

Phe Trp Val Arg Ser Lys Arg Ser Arg Gly Gly His Ser Asp Tyr Met
290                 295                 300

Asn Met Thr Pro Arg Arg Pro Gly Pro Thr Arg Lys His Tyr Gln Pro
305                 310                 315                 320

Tyr Ala Pro Pro Arg Asp Phe Ala Ala Tyr Arg Ser Gly Gly Gly Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Gly Gly Gly Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445
```

```
Glu Ala Tyr Ser Glu Ile Gly Met Lys Gly Glu Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 38
<211> LENGTH: 592
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
                20                  25                  30

Tyr Leu Ile Glu Glu Leu Val Asn Ile Thr Gln Asn Gln Lys Ala Pro
                35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
                100                 105                 110

Val Ala Gln Phe Val Lys Asp Leu Leu Leu His Leu Lys Lys Leu Phe
                115                 120                 125

Arg Glu Gly Arg Phe Asn Glu Ser Lys Tyr Gly Pro Pro Cys Pro Pro
                130                 135                 140

Cys Pro Ala Pro Glu Phe Glu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
                180                 185                 190

Trp Tyr Val Asp Gly Val Glu Val His Asn Ala Lys Thr Lys Pro Arg
                195                 200                 205

Glu Glu Gln Phe Gln Ser Thr Tyr Arg Val Val Ser Val Leu Thr Val
                210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
                260                 265                 270

Glu Met Thr Lys Asn Gln Val Ser Leu Thr Cys Leu Val Lys Gly Phe
                275                 280                 285

Tyr Pro Ser Asp Ile Ala Val Glu Trp Glu Ser Asn Gly Gln Pro Glu
                290                 295                 300

Asn Asn Tyr Lys Thr Thr Pro Pro Val Leu Asp Ser Asp Gly Ser Phe
```

```
            305                 310                 315                 320
        Phe Leu Tyr Ser Arg Leu Thr Val Asp Lys Ser Arg Trp Gln Glu Gly
                        325                 330                 335

Asn Val Phe Ser Cys Ser Val Met His Glu Ala Leu His Asn His Tyr
                        340                 345                 350

Thr Gln Lys Ser Leu Ser Leu Ser Leu Gly Lys Met Phe Trp Val Leu
                        355                 360                 365

Val Val Val Gly Gly Val Leu Ala Cys Tyr Ser Leu Leu Val Thr Val
                        370                 375                 380

Ala Phe Ile Ile Phe Trp Val Arg Ser Lys Ser Arg Gly His
        385                 390                 395                 400

Ser Asp Tyr Met Asn Met Thr Pro Arg Arg Pro Gly Pro Thr Arg Lys
                        405                 410                 415

His Tyr Gln Pro Tyr Ala Pro Pro Arg Asp Phe Ala Ala Tyr Arg Ser
                        420                 425                 430

Gly Gly Gly Lys Arg Gly Arg Lys Lys Leu Leu Tyr Ile Phe Lys Gln
                        435                 440                 445

Pro Phe Met Arg Pro Val Gln Thr Thr Gln Glu Glu Asp Gly Cys Ser
                        450                 455                 460

Cys Arg Phe Pro Glu Glu Glu Gly Gly Cys Glu Leu Gly Gly Gly
        465                 470                 475                 480

Arg Val Lys Phe Ser Arg Ser Ala Asp Ala Pro Ala Tyr Gln Gln Gly
                        485                 490                 495

Gln Asn Gln Leu Tyr Asn Glu Leu Asn Leu Gly Arg Arg Glu Glu Tyr
                        500                 505                 510

Asp Val Leu Asp Lys Arg Arg Gly Arg Asp Pro Glu Met Gly Gly Lys
                        515                 520                 525

Pro Arg Arg Lys Asn Pro Gln Glu Gly Leu Tyr Asn Glu Leu Gln Lys
                        530                 535                 540

Asp Lys Met Ala Glu Ala Tyr Ser Glu Ile Gly Met Lys Gly Glu Arg
        545                 550                 555                 560

Arg Arg Gly Lys Gly His Asp Gly Leu Tyr Gln Gly Leu Ser Thr Ala
                        565                 570                 575

Thr Lys Asp Thr Tyr Asp Ala Leu His Met Gln Ala Leu Pro Pro Arg
                        580                 585                 590

<210> SEQ ID NO 39
<211> LENGTH: 340
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gly Pro Val Pro Pro Ser Thr Ala Leu Arg Tyr Leu Ile Glu Glu Leu
        1               5                   10                  15

Val Asn Ile Thr Gln Asn Gln Lys Ala Pro Leu Cys Asn Gly Ser Met
                        20                  25                  30

Val Trp Ser Ile Asn Leu Thr Ala Gly Met Tyr Cys Ala Ala Leu Glu
                        35                  40                  45

Ser Leu Ile Asn Val Ser Gly Cys Ser Ala Ile Glu Lys Thr Gln Arg
                        50                  55                  60

Met Leu Ser Gly Phe Cys Pro His Lys Val Ser Ala Gly Gln Phe Ser
        65                  70                  75                  80
```

```
Ser Leu His Val Arg Asp Thr Lys Ile Glu Val Ala Gln Phe Val Lys
                85                  90                  95

Asp Leu Leu His Leu Lys Lys Leu Phe Arg Glu Gly Arg Phe Asn
            100                 105                 110

Ala Lys Pro Thr Thr Thr Pro Ala Pro Arg Pro Pro Thr Pro Ala Pro
        115                 120                 125

Thr Ile Ala Ser Gln Pro Leu Ser Leu Arg Pro Glu Ala Cys Arg Pro
130                 135                 140

Ala Ala Gly Gly Ala Val His Thr Arg Gly Leu Asp Phe Ala Cys Asp
145                 150                 155                 160

Ile Tyr Ile Trp Ala Pro Leu Ala Gly Thr Cys Gly Val Leu Leu Leu
                165                 170                 175

Ser Leu Val Ile Thr Leu Tyr Lys Arg Gly Arg Lys Lys Leu Leu Tyr
            180                 185                 190

Ile Phe Lys Gln Pro Phe Met Arg Pro Val Gln Thr Thr Gln Glu Glu
        195                 200                 205

Asp Gly Cys Ser Cys Arg Phe Pro Glu Glu Glu Glu Gly Gly Cys Glu
210                 215                 220

Leu Gly Gly Gly Arg Val Lys Phe Ser Arg Ser Ala Asp Ala Pro Ala
225                 230                 235                 240

Tyr Gln Gln Gly Gln Asn Gln Leu Tyr Asn Glu Leu Asn Leu Gly Arg
                245                 250                 255

Arg Glu Glu Tyr Asp Val Leu Asp Lys Arg Arg Gly Arg Asp Pro Glu
            260                 265                 270

Met Gly Gly Lys Pro Arg Arg Lys Asn Pro Gln Glu Gly Leu Tyr Asn
        275                 280                 285

Glu Leu Gln Lys Asp Lys Met Ala Glu Ala Tyr Ser Glu Ile Gly Met
290                 295                 300

Lys Gly Glu Arg Arg Arg Gly Lys Gly His Asp Gly Leu Tyr Gln Gly
305                 310                 315                 320

Leu Ser Thr Ala Thr Lys Asp Thr Tyr Asp Ala Leu His Met Gln Ala
                325                 330                 335

Leu Pro Pro Arg
            340

<210> SEQ ID NO 40
<211> LENGTH: 388
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80
```

```
Ser Leu His Val Arg Asp Thr Lys Ile Glu Val Ala Gln Phe Val Lys
            85                  90                  95

Asp Leu Leu Leu His Leu Lys Lys Leu Phe Arg Glu Gly Arg Phe Asn
        100                 105                 110

Ala Lys Pro Thr Thr Pro Ala Pro Arg Pro Pro Thr Pro Ala Pro
        115                 120                 125

Thr Ile Ala Ser Gln Pro Leu Ser Leu Arg Pro Glu Ala Cys Arg Pro
        130                 135                 140

Ala Ala Gly Gly Ala Val His Thr Arg Gly Leu Asp Phe Ala Cys Asp
145                 150                 155                 160

Phe Trp Val Leu Val Val Gly Gly Val Leu Ala Cys Tyr Ser Leu
                165                 170                 175

Leu Val Thr Val Ala Phe Ile Ile Phe Trp Val Arg Ser Lys Arg Ser
            180                 185                 190

Arg Gly Gly His Ser Asp Tyr Met Asn Met Thr Pro Arg Arg Pro Gly
        195                 200                 205

Pro Thr Arg Lys His Tyr Gln Pro Tyr Ala Pro Pro Arg Asp Phe Ala
        210                 215                 220

Ala Tyr Arg Ser Gly Gly Gly Lys Arg Gly Arg Lys Lys Leu Leu Tyr
225                 230                 235                 240

Ile Phe Lys Gln Pro Phe Met Arg Pro Val Gln Thr Thr Gln Glu Glu
                245                 250                 255

Asp Gly Cys Ser Cys Arg Phe Pro Glu Glu Glu Glu Gly Gly Cys Glu
            260                 265                 270

Leu Gly Gly Gly Arg Val Lys Phe Ser Arg Ser Ala Asp Ala Pro Ala
        275                 280                 285

Tyr Gln Gln Gly Gln Asn Gln Leu Tyr Asn Glu Leu Asn Leu Gly Arg
        290                 295                 300

Arg Glu Glu Tyr Asp Val Leu Asp Lys Arg Arg Gly Arg Asp Pro Glu
305                 310                 315                 320

Met Gly Gly Lys Pro Arg Arg Lys Asn Pro Gln Glu Gly Leu Tyr Asn
                325                 330                 335

Glu Leu Gln Lys Asp Lys Met Ala Glu Ala Tyr Ser Glu Ile Gly Met
            340                 345                 350

Lys Gly Glu Arg Arg Arg Gly Lys Gly His Asp Gly Leu Tyr Gln Gly
        355                 360                 365

Leu Ser Thr Ala Thr Lys Asp Thr Tyr Asp Ala Leu His Met Gln Ala
        370                 375                 380

Leu Pro Pro Arg
385

<210> SEQ ID NO 41
<211> LENGTH: 420
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
```

```
            35                  40                  45
Ser Leu Ile Asn Val Ser Gly Cys Ser Ala Ile Glu Lys Thr Gln Arg
 50                  55                  60

Met Leu Ser Gly Phe Cys Pro His Lys Val Ser Ala Gly Gln Phe Ser
 65                  70                  75                  80

Ser Leu His Val Arg Asp Thr Lys Ile Glu Val Ala Gln Phe Val Lys
                 85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Gly Gly Gly Ser
        115                 120                 125

Ser Gly Gly Gly Ser Gly Gly Gln Pro Arg Glu Pro Gln Val Tyr Thr
130                 135                 140

Leu Pro Pro Ser Gln Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Arg Leu Thr Val Asp Lys
        195                 200                 205

Ser Arg Trp Gln Glu Gly Asn Val Phe Ser Cys Ser Val Met His Glu
210                 215                 220

Ala Leu His Asn His Tyr Thr Gln Lys Ser Leu Ser Leu Ser Leu Gly
225                 230                 235                 240

Lys Met Ala Leu Ile Val Leu Gly Gly Val Ala Gly Leu Leu Leu Phe
                245                 250                 255

Ile Gly Leu Gly Ile Phe Phe Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
290                 295                 300

Leu Gly Gly Gly Arg Val Lys Phe Ser Arg Ser Ala Asp Ala Pro Ala
305                 310                 315                 320

Tyr Gln Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

Met Gly Gly Lys Pro Arg Arg Lys Asn Pro Gln Glu Gly Leu Tyr Asn
        355                 360                 365

Glu Leu Gln Lys Asp Lys Met Ala Glu Ala Tyr Ser Glu Ile Gly Met
370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
            420

<210> SEQ ID NO 42
<211> LENGTH: 519
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 42

```
Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Ala Pro Glu Phe
        115                 120                 125

Glu Gly Gly Pro Ser Val Phe Leu Phe Pro Pro Lys Pro Lys Asp Thr
130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Gly Leu Pro Ser
    210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Arg Leu
    290                 295                 300

Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Leu Gly Lys Ile Tyr Ile Trp Ala Pro Leu Ala Gly Thr Cys
            340                 345                 350

Gly Val Leu Leu Leu Ser Leu Val Ile Thr Lys Arg Gly Arg Lys Lys
        355                 360                 365

Leu Leu Tyr Ile Phe Lys Gln Pro Phe Met Arg Pro Val Gln Thr Thr
    370                 375                 380
```

-continued

```
Gln Glu Glu Asp Gly Cys Ser Cys Arg Phe Pro Glu Glu Glu Gly
385                 390                 395                 400

Gly Cys Glu Leu Gly Gly Gly Arg Val Lys Phe Ser Arg Ser Ala Asp
            405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Gly Arg
            435                 440                 445

Asp Pro Glu Met Gly Gly Lys Pro Arg Arg Lys Asn Pro Gln Glu Gly
450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Gly Lys Gly His Asp Gly Leu
            485                 490                 495

Tyr Gln Gly Leu Ser Thr Ala Thr Lys Asp Thr Tyr Asp Ala Leu His
            500                 505                 510

Met Gln Ala Leu Pro Pro Arg
            515
```

<210> SEQ ID NO 43
<211> LENGTH: 351
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

```
Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
            85                  90                  95

Asp Leu Leu Leu His Leu Lys Lys Leu Phe Arg Glu Gly Arg Phe Asn
            100                 105                 110

Gly Gly Gly Ser Ser Gly Gly Ser Gly Met Phe Trp Val Leu Val
            115                 120                 125

Val Val Gly Gly Val Leu Ala Cys Tyr Ser Leu Leu Val Thr Val Ala
130                 135                 140

Phe Ile Ile Phe Trp Val Arg Ser Lys Arg Ser Arg Gly Gly His Ser
145                 150                 155                 160

Asp Tyr Met Asn Met Thr Pro Arg Arg Pro Gly Pro Thr Arg Lys His
            165                 170                 175

Tyr Gln Pro Tyr Ala Pro Pro Arg Asp Phe Ala Ala Tyr Arg Ser Gly
            180                 185                 190

Gly Gly Lys Arg Gly Arg Lys Lys Leu Leu Tyr Ile Phe Lys Gln Pro
            195                 200                 205

Phe Met Arg Pro Val Gln Thr Thr Gln Glu Glu Asp Gly Cys Ser Cys
```

```
            210                 215                 220
Arg Phe Pro Glu Glu Glu Gly Gly Cys Glu Leu Gly Gly Gly Arg
225                 230                 235                 240

Val Lys Phe Ser Arg Ser Ala Asp Ala Pro Ala Tyr Gln Gln Gly Gln
                245                 250                 255

Asn Gln Leu Tyr Asn Glu Leu Asn Leu Gly Arg Arg Glu Glu Tyr Asp
                260                 265                 270

Val Leu Asp Lys Arg Arg Gly Arg Asp Pro Glu Met Gly Gly Lys Pro
                275                 280                 285

Arg Arg Lys Asn Pro Gln Glu Gly Leu Tyr Asn Glu Leu Gln Lys Asp
                290                 295                 300

Lys Met Ala Glu Ala Tyr Ser Glu Ile Gly Met Lys Gly Glu Arg Arg
305                 310                 315                 320

Arg Gly Lys Gly His Asp Gly Leu Tyr Gln Gly Leu Ser Thr Ala Thr
                325                 330                 335

Lys Asp Thr Tyr Asp Ala Leu His Met Gln Ala Leu Pro Pro Arg
                340                 345                 350

<210> SEQ ID NO 44
<211> LENGTH: 363
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
                100                 105                 110

Glu Ser Lys Tyr Gly Pro Pro Cys Pro Pro Cys Pro Gly Gly Gly Ser
            115                 120                 125

Ser Gly Gly Gly Ser Gly Met Phe Trp Val Leu Val Val Val Gly Gly
    130                 135                 140

Val Leu Ala Cys Tyr Ser Leu Leu Val Thr Val Ala Phe Ile Ile Phe
145                 150                 155                 160

Trp Val Arg Ser Lys Arg Ser Arg Gly Gly His Ser Asp Tyr Met Asn
                165                 170                 175

Met Thr Pro Arg Arg Pro Gly Pro Thr Arg Lys His Tyr Gln Pro Tyr
                180                 185                 190

Ala Pro Pro Arg Asp Phe Ala Ala Tyr Arg Ser Gly Gly Gly Lys Arg
            195                 200                 205

Gly Arg Lys Lys Leu Leu Tyr Ile Phe Lys Gln Pro Phe Met Arg Pro
    210                 215                 220
```

```
Val Gln Thr Thr Gln Glu Asp Gly Cys Ser Cys Arg Phe Pro Glu
225                 230                 235                 240

Glu Glu Glu Gly Gly Cys Glu Leu Gly Gly Arg Val Lys Phe Ser
                245                 250                 255

Arg Ser Ala Asp Ala Pro Ala Tyr Gln Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
            355                 360

<210> SEQ ID NO 45
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
            85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Gly Gly Ser
            115                 120                 125

Ser Gly Gly Gly Ser Gly Gly Gln Pro Arg Glu Pro Gln Val Tyr Thr
    130                 135                 140

Leu Pro Pro Ser Gln Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Arg Leu Thr Val Asp Lys
            195                 200                 205
```

```
Ser Arg Trp Gln Glu Gly Asn Val Phe Ser Cys Ser Val Met His Glu
        210                 215                 220

Ala Leu His Asn His Tyr Thr Gln Lys Ser Leu Ser Leu Ser Leu Gly
225                 230                 235                 240

Lys Met Phe Trp Val Leu Val Val Gly Gly Val Leu Ala Cys Tyr
            245                 250                 255

Ser Leu Leu Val Thr Val Ala Phe Ile Ile Phe Trp Val Arg Ser Lys
        260                 265                 270

Arg Ser Arg Gly Gly His Ser Asp Tyr Met Asn Met Thr Pro Arg Arg
            275                 280                 285

Pro Gly Pro Thr Arg Lys His Tyr Gln Pro Tyr Ala Pro Pro Arg Asp
    290                 295                 300

Phe Ala Ala Tyr Arg Ser Gly Gly Gly Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Gly Gly Gly Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 46
<211> LENGTH: 570
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
```

```
                    85                  90                  95
Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Ala Pro Glu Phe
            115                 120                 125

Glu Gly Gly Pro Ser Val Phe Leu Phe Pro Pro Lys Pro Lys Asp Thr
            130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
            180                 185                 190

Thr Tyr Arg Val Val Ser Val Leu Thr Val Leu His Gln Asp Trp Leu
            195                 200                 205

Asn Gly Lys Glu Tyr Lys Cys Lys Val Ser Asn Lys Gly Leu Pro Ser
            210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
            275                 280                 285

Pro Pro Val Leu Asp Ser Asp Gly Ser Phe Phe Leu Tyr Ser Arg Leu
            290                 295                 300

Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Leu Gly Lys Met Phe Trp Val Leu Val Val Val Gly Gly Val
            340                 345                 350

Leu Ala Cys Tyr Ser Leu Leu Val Thr Val Ala Phe Ile Ile Phe Trp
            355                 360                 365

Val Arg Ser Lys Arg Ser Arg Gly Gly His Ser Asp Tyr Met Asn Met
            370                 375                 380

Thr Pro Arg Arg Pro Gly Pro Thr Arg Lys His Tyr Gln Pro Tyr Ala
385                 390                 395                 400

Pro Pro Arg Asp Phe Ala Ala Tyr Arg Ser Gly Gly Lys Arg Gly
                405                 410                 415

Arg Lys Lys Leu Leu Tyr Ile Phe Lys Gln Pro Phe Met Arg Pro Val
            420                 425                 430

Gln Thr Thr Gln Glu Glu Asp Gly Cys Ser Cys Arg Phe Pro Glu Glu
            435                 440                 445

Glu Glu Gly Gly Cys Glu Leu Gly Gly Gly Arg Val Lys Phe Ser Arg
            450                 455                 460

Ser Ala Asp Ala Pro Ala Tyr Gln Gln Gly Gln Asn Gln Leu Tyr Asn
465                 470                 475                 480

Glu Leu Asn Leu Gly Arg Arg Glu Glu Tyr Asp Val Leu Asp Lys Arg
                485                 490                 495

Arg Gly Arg Asp Pro Glu Met Gly Gly Lys Pro Arg Arg Lys Asn Pro
            500                 505                 510
```

-continued

```
Gln Glu Gly Leu Tyr Asn Glu Leu Gln Lys Asp Lys Met Ala Glu Ala
            515                 520                 525

Tyr Ser Glu Ile Gly Met Lys Gly Glu Arg Arg Gly Lys Gly His
        530                 535                 540

Asp Gly Leu Tyr Gln Gly Leu Ser Thr Ala Thr Lys Asp Thr Tyr Asp
545                 550                 555                 560

Ala Leu His Met Gln Ala Leu Pro Pro Arg
                565                 570

<210> SEQ ID NO 47
<211> LENGTH: 363
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Gly Gly Lys Arg
        195                 200                 205

Gly Arg Lys Lys Leu Leu Tyr Ile Phe Lys Gln Pro Phe Met Arg Pro
    210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu Gly Gly Gly Arg Val Lys Phe Ser
                245                 250                 255

Arg Ser Ala Asp Ala Pro Ala Tyr Gln Gln Gly Gln Asn Gln Leu Tyr
            260                 265                 270

Asn Glu Leu Asn Leu Gly Arg Arg Glu Glu Tyr Asp Val Leu Asp Lys
        275                 280                 285
```

```
Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
            355                 360
```

<210> SEQ ID NO 48
<211> LENGTH: 341
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Ala Lys Pro Thr Thr Thr Pro Ala Pro Arg Pro Pro Thr Pro Ala Pro
        115                 120                 125

Thr Ile Ala Ser Gln Pro Leu Ser Leu Arg Pro Glu Ala Cys Arg Pro
130                 135                 140

Ala Ala Gly Gly Ala Val His Thr Arg Gly Leu Asp Phe Ala Cys Asp
145                 150                 155                 160

Ile Tyr Ile Trp Ala Pro Leu Ala Gly Thr Cys Gly Val Leu Leu Leu
                165                 170                 175

Ser Leu Val Ile Thr Gly Gly Lys Arg Gly Arg Lys Lys Leu Leu
            180                 185                 190

Tyr Ile Phe Lys Gln Pro Phe Met Arg Pro Val Gln Thr Thr Gln Glu
        195                 200                 205

Glu Asp Gly Cys Ser Cys Arg Phe Pro Glu Glu Glu Gly Gly Cys
210                 215                 220

Glu Leu Gly Gly Gly Arg Val Lys Phe Ser Arg Ser Ala Asp Ala Pro
225                 230                 235                 240

Ala Tyr Gln Gln Gly Gln Asn Gln Leu Tyr Asn Glu Leu Asn Leu Gly
                245                 250                 255

Arg Arg Glu Glu Tyr Asp Val Leu Asp Lys Arg Arg Gly Arg Asp Pro
            260                 265                 270

Glu Met Gly Gly Lys Pro Arg Arg Lys Asn Pro Gln Glu Gly Leu Tyr
```

```
                275                 280                 285
Asn Glu Leu Gln Lys Asp Lys Met Ala Glu Ala Tyr Ser Glu Ile Gly
        290                 295                 300

Met Lys Gly Glu Arg Arg Gly Lys Gly His Asp Gly Leu Tyr Gln
305                 310                 315                 320

Gly Leu Ser Thr Ala Thr Lys Asp Thr Tyr Asp Ala Leu His Met Gln
                325                 330                 335

Ala Leu Pro Pro Arg
        340

<210> SEQ ID NO 49
<211> LENGTH: 112
<212> TYPE: PRT
<213> ORGANISM: Homo sapiens

<400> SEQUENCE: 49

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 50
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 51
<211> LENGTH: 229
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Ser Lys Tyr Gly Pro Pro Cys Pro Pro Cys Pro Ala Pro Glu Phe
1               5                  10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Glu Ser Lys Tyr Gly Pro Pro Cys Pro Ser Cys Pro
1               5                  10

<210> SEQ ID NO 53
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 53

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
        210                 215                 220

Leu Ser Leu Gly Lys
225

<210> SEQ ID NO 54
<211> LENGTH: 28
<212> TYPE: PRT
<213> ORGANISM: Homo sapiens

<400> SEQUENCE: 54

Met Phe Trp Val Leu Val Val Gly Gly Val Leu Ala Cys Tyr Ser
1               5                   10                  15

Leu Leu Val Thr Val Ala Phe Ile Ile Phe Trp Val
            20                  25
```

COSTIMULATORY CHIMERIC ANTIGEN RECEPTOR T CELLS TARGETING IL13Rα2

CLAIM OF PRIORITY

This application claims priority under 35 U.S.C. § 120 to U.S. patent application Ser. No. 15/167,869, filed on May 27, 2016, issued as U.S. Pat. No.: 9,914,909 which claims priority under 35 U.S.C. § 365(c) to International Patent Application PCT/US2015/051089, filed on Sep. 18, 2015, which claims priority under 35 U.S.C. § 119(e) to provisional U.S. Patent Application 62/053,068, filed on Sep. 19, 2014, the entire contents of each which are hereby incorporated by reference.

BACKGROUND

Tumor-specific T cell based immunotherapies, including therapies employing engineered T cells, have been investigated for anti-tumor treatment. In some cases the T cells used in such therapies do not remain active in vivo for a long enough period. In some cases, the tumor-specificity of the T cells is relatively low. Therefore, there is a need in the art for tumor-specific cancer therapies with longer term anti-tumor functioning.

Malignant gliomas (MG), which include anaplastic astrocytoma (AA-grade III) and glioblastoma (GBM-grade IV), have an incidence rate of approximately 20,000 new cases diagnosed annually in the United States. According to the American Brain Tumor Association total prevalence of individuals living with a malignant brain tumor, based on United States 2010 census data, is roughly 140,000 persons. Although MG is a rare disease, it is highly aggressive and heterogeneous with respect to its malignant behavior and nearly uniformly lethal. Current standard-of-care therapies for high-grade MG yield only short term benefits, and these brain tumors are virtually incurable. Indeed, even with modern surgical and radiotherapeutic techniques, which often exacerbate the already severe morbidities imposed by location in the central nervous system (CNS), the 5-year survival rates are quite low. Furthermore, for the majority of patients who relapse with disease, there are few therapeutic options. Thus, there is a significant need for more effective therapies, particularly for those patients that have recurred/progressed following frontline therapies, and participation of this patient population in clinical trials is warranted.

Adoptive T cell therapy (ACT) utilizing chimeric antigen receptor (CAR) engineered T cells may provide a safe and effective way to reduce recurrence rates of MG, since CAR T cells can be engineered to specifically recognize antigenically-distinct tumor populations (Cartellieri et al. 2010 *J Biomed Biotechnol* 2010:956304; Ahmed et al. 2010 *Clin Cancer Res* 16:474; Sampson et al. 2014 *Clin Cancer Res* 20:972; Brown et al. 2013 *Clin Cancer Res* 2012 18:2199; Chow et al. 2013 *Mol Ther* 21:629), and T cells can migrate through the brain parenchyma to target and kill infiltrative malignant cells (Hong et al. 2010 *Clin Cancer Res* 16:4892; Brown et al. 2007 *J Immunol* 179:3332; Hong et al. 2010 *Clin Cancer Res* 16:4892; Yaghoubi 2009 *Nat Clin PRact Oncol* 6:53). Preclinical studies have demonstrated that IL13Rα2-targeting CAR+ T cells exhibit potent major histocompatibility complex (MHC)-independent, IL13Rα2-specific cytolytic activity against both stem-like and differentiated glioma cells, and induce regression of established glioma xenografts in vivo (Kahlon et al. 2004 *Cancer Res* 64:9160; Brown et al. 2012 *Clin Cancer Res* 18:2199).

SUMMARY

Described herein are chimeric transmembrane immunoreceptors (chimeric antigen receptors or "CARs") which comprise an extracellular domain, a transmembrane region and an intracellular signaling domain. The extracellular domain is made up of an IL-13 ligand that binds interleukin-13Rα2 (IL13Rα2) and, optionally, a spacer, comprising, for example a portion human Fc domain. The transmembrane portion includes a CD4 transmembrane domain, a CD8 transmembrane domain, a CD28 transmembrane domain, a CD3 transmembrane domain or a 4IBB transmembrane domain. The intracellular signaling domain includes the signaling domain from the zeta chain of the human CD3 complex (CD3ζ) and one or more costimulatory domains, e.g., a 4-1BB costimulatory domain. The extracellular domain enables the CAR, when expressed on the surface of a T cell, to direct T cell activity to those cells expressing IL13Rα2, a receptor expressed on the surface of tumor cells, including glioma. Importantly, the IL13Rα2 binding portion of the CAR includes an amino acid modification, such as an E13Y mutation, that increases binding specificity. The inclusion of a costimulatory domain, such as the 4-1BB (CD137) costimulatory domain in series with CD3ζ in the intracellular region enables the T cell to receive co-stimulatory signals. T cells, for example, patient-specific, autologous T cells can be engineered to express the CARs described herein and the engineered cells can be expanded and used in ACT. Various T cell subsets can be used. In addition, the CAR can be expressed in other immune cells such as NK cells. Where a patient is treated with an immune cell expressing a CAR described herein the cell can be an autologous or allogenic T cell. In some cases the cells used are CD4+ and CD8+ central memory T cells ($T_{CM}$), which are CD45RO+CD62L+, and the use of such cells can improve long-term persistence of the cells after adoptive transfer compared to the use of other types of patient-specific T cells.

Described herein is a nucleic acid molecule encoding a chimeric antigen receptor (CAR)r, wherein the chimeric antigen receptor comprises: human IL-13 or a variant thereof having 1-10 (e.g., 1 or 2) amino acid modifications; a transmembrane domain selected from: a CD4 transmembrane domain or variant thereof having 1-10 (e.g., 1 or 2) amino acid modifications, a CD8 transmembrane domain or variant thereof having 1-10 (e.g., 1 or 2) amino acid modifications, a CD28 transmembrane domain or a variant thereof having 1-10 (e.g., 1 or 2) amino acid modifications, and a CD3ζ transmembrane domain or a variant thereof having 1-10 (e.g., 1 or 2) amino acid modifications; a costimulatory domain; and CD3 ζ signaling domain of a variant thereof having 1-10 (e.g., 1 or 2) amino acid modifications.

In various embodiments the costimulatory domain is selected from the group consisting of: a CD28 costimulatory domain or a variant thereof having 1-10 (e.g., 1 or 2) amino acid modifications, a 4-IBB costimulatory domain or a variant thereof having 1-10 (e.g., 1 or 2) amino acid modifications and an OX40 costimulatory domain or a variant thereof having 1-10 (e.g., 1 or 2) amino acid modifications. In certain embodiments, a 4IBB costimulatory domain or a variant thereof having 1-10 (e.g., 1 or 2) amino acid modifications in present.

Additional embodiment the CAR comprises: a variant of a human IL13 having 1-10 amino acid modification that increase binding specificity for IL13Rα2 versus IL13Rα1; the human IL-13 or variant thereof is an IL-13 variant comprising the amino acid sequence of SEQ ID NO:3 with 1 to 5 amino acid modifications, provided that the amino acid at position 11 of SEQ ID NO:3 other than E; two different costimulatory domains selected from the group consisting of: a CD28 costimulatory domain or a variant thereof having 1-10 (e.g., 1 or 2) amino acid modifications, a 4IBB costimulatory domain or a variant thereof having 1-10 (e.g., 1 or 2) amino acid modifications and an OX40 costimulatory domain or a variant thereof having 1-10 (e.g., 1 or 2) amino acid modifications; two different costimulatory domains selected from the group consisting of: a CD28 costimulatory domain or a variant thereof having 1-2 amino acid modifications, a 4IBB costimulatory domain or a variant thereof having 1-2 amino acid modifications and an OX40 costimulatory domain or a variant thereof having 1-2 amino acid modifications; human IL-13 or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3ζ transmembrane domain or a variant thereof having 1-2 amino acid modifications; a costimulatory domain; and CD3ζ signaling domain of a variant thereof having 1-2 amino acid modifications; a spacer region located between the IL-13 or variant thereof and the transmembrane domain (e.g., the spacer region comprises an amino acid sequence selected from the group consisting of SEQ ID NO: 4, 14-20, 50 and 52); the spacer comprises an IgG hinge region; the spacer region comprises 10-150 amino acids; the 4-1BB signaling domain comprises the amino acid sequence of SEQ ID NO:6; the CD3ζ signaling domain comprises the amino acid sequence of SEQ ID NO:7; and a linker of 3 to 15 amino acids that is located between the costimulatory domain and the CD3 ζ signaling domain or variant thereof. In certain embodiments where there are two costimulatory domains, one is an 4-IBB costimulatory domain and the other a costimulatory domain selected from: CD28 and CD28gg In some embodiments: nucleic acid molecule expresses a polypeptide comprising an amino acid sequence selected from SEQ ID NOs: 10, 31-48 and 52; the chimeric antigen receptor comprises a IL-13/IgG4/CD4t/41-BB region comprising the amino acid of SEQ ID NO:11 and a CD3 ζ signaling domain comprising the amino acid sequence of SEQ ID NO:7; and the chimeric antigen receptor comprises the amino acid sequence of SEQ ID NOs: 10, 31-48 and 52.

Also disclosed is a population of human T cells transduced by a vector comprising an expression cassette encoding a chimeric antigen receptor, wherein chimeric antigen receptor comprises: human IL-13 or a variant thereof having 1-10 amino acid modifications; a transmembrane domain selected from: a CD4 transmembrane domain or variant thereof having 1-10 amino acid modifications, a CD8 transmembrane domain or variant thereof having 1-10 amino acid modifications, a CD28 transmembrane domain or a variant thereof having 1-10 amino acid modifications, and a CD3ζ transmembrane domain or a variant thereof having 1-10 amino acid modifications; a costimulatory domain; and CD3 ζ signaling domain of a variant thereof having 1-10 amino acid modifications. In various embodiments: the population of human T cells comprise a vector expressing a chimeric antigen receptor comprising an amino acid sequence selected from SEQ ID NOs: 10, 31-48 and 52; the population of human T cells are comprises of central memory T cells (Tcm cells) (e.g., at least 20%, 30%, 40%, 50% 60%, 70%, 80% of the cells are Tcm cells; at least 15%, 20%, 25%, 30%, 35% of the Tcm cells are CD4+ and at least 15%, 20%, 25%, 30%, 35% of the Tcm cells are CD8+ cells).

Also described is a method of treating cancer in a patient comprising administering a population of autologous or allogeneic human T cells (e.g., autologous or allogenic T cells comprising Tcm cells, e.g., at least 20%, 30%, 40%, 50% 60%, 70%, 80% of the cells are Tcm cells; at least 15%, 20%, 25%, 30%, 35% of the Tcm cells are CD4+ and at least 15%, 20%, 25%, 30%, 35% of the Tcm cells are CD8+ cells) transduced by a vector comprising an expression cassette encoding a chimeric antigen receptor, wherein chimeric antigen receptor comprises an amino acid sequence selected from SEQ ID NOs: 10, 31-48 and 52. In various embodiments: the population of human T cells comprise central memory T cells; the cancer is glioblastoma; and the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs: 10, 31-48 and 52.

Also described is: a nucleic acid molecule encoding an polypeptide comprising an amino acid sequence that is at least 95% identical to an amino acid sequence selected from SEQ ID NO:10 and SEQ ID NOs: 10, 31-48 and 52; a nucleic acid molecule encoding an polypeptide comprising an amino acid sequence that is identical to an amino acid sequence selected from SEQ ID NO: 10, 31-48 and 52 except for the presence of no more than 5 amino acid substitutions, deletions or insertions; a nucleic acid molecule encoding an polypeptide comprising an amino acid sequence that is identical to an amino acid sequence selected from SEQ ID NO:10 and SEQ ID NOs: 10, 31-48 and 52 except for the presence of no more than 5 amino acid substitutions; and a nucleic acid molecule encoding an polypeptide comprising an amino acid sequence that is identical to an amino acid sequence selected from SEQ ID NO:10 and SEQ ID NOs: 10, 31-48 and 52 except for the presence of no more than 2 amino acid substitutions.

Certain CAR described herein, for example, the IL13(EQ) BBζ CAR and the IL13(EQ)CD28-BBζ CAR, have certain beneficial characteristics compared to certain other IL13-targeted CAR. For example, they have improved selectivity for IL13Rα, elicit lower Th2 cytokine production, particularly lower IL13 production.

T cells expressing a CAR targeting IL13Rα2 can be useful in treatment of cancers such as glioblastoma, as well as other cancer that expresses IL13Rα2 which include but are not limited to medulloblastoma, breast cancer, head and neck cancer, kidney cancer, ovarian cancer and Kaposi's sarcoma. Thus, this disclosure includes methods for treating cancer using T cells expressing a CAR described herein.

This disclosure also nucleic acid molecules that encode any of the CARs described herein (e.g., vectors that include a nucleic acid sequence encoding one of the CARs) and isolated T lymphocytes that express any of the CARs described herein.

The CAR described herein can include a spacer region located between the IL13 domain and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 14) |
| IgG4 hinge (S→P) (S228P) | 12 aa | ESKYGPPCPPCP (SEQ ID NO: 15) |
| IgG4 hinge | 12 aa | ESKYGPPCPSCP (SEQ ID NO: 52) |
| IgG4 hinge + linker | 22 aa | ESKYGPPCPPCPGGGSSGGGSG (SEQ ID NO: 16) |
| CD28 hinge | 39 aa | IEVMYPPPYLDNEKSNGTIIHVKGKHL CPSPLFPGPSKP (SEQ ID NO: 17) |
| CD8 hinge-48 aa | 48 aa | AKPTTTPAPRPPTPAPTIASQPLSLRPE ACRPAAGGAVHTRGLDFACD (SEQ ID NO: 18) |
| CD8 hinge-45 aa | 45 aa | TTTPAPRPPTPAPTIASQPLSLRPEACR PAAGGAVHTRGLDFACD (SEQ ID NO: 19) |
| IgG4(HL-CH3) | 129 aa | ESKYGPPCPPCPGGGSSGGGSGGQPR EPQVYTLPPSQEEMTKNQVSLTCLVK GFYPSDIAVEWESNGQPENNYKTTPP VLDSDGSFFLYSRLTVDKSRWQEGNV FSCSVMHEALHNHYTQKSLSLSLGK (SEQ ID NO: 20) |
| IgG4(L235E, N297Q) | 229 aa | ESKYGPPCPSCPAPEFEGGPSVFLFPPK PKDTLMISRTPEVTCVVVDVSQEDPE VQFNWYVDGVEVHQAKTKPREEQFN STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 4) |
| IgG4(S228P, L235E, N297Q) | 229 aa | ESKYGPPCPPCPAPEFEGGPSVFLFPPK PKDTLMISRTPEVTCVVVDVSQEDPE VQFNWYVDGVEVHQAKTKPREEQFN STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 51) |
| IgG4(CH3) | 107 aa | GQPREPQVYTLPPSQEEMTKNQVSLT CLVKGFYPSDIAVEWESNGQPENNYK TTPPVLDSDGSFFLYSRLTVDKSRWQ EGNVFSCSVMHEALHNHYTQKSLSLS LGK (SEQ ID NO: 50) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one or more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In certain embodiments, the spacer is derived from an IgG1, IgG2, IgG3, or IgG4 that includes one or more amino acid residues substituted with an amino acid residue different from that present in an unmodified spacer. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof. In this numbering scheme, described in greater detail below, the first amino acid in the IgG4(L235E, N297Q) spacer in Table 1 is 219 and the first amino acid in the IgG4(HL-CH3) spacer in Table 1 is 219 as is the first amino acid in the IgG hinge sequence and the IgG4 hinge linker (HL) sequence in Table 1

In some embodiments, the modified spacer is derived from an IgG1, IgG2, IgG3, or IgG4 that includes, but is not limited to, one or more of the following amino acid residue substitutions: C220S, C226S, S228P, C229S, P230S, E233P, V234A, L234V, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331P, P331S, I332E, E333A, E333S, E333S, K334A, A339D, A339Q, P396L, or a combination thereof.

In certain embodiments, the modified spacer is derived from IgG4 region that includes one or more amino acid residues substituted with an amino acid residue different from that present in an unmodified region. The one or more substituted amino acid residues are selected from, but not limited to, one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified spacer is derived from an IgG4 region that includes, but is not limited to, one or more of the following amino acid residue substitutions: 220S, 226S, 228P, 229S, 230S, 233P, 234A, 234V, 234F, 234A, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified spacer is substituted with the above identified amino acids at the indicated position.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 Proc Natl Acad Sci USA 63:78-85).

A variety of transmembrane domains can be used in CAR directed against IL13Rα2. Table 2 includes examples of suitable transmembrane domains. Where a spacer domain is present, the transmembrane domain is located carboxy terminal to the spacer domain.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 21) |
| CD28 | NM_006139 | 27 aa | FWVLVVVGGVLACYSLLVTVAFIIFWV (SEQ ID NO: 22) |
| CD28 (M) | NM_006139 | 28 aa | MFWVLVVVGGVLACYSLLVTVAFIIFWV (SEQ ID NO: 22) |
| CD4 | M35160 | 22 aa | MALIVLGGVAGLLLFIGLGIFF (SEQ ID NO: 5) |
| CD8tm | NM_001768 | 21 aa | IYIWAPLAGTCGVLLLSLVIT (SEQ ID NO: 23) |
| CD8tm2 | NM_001768 | 23 aa | IYIWAPLAGTCGVLLLSLVITLY (SEQ ID NO: 24) |
| CD8tm3 | NM_001768 | 24 aa | IYIWAPLAGTCGVLLLSLVITLYC (SEQ ID NO: 25) |
| 41BB | NM_001561 | 27 aa | IISFFLALTSTALLFLLFFLTLRFSVV (SEQ ID NO: 26) |

Many of the CAR described herein include one or more (e.g., two) costimulatory domains. The costimulatory domain(s) are located between the transmembrane domain and the CD3ζ signaling domain. Table 3 includes examples of suitable costimulatory domains together with the sequence of the CD3ζ signaling domain.

TABLE 3

Examples of Costimulatory Domains

| Name | Accession | Length | Sequence |
|---|---|---|---|
| CD3ζ | J04132.1 | 113 aa | RVKFSRSADAPAYQQGQNQLYNELN LGRREEYDVLDKRRGRDPEMGGKPR RKNPQEGLYNELQKDKMAEAYSEIG MKGERRRGKGHDGLYQGLSTATKDT YDALHMQALPPR (SEQ ID NO: 49) |

TABLE 3-continued

Examples of Costimulatory Domains

| Name | Accession | Length | Sequence |
|---|---|---|---|
| CD28 | NM_006139 | 42 aa | RSKRSRLLHSDYMNMTPRRPGPTRK HYQPYAPPRDFAAYRS (SEQ ID NO: 27) |
| CD28gg* | NM_006139 | 42 aa | RSKRSRGGHSDYMNMTPRRPGPTRK HYQPYAPPRDFAAYRS (SEQ ID NO: 28) |
| 41BB | NM_001561 | 42 aa | KRGRKKLLYIFKQPFMRPVQTTQEE DGCSCRFPEEEEGGCEL (SEQ ID NO: 29) |
| OX40 | | 42 aa | ALYLLRRDQRLPPDAHKPPGGGSFR TPIQEEQADAHSTLAKI (SEQ ID NO: 30) |

DESCRIPTION OF DRAWINGS

FIG. 1 is a schematic depiction of IL13(E13Y)-zetakine CAR (Left) composed of the IL13Rα2-specific human IL-13 variant (huIL-13(E13Y)), human IgG4 Fc spacer (huγ4Fc), human CD4 transmembrane (huCD4 tm), and human CD3ζ chain cytoplasmic (huCD3ζ cyt) portions as indicated. Also depicted is a IL13(EQ)BBζ CAR which is the same as the IL13(E13Y)-zetakine with the exception of the two point mutations, L235E and N297Q indicated in red, that are located in the CH2 domain of the IgG4 spacer, and the addition of a costimulatory 4-1BB cytoplasmic domain (4-1BB cyt).

FIGS. 2A-C depict certain vectors an open reading frames. A is a diagram of the cDNA open reading frame of the 2670 nucleotide IL13(EQ)BBZ-T2ACD19t construct, where the IL13Rα2-specific ligand IL13(E13Y), IgG4(EQ) Fc hinge, CD4 transmembrane, 4-1BB cytoplasmic signaling, three-glycine linker, and CD3ζ cytoplasmic signaling domains of the IL13(EQ)BBZ CAR, as well as the T2A ribosome skip and truncated CD19 sequences are indicated. The human GM-CSF receptor alpha and CD19 signal sequences that drive surface expression of the IL13(EQ)BBζ CAR and CD19t are also indicated. B is a diagram of the sequences flanked by long terminal repeats (indicated by 'R') that will integrate into the host genome. C is a map of the IL13(EQ)BBZ-T2A-CD19t_epHIV7 plasmid.

FIGS. 6A-C depicts the results of flow cytometric analysis of surface transgene and T cell marker expression. IL13(EQ)BBζ/CD19t+ $T_{CM}$ HD006.5 and HD187.1 were co-stained with anti-IL13-PE and anti-CD8-FITC to detect CD8+ CAR+ and CD4+(i.e., CD8 negative) CAR+ cells (A), or anti-CD19-PE and anti-CD4-FITC to detect CD4+ CD19t+ and CD8+(i.e., CD4 negative) CAR+ cells (B). IL13(EQ)BBζ/CD19t+ $T_{CM}$ HD006.5 and HD187.1 stained with fluorochromeconjugatedanti-CD3, TCR, CD4, CD8, CD62L and CD28 (grey histograms) or isotype controls (black histograms) (C). In all cases the percentages based on viable lymphocytes (DAPI negative) stained above isotype.

FIGS. 14A-C depict the results of a series of studies evaluating costimulatory domains of IL13Rα2-specific CAR. Schematic of IL13Ra2-specific CAR constructs comparing various intracellular endo/signaling domains, including the first generation CD3z CAR lacking costimulation, versus second generation CARs incorporating either 4-1BB or CD28, versus a third generation CAR containing both CD28 and 41BB. All CAR cassettes also contain the T2A ribosomal skip and truncated CD19 (CD19t) sequences as a marker for transduced cells (A). CD4 and CD8 TCM were lentivirally transduced and CAR-expressing T cells were immunomagnetically enriched via anti-CD19. CD19 and IL13 (i.e., CAR) expression levels as measured by flow cytometry (B). Stability of each CAR construct was determined by dividing the CAR (IL13) mean fluorescence intensity (MFI) by that of the transduction marker (CD19t) (C). The 4-1BB containing CARs demonstrated the lowest expression levels as compared to the CD19t transduction marker.

FIGS. 16A-C depict the results of a series of studies of the in vivo efficacy of IL13Rα2-specific CARs. NSG mice received an intracranial injection of ffLuc+ PBT030-2 tumor cells on day 0, and were randomized into 6 groups (n=9-10 mice per group) for i.c. treatment with either PBS (Tumor Only), mock-transduced T cells or T cells expressing the indicated IL13Rα2-specific CAR on day 8. Quantitative bioluminescence imaging was then carried out to monitor tumor growth over time. Bioluminescence images for representative mice in each group (A). Mean+S.E. of total flux levels of luciferase activity over time in each group (B). Flux levels for each mouse at Day 27. All groups treated with IL13Rα2-specific CAR T cells, except those treated with T cells expressing the CD28-CAR, show statistically-significant reduction in tumor volume compared to mice treated with mock-transduced T cells (C)

FIGS. 17A-B depict the amino acid sequence of IL13 (EQ)BBζ/CD19t+(SEQ ID NO:10).

FIGS. 18A-O depict a sequence comparison of IL13(EQ) 41BBζ[IL13{EQ}41BBζ T2A-CD19t_epHIV7; pF02630] (SEQ ID NO:12) and CD19Rop_epHIV7 (pJ01683) (SEQ ID NO:13).

FIG. 19 depicts the amino acid sequence of IL13(EmY)-CD8h3-CD8tm2-41BB Zeta (SEQ ID NO:31 with GMSC-FRa signal peptide; SEQ ID NO:39 without GMSCFRa signal peptide).

FIG. 20 depicts the amino acid sequence of IL13(EmY)-CD8h3-CD28tm-CD28gg-41BB-Zeta (SEQ ID NO:32 with GMSCFRa signal peptide; SEQ ID NO:40 without GMSC-FRa signal peptide).

FIG. 21 depicts the amino acid sequence of IL13(EmY)-IgG4(HL-CH3)-CD4tm-41BB-Zeta (SEQ ID NO:33 with GMSCFRa signal peptide; SEQ ID NO:41 without GMSC-FRa signal peptide).

FIG. 22 depicts the amino acid sequence of IL13(EmY)-IgG4(L235E,N297Q)-CD8tm-41BB-Zeta (SEQ ID NO:34 with GMSCFRa signal peptide; SEQ ID NO:42 without GMSCFRa signal peptide).

FIG. 23 depicts the amino acid sequence of IL13(EmY)-Linker-CD28tm-CD28gg-41BB-Zeta (SEQ ID NO:35 with GMSCFRa signal peptide; SEQ ID NO:43 without GMSC-FRa signal peptide).

FIG. 24 depicts the amino acid sequence of IL13(EmY)-HL-CD28m-CD28gg-41BB-Zeta (SEQ ID NO:36 with GMSCFRa signal peptide; SEQ ID NO:44 without GMSC-FRa signal peptide).

FIG. 25 depicts the amino acid sequence of IL13(EmY)-IgG4(HL-CH3)-CD28tm-CD28gg-41BB-Zeta (SEQ ID NO:37 with GMSCFRa signal peptide; SEQ ID NO:45 without GMSCFRa signal peptide).

FIG. 26 depicts the amino acid sequence of IL13(EmY) IgG4(L235E,N297Q)-CD28tm-CD28gg-41BB-Zeta (SEQ ID NO:38 with GMSCFRa signal peptide; SEQ ID NO:46 without GMSCFRa signal peptide).

FIG. 27 depicts the amino acid sequence of IL13(EmY)-CD8h3-CD8tm-41BB Zeta (SEQ ID NO:47 with GMSC-FRa signal peptide; SEQ ID NO:48 without GMSCFRa signal peptide).

DETAILED DESCRIPTION

Figure 3:
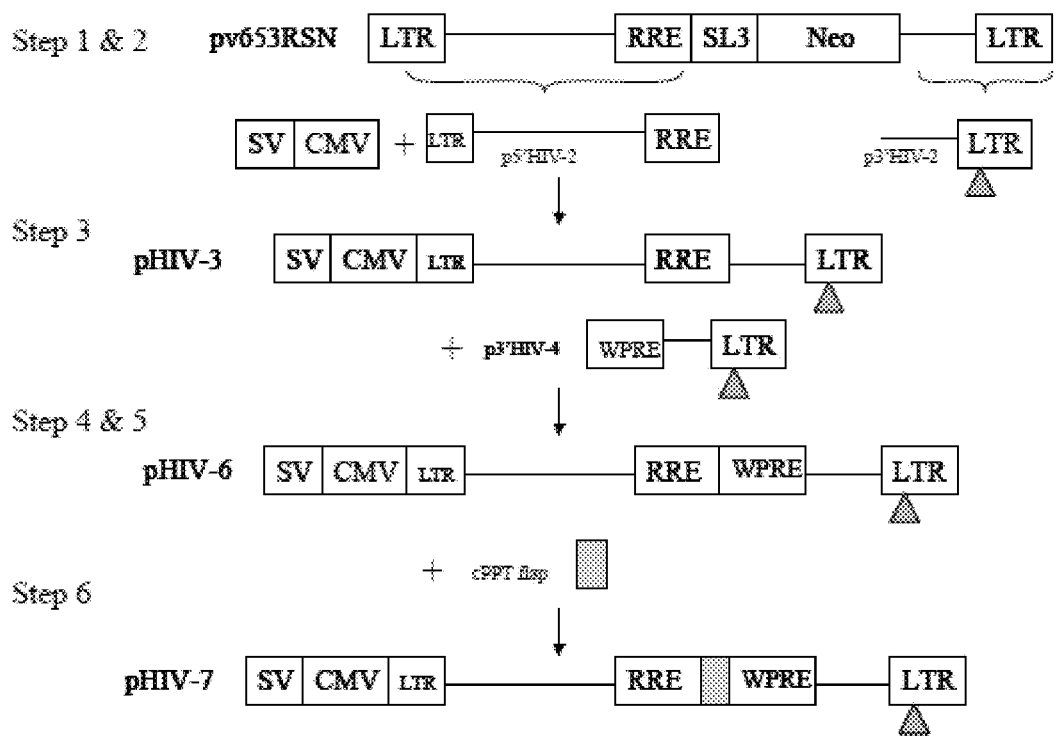
FIG. 3 depicts the construction of pHIV7.

Described below is the structure, construction and characterization of various IL13Rα2-specific chimeric antigen receptors. A chimeric antigen (CAR) is a recombinant biomolecule that contains, at a minimum, an extracellular recognition domain, a transmembrane region, and an intracellular signaling domain. The term "antigen," therefore, is not limited to molecules that bind antibodies, but to any molecule that can bind specifically to a target. For example, a CAR can include a ligand that specifically binds a cell surface receptor. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more costimulatory signaling domains. CARs can both to bind antigen and transduce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

One IL13Rα2-specific CAR described herein is referred to as IL13(EQ)BBζ. This CAR includes a variety of important features including: a IL13α2 ligand having an amino acid change that improves specificity of biding to IL13α2; the domain of CD137 (4-1BB) in series with CD3ζ to provide beneficial costimulation; and an IgG4 Fc region that is mutated at two sites within the CH2 region (L235E; N297Q) in a manner that reduces binding by Fc receptors (FcRs). Other CAR described herein contain a second costimulatory domain.

In some cases the CAR described herein, including the IL13(EQ)BBζ CAR can be produced using a vector in which the CAR open reading frame is followed by a T2A ribosome skip sequence and a truncated CD19 (CD19t), which lacks the cytoplasmic signaling tail (truncated at amino acid 323). In this arrangement, co-expression of CD19t provides an inert, non-immunogenic surface marker that allows for accurate measurement of gene modified cells, and enables positive selection of gene-modified cells, as well as efficient cell tracking and/or imaging of the therapeutic T cells in vivo following adoptive transfer. Co-expression of CD19t provides a marker for immunological targeting of the transduced cells in vivo using clinically available antibodies and/or immunotoxin reagents to selectively delete the therapeutic cells, and thereby functioning as a suicide switch.

Gliomas, express IL13 receptors, and in particular, high-affinity IL13 receptors. However, unlike the IL13 receptor, glioma cells overexpress a unique IL13Rα2 chain capable of binding IL13 independently of the requirement for IL4Rβ or γc44. Like its homolog IL4, IL13 has pleotropic immunoregulatory activity outside the CNS. Both IL13 and IL4 stimulate IgE production by B lymphocytes and suppress pro-inflammatory cytokine production by macrophages.

Detailed studies using autoradiography with radiolabeled IL13 have demonstrated abundant IL13 binding on nearly all malignant glioma tissues studied. This binding is highly homogeneous within tumor sections and in single cell analysis. However, molecular probe analysis specific for IL13Rα2 mRNA did not detect expression of the glioma-specific receptor by normal brain elements and autoradiography with radiolabeled IL13 also could not detect specific IL13 binding in the normal CNS. These studies suggest that the shared IL13Rα1/IL4β/γc receptor is not expressed detectably in the normal CNS. Therefore, IL13Rα2 is a very specific cell-surface target for glioma and is a suitable target for a CAR designed for treatment of a glioma.

Binding of IL13-based therapeutic molecules to the broadly expressed IL13Rα1/IL4β/γc receptor complex, however, has the potential of mediating undesired toxicities to normal tissues outside the CNS, and thus limits the systemic administration of these agents. An amino acid substitution in the IL13 alpha helix A at amino acid 13 of tyrosine for the native glutamic acid selectively reduces the affinity of IL13 to the IL13Rα1/IL4β/γc receptor. Binding of this mutant (termed IL13(E13Y)) to IL13Rα2, however, was increased relative to wild-type IL13. Thus, this minimally altered IL13 analog simultaneously increases IL13's specificity and affinity for glioma cells. Therefore, CAR described herein include an IL13 containing a mutation (E to Y or E to some other amino acid such as K or R or L or V) at amino acid 13 (according to the numbering of Debinski et al. 1999 *Clin Cancer Res* 5:3143s). IL13 having the natural sequence also may be used, however, and can be useful, particularly in situations where the modified T cells are to be locally administered, such as by injection directly into a tumor mass.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient, including unselected PBMC or enriched CD3 T cells or enriched CD3 or memory T cell subsets, can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a SIN lentiviral vector that directs the expression of an IL13Rα2-specific CAR (e.g., IL13(EQ)BBζ) as well as a truncated human CD19 (CD19t), a non-immunogenic surface marker for both in vivo detection and potential ex vivo selection. The activated/genetically modified central memory T cells can be expanded in vitro with IL-2/IL-15 and then cryopreserved.

Example 1: Construction and Structure of an IL13Rα2-Specific CAR

The structure of a useful IL13Rα2-specific CAR is described below. The codon optimized CAR sequence contains a membrane-tethered IL-13 ligand mutated at a single site (E13Y) to reduce potential binding to IL13Rα1, an IgG4 Fc spacer containing two mutations (L235E; N297Q) that greatly reduce Fc receptor-mediated recognition models, a CD4 transmembrane domain, a costimulatory 4-1BB cytoplasmic signaling domain, and a CD3ζ cytoplasmic signaling domain. A T2A ribosome skip sequence separates this IL13(EQ)BBζ CAR sequence from CD19t, an inert, non-immunogenic cell surface detection/selection marker. This T2A linkage results in the coordinate expression of both IL13(EQ)BBζ and CD19t from a single transcript. FIG. 2A is a schematic drawing of the 2670 nucleotide open reading frame encoding the IL13(EQ)BBZ-T2ACD19t construct. In this drawing, the IL13Rα2-specific ligand IL13(E13Y), IgG4(EQ) Fc, CD4 transmembrane, 4-1BB cytoplasmic signaling, three-glycine linker, and CD3ζ cytoplasmic signaling domains of the IL13(EQ)BBZ CAR, as well as the T2A ribosome skip and truncated CD19 sequences are all indicated. The human GM-CSF receptor alpha and CD19 signal sequences that drive surface expression of the IL13 (EQ)BBZ CAR and CD19t are also indicated. Thus, the IL13(EQ)BBZ-T2ACD19t construct includes a IL13Rα2-specific, hinge-optimized, costimulatory chimeric immunoreceptor sequence (designated IL13(EQ)BBZ), a ribosome-skip T2A sequence, and a CD19t sequence.

The IL13(EQ)BBZ sequence was generated by fusion of the human GM-CSF receptor alpha leader peptide with IL13(E13Y) ligand 5 L235E/N297Q-modified IgG4 Fc hinge (where the double mutation interferes with FcR recognition), CD4 transmembrane, 4-1BB cytoplasmic signaling domain, and CD3ζ cytoplasmic signaling domain sequences. This sequence was synthesized de novo after codon optimization. The T2A sequence was obtained from digestion of a T2A-containing plasmid. The CD19t sequence was obtained from that spanning the leader peptide sequence to the transmembrane components (i.e., basepairs 1-972) of a CD19-containing plasmid. All three fragments, 1) IL13 (EQ)BBZ, 2) T2A, and 3) CD19t, were cloned into the multiple cloning site of the epHIV7 lentiviral vector. When transfected into appropriate cells, the vector integrates the sequence depicted schematically in FIG. 2B into the host cells genome. FIG. 2C provides a schematic drawing of the 9515 basepair IL13(EQ)BBZ-T2A-CD19t_epHIV7 plasmid itself.

As shown schematically in FIG. 1, IL13(EQ)BBZ CAR differs in several important respects from a previously described IL13Rα2-specific CAR referred to as IL13 (E13Y)-zetakine (Brown et al. 2012 *Clinical Cancer Research* 18:2199). The IL13(E13Y)-zetakine is composed of the IL13Rα2-specific human IL-13 mutein (huIL-13 (E13Y)), human IgG4 Fc spacer (huγ4Fc), human CD4 transmembrane (huCD4 tm), and human CD3ζ chain cytoplasmic (huCD3ζ cyt) portions as indicated. In contrast, the IL13(EQ)BBζ) has two point mutations, L235E and N297Q that are located in the CH2 domain of the IgG4 spacer, and a costimulatory 4-1BB cytoplasmic domain (4-1BB cyt).

Example 2: Construction and Structure of epHIV7 Used for Expression of an IL13Rα2-Specific CAR The pHIV7 plasmid is the parent plasmid from which the clinical vector IL13(EQ)BBZ-T2A-CD19t_epHIV7 was derived in the T cell Therapeutics Research Laboratory (TCTRL) at City of Hope (COH). The epHIV7 vector used for expression of the CAR was produced from pHIV7 vector. Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository. The woodchuck post-transcriptional regulatory element (WPRE) sequence was previously described.

Construction of pHIV7 is schematically depicted in FIG. 3. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi Ψ, is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector), are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

Figure 4:
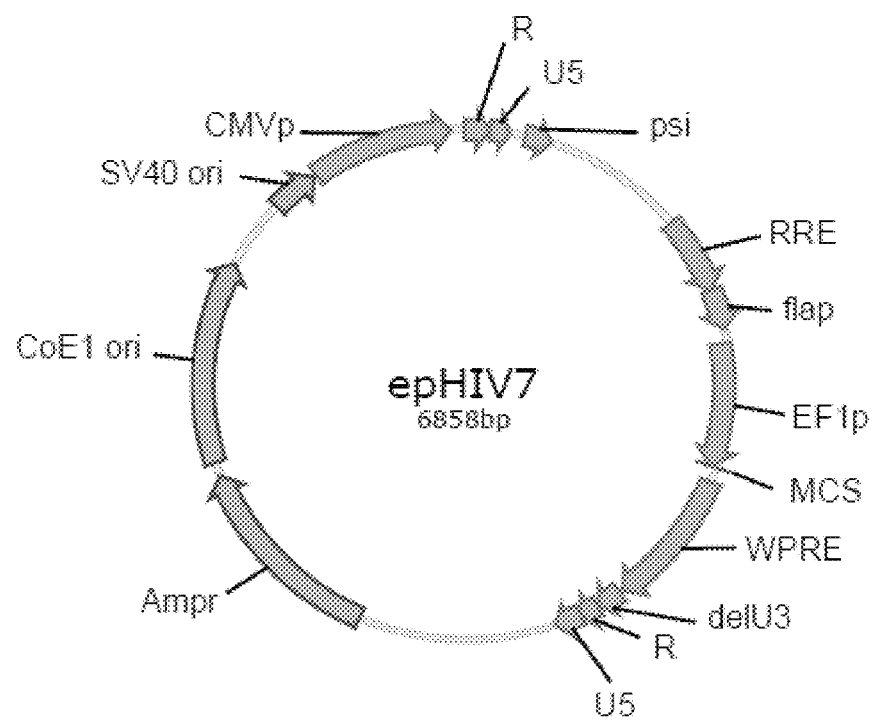
FIG. 4 depicts the elements of pHIV7.
Figure 5:
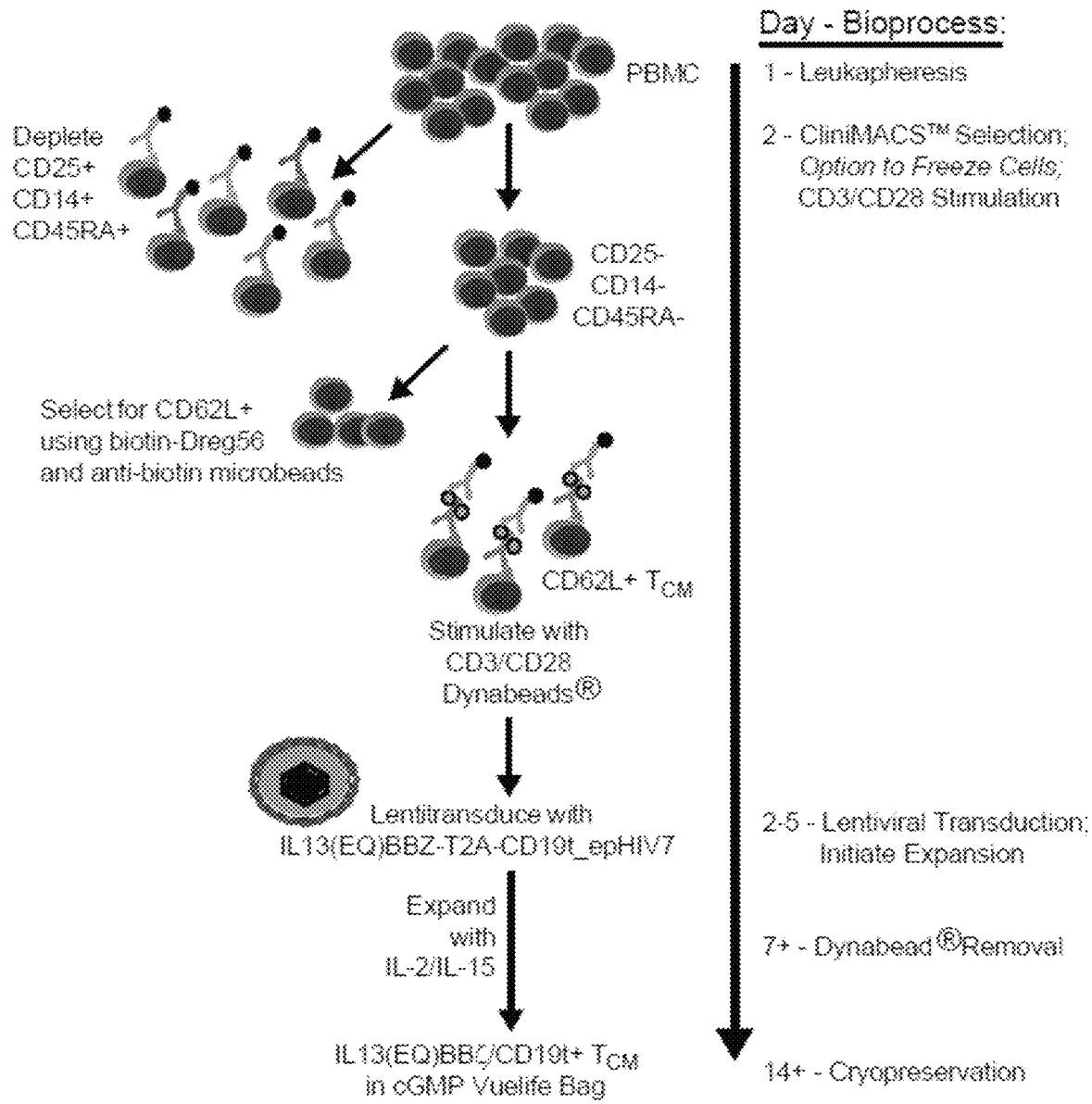
FIG. 5 depicts a production scheme for IL13(EQ)BBζ/CD19t+ $T_{CM}$.

The CMV promoter was replaced by the EF1α-HTLV promoter (EF1p), and the new plasmid was named epHIV7 (FIG. 4). The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, the IL13(EQ)BBZ-T2ACD19t_epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes (56). Table 4 summarizes the various regulator elements present in IL13(EQ)BBZ-T2ACD19t_epHIV7.

TABLE 4

Functional elements of IL13(EQ)41BBZ-T2A-CD19t_epHIV7

| Regulatory Elements and Genes | Location (Nucleotide Numbers) | Comments |
|---|---|---|
| U5 | 87-171 | 5' Unique sequence |
| psi | 233-345 | Packaging signal |
| RRE | 957-1289 | Rev-responsive element |
| flap | 1290-1466 | Contains polypurine track sequence and central termination sequence to facilitate nuclear import of pre-integration complex |
| EF1p Promoter | 1524-2067 | EF1-alpha Eukaryotic Promoter sequence driving expression of CD19Rop |
| IL13-IgG4 (EQ)-41BB-Zeta-T2A-CD19t | 2084-4753 | Therapeutic insert |
| WPRE | 4790-5390 | Woodchuck hepatitis virus derived regulatory element to enhance viral RNA transportation |
| delU3 | 5405-5509 | 3' U3 with deletion to generate SIN vector |
| R | 5510-5590 | Repeat sequence within LTR |
| U5 | 5591-5704 | 3' U5 sequence in LTR |
| $Amp^R$ | 6540-7398 | Ampicillin-resistance gene |
| CoE1 ori | 7461-8342 | Replication origin of plasmid |
| SV40 ori | 8639-8838 | Replication origin of SV40 |
| CMV promoter | 8852-9451 | CMV promoter to generate viral genome RNA |
| R | 9507-86 | Repeat sequence within LTR |

Example 3: Production of Vectors for Transduction of Patient T Cells

For each plasmid (IL13(EQ)BBZ-T2A-CD19t_epHIV7; pCgp; pCMV-G; and pCMV-Rev2), a seed bank is generated, which is used to inoculate the fermenter to produce sufficient quantities of plasmid DNA. The plasmid DNA is tested for identity, sterility and endotoxin prior to its use in producing lentiviral vector.

Briefly, cells were expanded from the 293T working cell (WCB), which has been tested to confirm sterility and the absence of viral contamination. A vial of 293T cells from the 293T WCB was thawed. Cells were grown and expanded until sufficient numbers of cells existed to plate an appropriate number of 10 layer cell factories (CFs) for vector production and cell train maintenance. A single train of cells can be used for production.

The lentiviral vector was produced in sub-batches of up to 10 CFs. Two sub-batches can be produced in the same week leading to the production of approximately 20 L of lentiviral supernatant/week. The material produced from all sub-batches were pooled during the downstream processing phase, in order to produce one lot of product. 293T cells were plated in CFs in 293T medium (DMEM with 10% FBS). Factories were placed in a 37° C. incubator and horizontally leveled in order to get an even distribution of the cells on all the layers of the CF. Two days later, cells were transfected with the four lentiviral plasmids described above using the CaPO4 method, which involves a mixture of Tris:EDTA, 2M CaCl2, 2×HBS, and the four DNA plasmids. Day 3 after transfection, the supernatant containing secreted lentiviral vectors was collected, purified and concentrated. After the supernatant was removed from the CFs, End-of-Production Cells were collected from each CF. Cells were trypsinized from each factory and collected by centrifugation. Cells were resuspended in freezing medium and cryopreserved. These cells were later used for replication-competent lentivirus (RCL) testing.

To purify and formulate vectors crude supernatant was clarified by membrane filtration to remove the cell debris. The host cell DNA and residual plasmid DNA were degraded by endonuclease digestion (Benzonase®). The viral supernatant was clarified of cellular debris using a 0.45 µm filter. The clarified supernatant was collected into a pre-weighed container into which the Benzonase® is added (final concentration 50 U/mL). The endonuclease digestion for residual plasmid DNA and host genomic DNA as performed at 37° C. for 6 h. The initial tangential flow ultra-filtration (TFF) concentration of the endonuclease-treated supernatant was used to remove residual low molecular weight components from the crude supernatant, while concentrating the virus ~20 fold. The clarified endonuclease-treated viral supernatant was circulated through a hollow fiber cartridge with a NMWCO of 500 kD at a flow rate designed to maintain the shear rate at ~4,000 sec-1 or less, while maximizing the flux rate. Diafiltration of the nuclease-treated supernatant was initiated during the concentration process to sustain the cartridge performance. An 80% permeate replacement rate was established, using 4% lactose in PBS as the diafiltration buffer. The viral supernatant was brought to the target volume, representing a 20-fold concentration of the crude supernatant, and the diafiltration was continued for 4 additional exchange volumes, with the permeate replacement rate at 100%.

Further concentration of the viral product was accomplished by using a high speed centrifugation technique. Each sub-batch of the lentivirus was pelleted using a Sorvall RC-26 plus centrifuge at 6000 RPM (6,088 RCF) at 6° C. for 16-20 h. The viral pellet from each sub-batch was then reconstituted in a 50 mL volume with 4% lactose in PBS. The reconstituted pellet in this buffer represents the final formulation for the virus preparation. The entire vector concentration process resulted in a 200-fold volume reduction, approximately. Following the completion of all of the sub-batches, the material was then placed at −80° C., while samples from each sub-batch were tested for sterility. Following confirmation of sample sterility, the sub-batches were rapidly thawed at 37° C. with frequent agitation. The material was then pooled and manually aliquoted in the Class II Type A/B3 biosafety cabinet in the viral vector suite. A fill configuration of 1 mL of the concentrated lentivirus in sterile USP class 6, externally threaded O-ring cryovials was used. Center for Applied Technology Development (CATD)'s Quality Systems (QS) at COH released all materials according to the Policies and Standard Operating Procedures for the CBG and in compliance with current Good Manufacturing Practices (cGMPs).

To ensure the purity of the lentiviral vector preparation, it was tested for residual host DNA contaminants, and the transfer of residual host and plasmid DNA. Among other tests, vector identity was evaluated by RT-PCR to ensure that the correct vector is present. All release criteria were met for the vector intended for use in this study.

Example 4: Preparation of T Cells Suitable for Use in ACT

T lymphocytes are obtained from a patient by leukopheresis, and the appropriate allogenic or autologous T cell subset, for example, Central Memory T cells ($T_{CM}$), are genetically altered to express the CAR, then administered back to the patient by any clinically acceptable means, to achieve anticancer therapy.

An outline of the manufacturing strategy for $T_{CM}$ is depicted in FIG. 8 (Manufacturing schema for IL13(EQ) BBζ/CD19t+ $T_{CM}$). Specifically, apheresis products obtained from consented research participants are ficolled, washed and incubated overnight. Cells are then depleted of monocyte, regulatory T cell and naïve T cell populations using GMP grade anti-CD14, anti-CD25 and anti-CD45RA reagents (Miltenyi Biotec) and the CliniMACS™ separation device. Following depletion, negative fraction cells are enriched for CD62L+$T_{CM}$ cells using DREG56-biotin (COH clinical grade) and anti-biotin microbeads (Miltenyi Biotec) on the CliniMACS™ separation device.

Following enrichment, $T_{CM}$ cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced with IL13(EQ)BBZ-T2A-CD19t_epHIV7 lentiviral vector at a multiplicity of infection (MOI) of 1.0 to 0.3. Cultures are maintained for up to 42 days with addition of complete X-Vivo15 and IL-2 and IL-15 cytokine as required for cell expansion (keeping cell density between $3 \times 10^5$ and $2 \times 10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium (Cryostore CS5, BioLife Solutions).

On the day(s) of T cell infusion, the cryopreserved and released product is thawed, washed and formulated for re-infusion. The cryopreserved vials containing the released cell product are removed from liquid nitrogen storage, thawed, cooled and washed with a PBS/2% human serum albumin (HSA) Wash Buffer. After centrifugation, the supernatant is removed and the cells resuspended in a Preservative-Free Normal Saline (PFNS)/2% HSA infusion diluent. Samples are removed for quality control testing.

Two qualification runs on cells procured from healthy donors were performed using the manufacturing platform described above. Each preclinical qualification run product was assigned a human donor (HD) number—HD006.5 and HD187.1. Importantly, as shown in Table 5, these qualification runs expanded >80 fold within 28 days and the expanded cells expressed the IL13(EQ)BBγ/CD19t transgenes.

TABLE 5

Summary of Expression Data from Pre-clinical Qualification Run Product

| Cell Product | CAR | CD19 | CD4+ | CD8+ | Fold Expansion |
|---|---|---|---|---|---|
| HD006.5 | 20% | 22% | 24% | 76% | 84-fold (28 days) |
| Hd187.1 | 18% | 25% | 37% | 63% | 259-fold (28 days) |

Example 5: Flow Cytometric Analysis of Surface Transgene and T Cell Marker Expression in IL13(EQ)BBγ/CD19t+ $T_{CM}$ The two preclinical qualification run products described in Example 4 were used in pre-clinical studies to as described below. FIGS. 6A-C depict the results of flow cytometric analysis of surface transgene and T cell marker expression. IL13(EQ)BBγ/CD19t+ $T_{CM}$ HD006.5 and HD187.1 were co-stained with anti-IL13-PE and anti-CD8-FITC to detect CD8+ CAR+ and CD4+(i.e., CD8 negative) CAR+ cells (FIG. 6A), or anti-CD19-PE and anti-CD4-FITC to detect CD4+CD19t+ and CD8+(i.e., CD4 negative) CAR+ cells (FIG. 6B). IL13(EQ)BBγ/CD19t+ $T_{CM}$ HD006.5 and HD187.1 were stained with fluorochrome-conjugated anti-CD3, TCR, CD4, CD8, CD62L and CD28 (grey histograms) or isotype controls (black histograms). (FIG. 6C). In each of FIGS. 6A-C, the percentages indicated are based on viable lymphocytes (DAPI negative) stained above isotype.

Example 6: Effector Activity of IL13(EQ)BBγ/CD19t+ $T_{CM}$

Figure 7A:
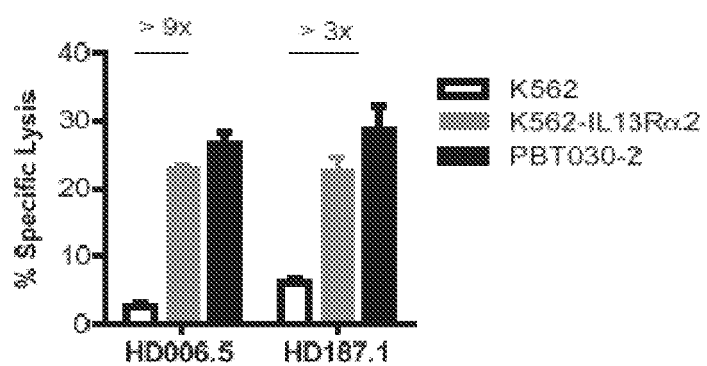
FIGS. 7A-B depict the in vitro functional characterization of IL13Rα2-specific effector function of IL13(EQ)BBZ+ $T_{CM}$. IL13(EQ)BBZ/CD19t+ $T_{CM}$ HD006.5 and HD187.1 were used as effectors in a 6-hour $^{51}$Cr release assay using a 10:1 E:T ratio based on CD19t expression. The IL13Rα2-positive tumor targets were K562 engineered to express IL13Rα2 (K562-IL13Rα2) and primary glioma line PBT030-2, and the IL13Rα2-negative tumor target control was K562 parental line (A). IL13(EQ)BBZ/CD19t+ $T_{CM}$ HD006.5 and HD187.1 were evaluated for antigen-dependent cytokine production following overnight co-culture at a 10:1 E:T ratio with IL13Rα2-positive and negative targets. Cytokine levels were measured using the Bio-Plex Pro Human Cytokine TH1/TH2 Assay kit and INF-γ are reported (B).
Figure 7B:
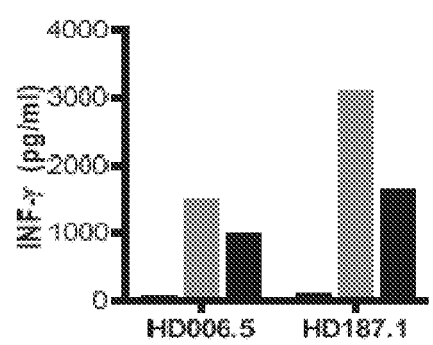

The effector activity of IL13(EQ)BBζ/CD19t+ $T_{CM}$ was assessed and the results of this analysis are depicted in FIGS. 7A-B. Briefly, IL13(EQ)BBγ/CD19t+ $T_{CM}$ HD006.5 and HD187.1 were used as effectors in a 6-hour 51Cr-release assay using a 10E:1T ratio based on CD19t expression. The IL13Rα2-positive tumor targets were K562 engineered to express IL13Rα2 (K562-IL13Rα2) and primary glioma line PBT030-2, and the IL13Rα2-negative tumor target control was the K562 parental line (FIG. 7A). IL13(EQ)BBγ/CD19t+HD006.5 and HD187.1 were evaluated for antigen-dependent cytokine production following overnight co-culture at a 10E:1T ratio with the same IL13Rα2-positive and negative targets as described in above. Cytokine levels were measured using the Bio-Plex Pro Human Cytokine TH1/TH2 Assay kit and INF-γ levels are depicted (FIG. 7B).

Example 7: In Vivo Anti-Tumor Activity of IL13(EQ)BBγ/CD19t+ $T_{CM}$

Figure 8A:
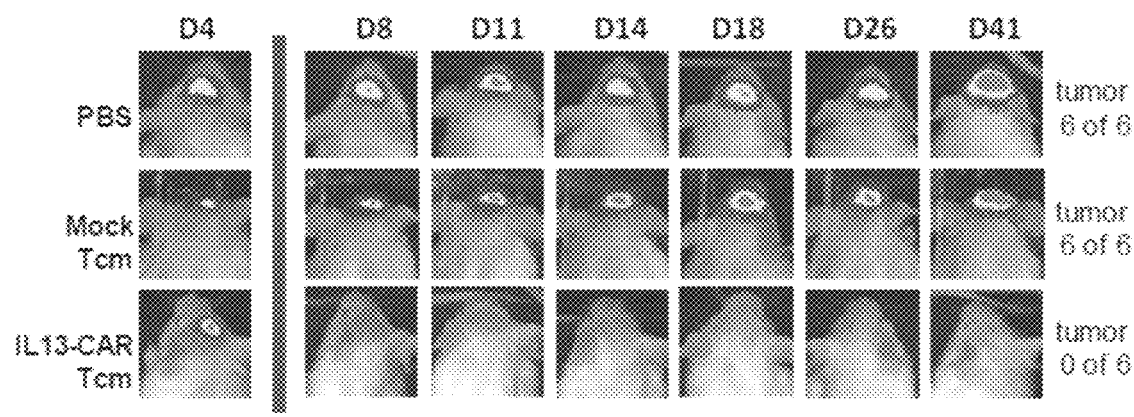
FIGS. 8A-C depict the result of studies demonstrating the regression of established glioma tumor xenografts after adoptive transfer of IL13(EQ)BBζ/CD19t+ $T_{CM}$. EGFP-ffLuc+ PBT030-2 tumor cells ($1 \times 10^5$) were stereotactically implanted into the right forebrain of NSG mice. On day 5, mice received either $2 \times 10^6$ IL13(EQ)BBζ/CD19t+ $T_{CM}$ ($1.1 \times 10^6$ CAR+; n=6), $2 \times 10^6$ mock $T_{CM}$ (no CAR; n=6) or PBS (n=6). Representative mice from each group showing relative tumor burden using Xenogen Living Image (A). Quantification of ffLuc flux (photons/sec) shows that IL13(EQ)BBζ/CD19t+ $T_{CM}$ induce tumor regression as compared to mock-transduced $T_{CM}$ and PBS (#p<0.02, *p<0.001, repeated measures ANOVA) (B). Kaplan Meier survival curve (n=6 per group) demonstrating significantly improved survival (p=0.0008; log-rank test) for mice treated with IL13(EQ)BBζ/CD19t+ $T_{CM}$ (C)
Figure 8B:
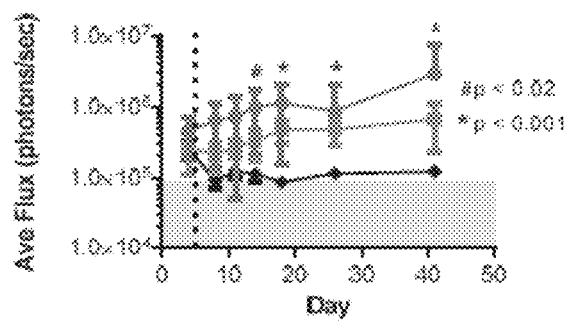
Figure 8C:
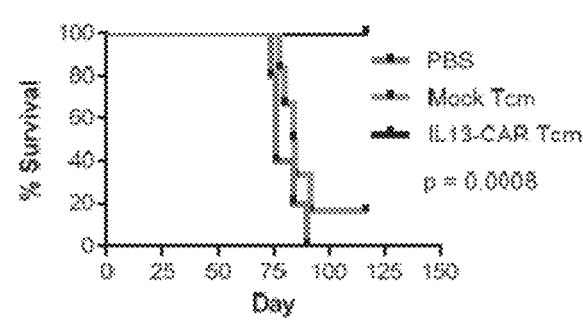

The studies described below demonstrate that IL13(EQ)BBγ/CD19t+ $T_{CM}$ exhibit anti-tumor efficacy in in vivo mouse models. Specifically, we have evaluated the anti-tumor potency of IL13(EQ)BBγ/CD19t+ $T_{CM}$ against the IL13Rα2+ primary low-passage glioblastoma tumor sphere line PBT030-2, which has been engineered to express both EGFP and firefly luciferase (ffLuc) reporter genes (PBT030-2 EGFP:ffLuc) A panel of primary lines (PBT) from patient glioblastoma specimens grown as tumor spheres (TSs) in serum-free media. These expanded TS lines exhibit stem cell-like characteristics, including expression of stem cell markers, multilineage differentiation and capacity to initiate orthotopic tumors in immunocompromised mice (NSG) at low cell numbers. The PBT030-2 EGFP:ffLuc TS-initiated xenograft model ($0.1 \times 10^6$ cells; 5 day engraftment) has been previously used to evaluate in vivo anti-tumor activity in NSG mice of IL13Rα2-specific CAR expressing T cells, whereby three injections of $2 \times 10^6$ cytolytic T lymphocytes (CTLs) over a course of 2 weeks were shown to reduce tumor growth. However, in those experiments the majority of the PBT030-2 tumors eventually recurred. By comparison, a single injection of IL13(EQ)BBγ/CD19t+ $T_{CM}$ ($1.1 \times 10^6$ CAR+$T_{CM}$; $2 \times 10^6$ total TCM) exhibited robust anti-tumor activity against PBT030-2 EGFP:ffLuc TS-initiated tumors ($0.1 \times 10^6$ cells; 5 day engraftment) as shown in FIGS. 8A-C. As compared to NSG mice treated with either PBS or mock transduced $T_{CM}$ (no CAR), IL13(EQ)BBγ/CD19t+ $T_{CM}$ significantly reduce ffLuc flux ($p<0.001$ at >18-days) and significantly improve survival ($p=0.0008$).

Briefly, EGFP-ffLuc+ PBT030-2 tumor cells ($1 \times 10^5$) were stereotactically implanted into the right forebrain of NSG mice. On day 5, mice received either $2 \times 10^6$ IL13(EQ)BBγ/CD19t+ $T_{CM}$ ($1.1 \times 106$ CAR+; n=6), $2 \times 10^6$ mock $T_{CM}$ (no CAR; n=6) or PBS (n=6). FIG. 8A depicts representative mice from each group showing relative tumor burden using Xenogen Living Image. Quantification of ffLuc flux (photons/sec) shows that IL13(EQ)BBζ/CD19t+ $T_{CM}$ induce tumor regression as compared to mock-transduced $T_{CM}$ and PBS (#p<0.02, *p<0.001, repeated measures ANOVA) (FIG. 8B). As shown in FIG. 8C, a Kaplan Meier survival curve (n=6 per group) demonstrates significantly improved survival (p=0.0008; log-rank test) for mice treated with IL13(EQ)BBγ/CD19t+ $T_{CM}$.

Example 8: Comparison of IL13(EQ)BBζ+ Tcm and Non-Tcm IL13-Zetakine CD8+ CTL Clones in Antitumor Efficacy and T Cell Persistence The studies described below compare IL13(EQ)BBζ+ Tcm and a previously created IL13Rα2-specific human CD8+ CTLs (IL13-zetakine CD8+ CTL (described in Brown et al. 2012 *Clin Cancer Res* 18:2199 and Kahlon et al. 2004 *Cancer Res* 64:9160). The IL13-zetakine uses a CD3ζ stimulatory domain, lacks a co-stimulatory domain and uses the same IL13 variant as IL13(EQ)BBζ+.

A panel of primary lines (PBT) from patient glioblastoma specimens grown as tumor spheres (TSs) in serum-free media was generated (Brown et al. 2012 *Clin Cancer Res* 18:2199; Brown et al. 2009 *Cancer Res* 69:8886). These expanded TS lines exhibit stem cell-like characteristics, including expression of stem cell markers, multi-lineage differentiation and capacity to initiate orthotopic tumors in immunocompromised mice (NSG) at low cell numbers. The IL13Rα2+ primary low-passage glioblastoma TS line PBT030-2, which has been engineered to express both EGFP and firefly luciferase (ffLuc) reporter genes (PBT030-2 EGFP:ffLuc) (Brown et al. 2012 *Clin Cancer Res* 18:2199) was used for the experiments outlined below.

Figure 9A:
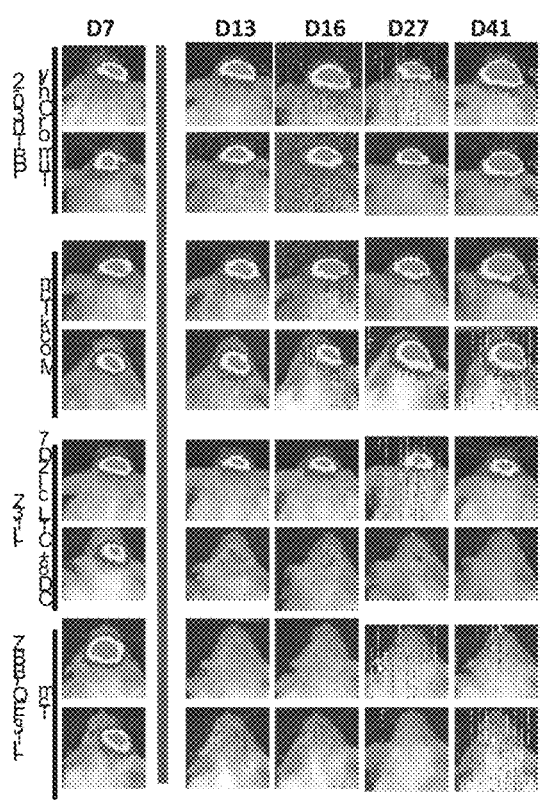
FIGS. 9A-C depict the results of studies comparing ant-tumor efficacy of IL13(EQ)BBZ $T_{CM}$ and IL13-zetakine CTL clones. EGFP-ffLuc+ PBT030-2 TSs ($1 \times 10^5$) were stereotactically implanted into the right forebrain of NSG mice. On day 8, mice received either $1.6 \times 10^6$ mock $T_{CM}$ (no CAR), $1.0 \times 10^6$ CAR+IL13(EQ)BBζ $T_{CM}$ ($1.6 \times 10^6$ total T cells; 63% CAR), $1.0 \times 10^6$ IL13-zetakine CD8+ CTL cl. 2D7 (clonal CAR+), or no treatment (n=6 per group). Representative mice from each group showing relative tumor burden using Xenogen Living Image (A). Linear regression lines of natural log of ffLuc flux (photons/sec) over time, P-values are for group by time interaction comparisons (B). Kaplan Meier survival analysis (n=6 per group) demonstrate significantly improved survival (p=0.02; log-rank test) for mice treated with IL13(EQ)BBζ $T_{CM}$ as compared to IL13-zetakine CD8+ CTL cl. 2D7 (C).
Figure 9B:
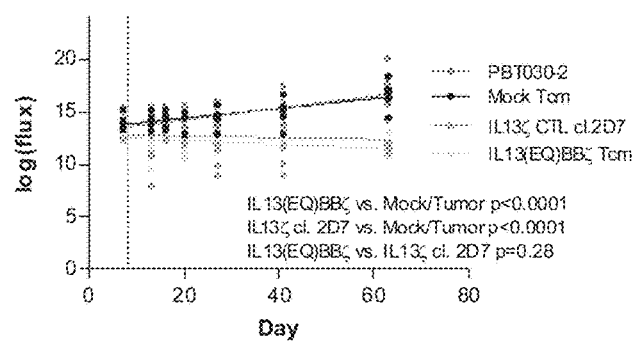
Figure 9C:
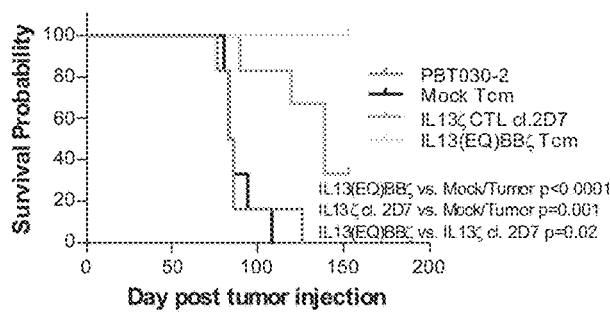

First, a single dose ($1 \times 10^6$ CAR T cells) of IL13(EQ)BBζ+Tcm product was compared to IL13-zetakine CD8+ CTL clones evaluated against day 8 PBT030-2 EGFP:ffuc TS-initiated xenografts ($0.1 \times 10^6$ cells). While both IL13Rα2-specific CAR T cells (IL13-zetakine CTL and IL13(EQ)BBζ Tcm) demonstrated antitumor activity against established PBT030-2 tumors as compared to untreated and mock Tcm (CAR-negative) controls (FIGS. 9A and 9B), IL13(EQ)BBZ+Tcm mediated significantly improved survival and durable tumor remission with mice living >150 days as compared to our first-generation IL13-zetakine CD8+ CTL clones (FIG. 9C).

Figure 10A:
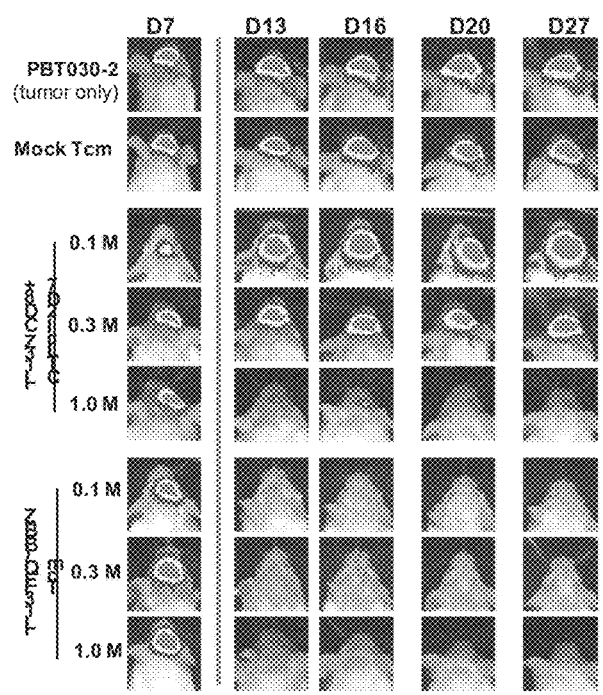
FIGS. 10A-C depict the results of studies comparing ant-tumor efficacy of IL13(EQ)BBζ $T_{CM}$ and IL13-zetakine CTL clones. EGFP-ffLuc+ PBT030-2 TSs ($1 \times 10^5$) were stereotactically implanted into the right forebrain of NSG mice. On day 8, mice received either $1.3 \times 10^6$ mock $T_{CM}$ (no CAR; n=6), 1.0, 0.3 or $0.1 \times 10^6$ CAR+IL13(EQ)BBζ $T_{CM}$ (78% CAR+; n=6-7), 1.0, 0.3 or $0.1 \times 10^6$ IL13-zetakine CD8+ CTL cl. 2D7 (clonal CAR+; n=6-7), or no treatment (n=5). Xenogen imaging of representative mice from each group showing relative tumor burden (A). Linear regression lines of natural log of ffLuc flux (photons/sec) shows that IL13(EQ)BBζ $T_{CM}$ achieve superior tumor regression as compared to first-generation IL13-zetakine CTL cl. 2D7, mock $T_{CM}$ and tumor only (B). Average flux per group at day 27 post tumor injection demonstrating that the $0.1 \times 10^6$ IL13(EQ)BBζ $T_{CM}$ dose outperforms the ten-fold higher $1.0 \times 10^6$ dose of IL13-zetakine CD8+ CTL cl. 2D7 (p=0.043; Welch two sample t-test) (C).
Figure 10B:
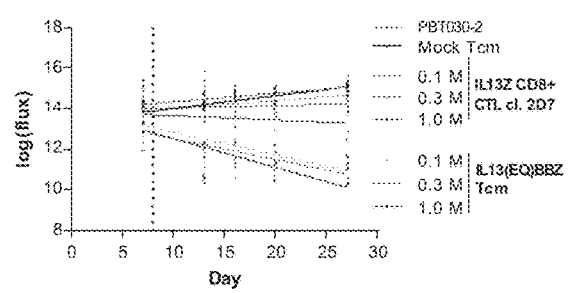
Figure 10C:
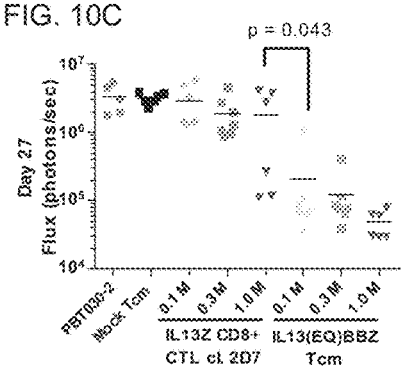
Figure 11:
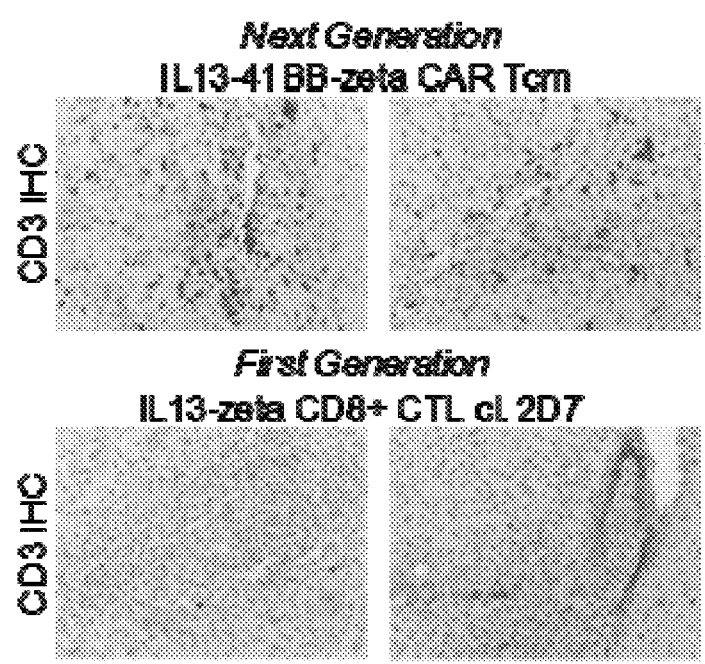
FIG. 11 depicts the results of studies demonstrating IL13(EQ)BBζ Tcm display improved persistence compared IL13-zetakine CTL clones. CD3 immunohistochemistry evaluating T cell persistence at the tumor site 7-days post T cell infusion. Significant numbers of T cells are detected for IL13(EQ)BBζ Tcm (top panel). By contrast, very few viable CD3+IL13-zetakine T cells are detected (bottom panel).

To further compare the therapeutic effectiveness of these two IL13Rα2-CAR T cell products, a dose titration of 1.0, 0.3 and $0.1 \times 10^6$ CART cells against day 8 PBT030-2 EGFP:ffuc TS-initiated tumors was performed (FIGS. 10A-C). The highest dose ($1 \times 10^6$) of IL13-zetakine CD8+ CTL cl. 2D7 mediated antitumor responses as measured by Xenogen flux in 3 of 6 animals (FIG. 10C), but no significant antitumor responses were observed at lower CART cell doses. By comparison, injection of IL13(EQ)BBζ+Tcm product mediated complete tumor regression in the majority of mice at all dose levels, including treatment with as few as $0.1 \times 10^6$ CAR T cells. These data demonstrate that IL13(EQ)BBζ+Tcm is at least 10-fold more potent than IL13-zetakine CD8+ CTL clones in antitumor efficacy. The improved anti-tumor efficacy of is due to improved T cell persistence in the tumor microenvironment. Evaluation of CD3+ T cells 7-days post i.c. injection revealed significant numbers of IL13(EQ) BBζ+Tcm in the tumor microenvironment, whereas very few first-generation IL13-zeta CTLs were present (FIG. 11).

Figure 12A:
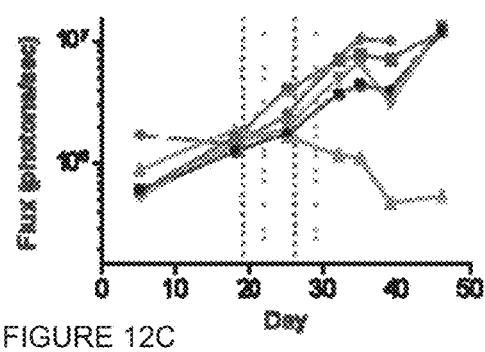
FIGS. 12A-D depict the results of experiments comparing route of CAR+ T cell delivery (i.c. versus i.v.) for large established tumors. EGFP-ffLuc+ PBT030-2 TSs ($1 \times 10^5$) were implanted into the right forebrain of NSG mice. On days 19 and 26, mice were injected i.v. through the tail vein with either $5 \times 10^6$ CAR+IL13(EQ)BBζ+Tcm ($11.8 \times 10^6$ total cells; n=4), or mock Tcm ($11.8 \times 10^6$ cells; n=4). Alternatively, on days 19, 22, 26 and 29 mice were injected i.c. with either $1 \times 10^6$ CAR+IL13(EQ)BBζ+Tcm ($2.4 \times 10^6$ total cells; n=4), or mock Tcm ($2.4 \times 10^6$ cells; n=5). Average ffLuc flux (photons/sec) over time shows that i.c. delivered IL13(EQ)BBζ Tcm mediates tumor regression of day 19 tumors. By comparison, i.v. delivered T cells do not shown reduction in tumor burden as compared to untreated or mock Tcm controls (A). Kaplan Meier survival curve demonstrates improved survival for mice treated i.c. IL13(EQ)BBZ Tcm as compared to mice treated with i.v. administered CAR+ Tcm (p=0.0003 log rank test) (B). Representative H&E and CD3 IHC of mice treated i.v. (C) versus i.c. (D) with IL13(EQ)BBZ+Tcm . CD3+ T cells were only detected in the i.c. treated group, with no CD3+ cells detected in the tumor or surrounding brain parenchyma for i.v. treated mice.
Figure 12C:
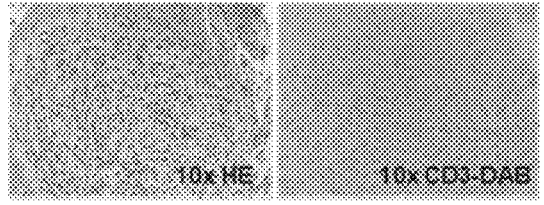
Figure 12B:
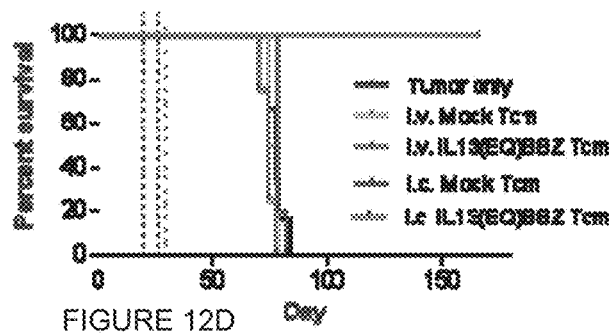
Figure 12D:
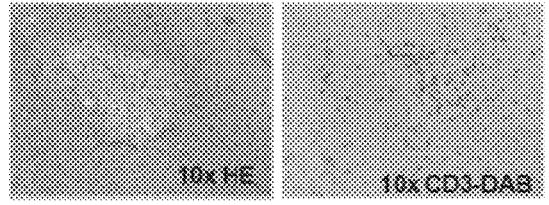

Example 9: Comparison of CAR T Cell Delivery Route for Treatment of Large TS-Initiated PBT Tumors Described below are studies that compare the route of delivery, intraveneous (i.v.) or intracranial (i.c.), on antitumor activity against invasive primary PBT lines. In pilot studies (data not shown), it was unexpectedly observed that i.v. administered IL13(EQ)BBζ+ Tcm provided no therapeutic benefit as compared to PBS for the treatment of small (day 5) PBT030-2 EGFP:ffLuc tumors. This is in contrast to the robust therapeutic efficacy observed with i.c. administered CAR+ T cells. Reasoning that day 5 PBT030-2 tumors may have been too small to recruit therapeutic T cells from the periphery, a comparison was made of i.v. versus i.c. delivery against larger day 19 PBT030-2 EGFP:ffLuc tumors. For these studies, PBT030-2 engrafted mice were treated with either two i.v. infusions ($5 \times 10^6$ CAR+ Tcm; days 19 and 26) or four i.c. infusions ($1 \times 10^6$ CAR+ Tcm; days 19, 22, 26 and 29) of IL13(EQ)BBZ+ Tcm, or mock Tcm (no CAR). Here too no therapeutic benefit as monitored by Xenogen imaging or Kaplan-Meier survival analysis for i.v. administered CAR+ T cells (FIGS. 12A and 12B). In contrast, potent antitumor activity was observed for i.c. administered IL13(EQ)BBζ+ Tcm (FIGS. 12A-B). Next, brains from a cohort of mice 7 days post T cell injection were harvested and evaluated for CD3+ human T cells by IHC. Surprisingly, for mice treated i.v. with either mock Tcm or IL13(EQ)BBζ Tcm there were no detectable CD3+ human T cells in the tumor or in others mouse brain regions where human T cells typically reside (i.e. the leptomeninges) (FIG. 12C), suggesting a deficit in tumor tropism. This is in contrast to the significant number of T cells detected in the i.c. treated mice (FIG. 12D).

Figure 13B:
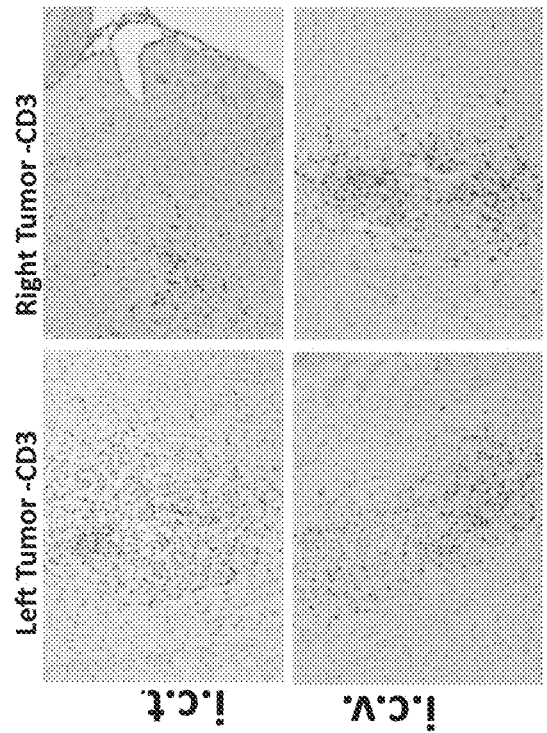
FIGS. 13A-B depict the results of studies showing that CAR+ T cell injected intracranially, either intratumoral (i.c.t.) or intraventricular (i.c.v.), can traffic to tumors on the opposite hemisphere. EGFP-ffLuc+ PBT030-2 TSs (1×105) were stereotactically implanted into the right and left forebrains of NSG mice. On day 6, mice were injected i.c. at the right tumor site with $1.0 \times 106$ IL13(EQ)BB+Tcm ($1.6 \times 106$ total cells; 63% CAR; n=4). Schematic of multifocal glioma experimental model (A). CD3 IHC showing T cells infiltrating both the right and left tumor sites (B).
Figure 13A:
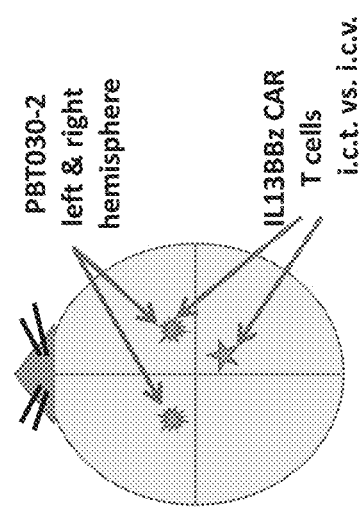

Tumor derived cytokines, particularly MCP-1/CCL2, are important in recruiting T cells to the tumor. Thus, PBT030-2 tumor cells were evaluated and it was found that this line produces high levels of MCP-1/CCL2 comparable to U251T cells (data not shown), a glioma line previously shown to attract i.v. administered effector CD8+ T cells to i.c. engrafted tumors. Malignant gliomas are highly invasive tumors and are often multi-focal in presentation. The studies described above establish that IL13BBZ $T_{CM}$ can eliminate infiltrated tumors such as PBT030-2, and mediate long-term durable antitumor activity. The capacity of intracranially delivered CAR T cells to traffic to multifocal disease was also examined. For this study PBT030-2 EGFP:ffLuc TSs were implanted in both the left and right hemispheres (FIG. 13A) and CAR+ T cells were injected only at the right tumor site. Encouragingly, for all mice evaluated (n=3) we detected T cells by CD3 IHC 7-days post T cell infusion both at the site of injection (i.e. right tumor), as well within the tumor on the left hemisphere (FIG. 13B). These findings provide evidence that CAR+ T cells are able to traffic to and infiltrate tumor foci at distant sites. Similar findings were also observed in a second tumor model using the U251T glioma cell line (data not shown).

Example 10: Comparison of Costimulatory Domains

A series of studies were conducted to evaluate various costimulatory domains. The various CAR evaluated are depicted schematically in FIG. 14A and included a first generation CD3ζ CAR lacking a costimulatory domain, two second generation CARs incorporating either a 4-1BB costimulatory domain or a CD28 costimulatory domain, and a third generation CAR containing both a CD28 costimulatory domain and 41BB costimulatory domain. All CAR constructs also contain the T2A ribosomal skip sequence and a truncated CD19 (CD19t) sequence as a marker for transduced cells.

CD4 and CD8 $T_{CM}$ were lentivirally transduced and CAR-expressing T cells were immunomagnetically enriched via anti-CD19. CD19 and IL13 (i.e., CAR) expression levels as measured by flow cytometry. The results are shown in FIG. 14B. Stability of each CAR construct was determined by dividing the CAR (IL13) mean fluorescence intenstity (MFI) by that of the transduction marker (CD19t) (FIG. 14C). The two CAR including a 4-1BB costimulatory domain exhibited the lowest expression levels as compared to the CD19t transduction marker.

Figure 15B:
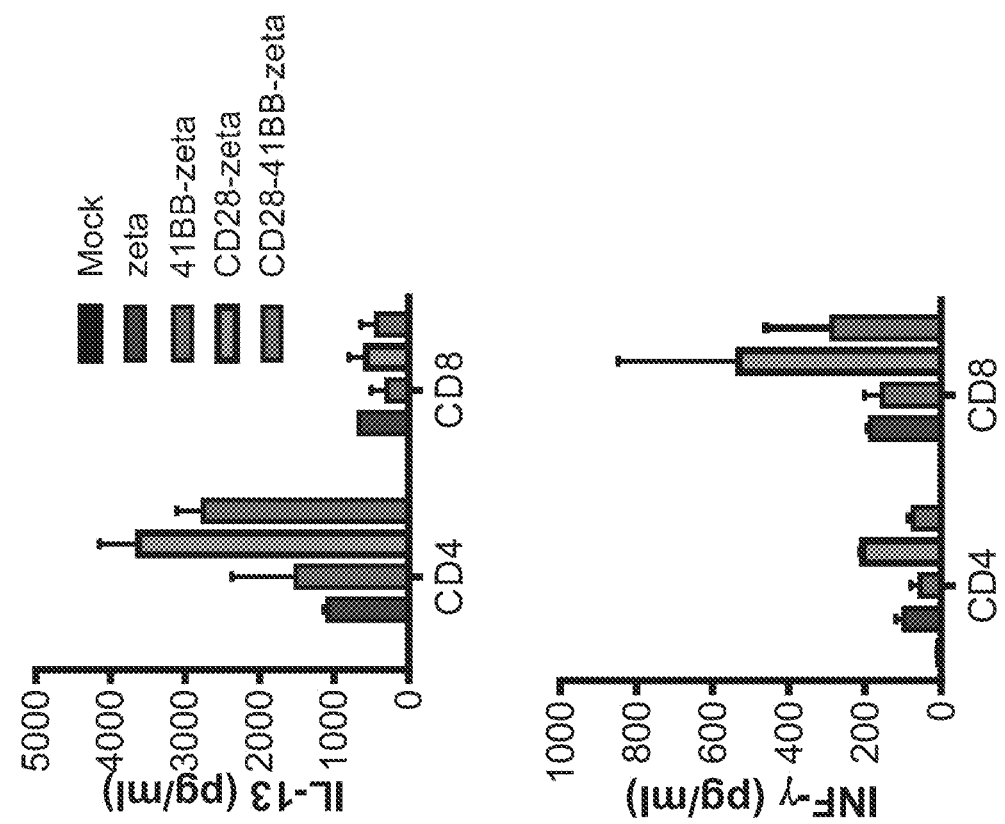
FIGS. 15A-B depict the results of studies demonstrating that IL13Rα2-specific CAR containing the 4-1BB costimulatory domain produce less Th1 and Th2 cytokines. The ability of the indicated mock-transduced or CAR-expressing T cells to kill IL13Rα2-expressing PBT030-2 tumor cell targets was determined in a 4-hour 51Cr-release assay at the indicated effector:target ratios. Mean % chromium release+ S.D. of triplicate wells are depicted (A). As expected, mock-transduced T cells did not efficiently lyse the targets. In contrast, all CAR-expressing T cells lysed the tumor cells in a similar manner. The indicated mock-transduced or CAR-expressing T cells were co-cultured overnight with IL13Rα2-expressing PBT030-2 tumor cells at a 10:1 ratio and supernatants were analyzed for IL-13 and IFN-γ levels by cytometric bead array (B). Means+S.D. of triplicate wells are depicted. Interestingly, T cells expressing the zeta, 41BB-zeta or CD28-41BB-zeta CARs exhibited lower antigen-stimulated cytokine production than T cells expressing the CD28-zeta CAR.
Figure 15A:
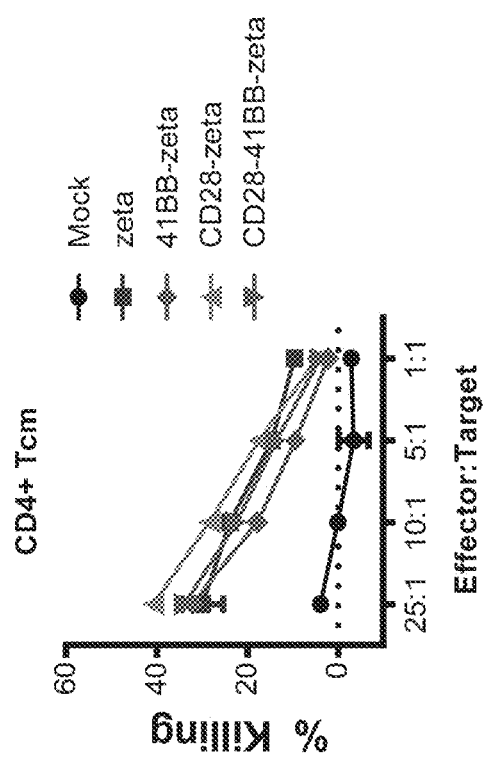

The ability of the indicated mock-transduced or CAR-expressing T cells to kill IL13Rα2-expressing PBT030-2 tumor cell targets was determined in a 4-hour $^{51}$Cr-release assay at the indicated effector:target ratios. The results of this study are in FIG. 15A (mean % chromium release±S.D. of triplicate wells are depicted). As expected, mock-transduced T cells did not efficiently lyse the targets. In contrast, all CAR-expressing T cells lysed the tumor cells in a similar manner. FIG. 15B depicts the results of a study in which the indicated mock-transduced or CAR-expressing T cells were co-cultured overnight with IL13Rα2-expressing PBT030-2 tumor cells at a 10:1 ratio and supernatants were analyzed for IL-13 and IFN-γ levels by cytometric bead array. Interestingly, T cells expressing the zeta, 41BB-zeta or CD28-41BB-zeta CARs exhibited lower antigen-stimulated cytokine production than T cells expressing the CD28-zeta CAR.

The in vivo efficacy of the various CAR was examined as follows. Briefly, NSG mice received an intracranial injection of ffLuc+ PBT030-2 tumor cells on day 0, and were randomized into 6 groups (n=9-10 mice per group) for i.c. treatment with either PBS (Tumor Only), mock-transduced T cells or T cells expressing the indicated IL13Rα2-specific CAR on day 8. Quantitative bioluminescence imaging was then carried out to monitor tumor growth over time. Bioluminescence images for representative mice in each group (FIG. 16A). Flux levels for each mouse at Day 27 (FIG. 16B). All groups treated with IL13Rα2-specific CAR T cells, except those treated with T cells expressing the CD28-CAR, show statistically-significant reduction in tumor volume compared to mice treated with mock-transduced T cells (FIG. 16C).

Example 11: Amino Acid Sequence of IL13(EQ)BBζ/CD19t

The complete amino acid sequence of IL13(EQ)BBζ/CD19t is depicted in FIGS. 17A-B. The entire sequence (SEQ ID NO:1) includes: a 22 amino acid GMCSF signal peptide (SEQ ID NO:2), a 112 amino acid IL-13 sequence (SEQ ID NO:3; amino acid substitution E13Y shown in bold); a 229 amino acid IgG4 sequence (SEQ ID NO:4; with amino acid substitutions L235E and N297Q shown in bold); a 22 amino acid CD4 transmembrane sequence (SEQ ID NO:5); a 42 amino acid 4-1BB sequence (SEQ ID NO:6); a 3 amino acid Gly linker; a 112 amino acid CD3ζ sequence (SEQ ID NO:7); a 24 amino acid T2A sequence (SEQ ID NO:8); and a 323 amino acid CD19t sequence (SEQ ID NO:9).

The mature chimeric antigen receptor sequence (SEQ ID NO:10) includes: a 112 amino acid IL-13 sequence (SEQ ID NO:3; amino acid substitution E13Y shown in bold); a 229 amino acid IgG4 sequence (SEQ ID NO:4; with amino acid substitutions L235E and N297Q shown in bold); at 22 amino acid CD4 sequence (SEQ ID NO:5); a 42 amino acid 4-1BB sequence (SEQ ID NO:6); a 3 amino acid Gly linker; and a 112 amino acid CD3ζ sequence (SEQ ID NO:7). Within this CAR sequence (SEQ ID NO:10) is the IL-13/IgG4/CD4t/41-BB sequence (SEQ ID NO:11), which includes: a 112 amino acid IL-13 sequence (SEQ ID NO:3; amino acid substitution E13Y shown in bold); a 229 amino acid IgG4 sequence (SEQ ID NO:4; with amino acid substitutions L235E and N297Q shown in bold); at 22 amino acid CD4 sequence (SEQ ID NO:5); and a 42 amino acid 4-1BB sequence (SEQ ID NO:6). The IL13/IgG4/CD4t/4-1BB sequence (SEQ ID NO:11) can be joined to the 112 amino acid CD3ζ sequence (SEQ ID NO:7) by a linker such as a Gly Gly Gly linker. The CAR sequence (SEQ ID NO:10) can be preceded by a 22 amino acid GMCSF signal peptide (SEQ ID NO:2).

FIGS. 18A-O depicts a comparison of the sequences of IL13(EQ)41BBζ[IL13{EQ}41BBζ T2A-CD19t_epHIV7; pF02630] (SEQ ID NO:12) and CD19Rop_epHIV7 (pJ01683) (SEQ ID NO:13).

Example 12: Amino Acid Sequence of IL13(EQ)BBζ/CD19t

FIGS. 19-26 depict the amino acid sequences of additional CAR directed against IL13Rα2 in each case the various domains are labelled except for the GlyGlyGly spacer located between certain intracellular domains. Each includes human IL13 with and Glu to Tyr (SEQ ID NO:3; amino acid substitution E13Y shown in highlighted). In the expression vector used to express these CAR, the amino acid sequence expressed can include a 24 amino acid T2A sequence (SEQ ID NO:8); and a 323 amino acid CD19t sequence (SEQ ID NO:9) to permit coordinated expression of a truncated CD19 sequence on the surface of CAR-expressing cells.

A panel of CAR comprising human IL13(E13Y) domain, a CD28 tm domain, a CD28gg costimulatory domain, a 4-1BB costimulatory domain, and a CD3ζ domain CAR backbone and including either a HL (22 amino acids) spacer, a CD8 hinge (48 amino acids) spacer, IgG4-HL-CH3 (129 amino acids) spacer or a IgG4(EQ) (229 amino acids) spacer were tested for their ability to mediate IL13Rα2-specific killing as evaluated in a 72-hour co-culture assay. With the exception of HL (22 amino acids) which appeared to have poor CAR expression in this system, all were active.

What is claimed is:

1. A composition comprising T cells harboring a nucleic acid molecule comprising a nucleotide sequence encoding a chimeric antigen receptor molecule comprising the amino acid sequence of SEQ ID NO: 10.

2. The composition of claim 1, wherein the nucleic acid molecule comprises a vector.

3. The composition of claim 2, wherein the vector is a lentiviral vector.

4. The composition of claim 1, wherein the nucleic acid molecule further comprises a nucleotide sequence encoding a GMSCFRa signal sequence preceding the nucleotide sequence encoding the chimeric antigen receptor.

5. The composition of claim 4, wherein the GMSCFRa signal sequence comprises the amino acid sequence of SEQ ID NO:2.

6. The composition of claim 1, wherein the nucleic acid molecule further comprises a nucleotide sequence encoding a T2A ribosome skip sequence following the nucleotide sequence encoding the chimeric antigen receptor.

7. The composition of claim 6, wherein T2A ribosome skip sequence comprises the amino acid sequence of SEQ ID NO:8.

8. The composition of claim 6, wherein the nucleic acid molecule further comprises a nucleotide sequence encoding a truncated CD19 following the nucleotide sequence encoding the T2A ribosome skip sequence.

9. The composition of claim 8, wherein the truncated CD19 comprises the amino acid sequence of SEQ ID NO:9.

10. The composition of claim 8, wherein the truncated CD19 consists of the amino acid sequence of SEQ ID NO:9.

11. The composition of claim 1, wherein the T cells comprise central memory T cells.

12. A method of treating cancer in a patient comprising administering a population of autologous or allogeneic human T cells transduced by a vector comprising an expression cassette encoding a chimeric antigen receptor, wherein chimeric antigen receptor comprises the amino acid sequence of SEQ ID NO: 10.

13. The method of claim 12, wherein the population of human T cells comprise central memory T cells.

14. The method claim 12, wherein the cancer is glioblastoma.

15. The method of claim 12, wherein the human T cells are autologous T cells.

16. The method of claim 14, wherein the human T cells are autologous T cells.

\* \* \* \* \*

UNITED STATES PATENT AND TRADEMARK OFFICE
CERTIFICATE OF CORRECTION

Page 1 of 1

PATENT NO. : 10,676,717 B2
APPLICATION NO. : 15/918901
DATED : June 9, 2020
INVENTOR(S) : Christine E. Brown, Stephen J. Forman and Armen Mardiros It is certified that error appears in the above-identified patent and that said Letters Patent is hereby corrected as shown below:

On the Title Page

Column 1, under "Inventors", after "Stephen J. Forman, Duarte, CA (US)", add -- Armen Mardiros, Duarte, CA (US) --

Signed and Sealed this
Eleventh Day of July, 2023

Katherine Kelly Vidal
*Director of the United States Patent and Trademark Office*